US007758876B2

(12) United States Patent
Klinman et al.

(10) Patent No.: US 7,758,876 B2
(45) Date of Patent: Jul. 20, 2010

(54) METHOD OF PREVENTING INFECTIONS FROM BIOTERRORISM AGENTS WITH IMMUNOSTIMULATORY CPG OLIGONUCLEOTIDES

(75) Inventors: Dennis M. Klinman, Potomac, MD (US); Bruce Ivins, Frederick, MD (US); Daniela Verthelyi, Potomac, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 617 days.

(21) Appl. No.: 10/533,634

(22) PCT Filed: Oct. 31, 2003

(86) PCT No.: PCT/US03/34523

§ 371 (c)(1), (2), (4) Date: Apr. 29, 2005

(87) PCT Pub. No.: WO2004/098491

PCT Pub. Date: Nov. 18, 2004

(65) Prior Publication Data

US 2006/0019239 A1 Jan. 26, 2006

Related U.S. Application Data

(60) Provisional application No. 60/422,964, filed on Nov. 1, 2002.

(51) Int. Cl.
*A61K 45/00* (2006.01)

(52) U.S. Cl. .................................................. 424/278.1

(58) Field of Classification Search ....................... None
See application file for complete search history.

(56) References Cited

U.S. PATENT DOCUMENTS 6,194,388 B1 2/2001 Krieg et al.
6,207,646 B1 3/2001 Krieg et al.
6,214,806 B1 4/2001 Krieg et al.
6,218,371 B1 4/2001 Krieg et al.
6,239,116 B1 5/2001 Krieg et al.
6,339,068 B1 1/2002 Krieg et al.
6,406,705 B1 6/2002 Davis et al.
6,423,539 B2 7/2002 Fong et al.
6,428,788 B1 8/2002 Debinski et al.
6,429,199 B1 8/2002 Krieg et al.
6,498,148 B1 12/2002 Raz
6,514,948 B1 2/2003 Raz et al.
6,534,062 B2 3/2003 Krieg-Kowald et al.
6,552,006 B2 4/2003 Raz et al.
6,562,798 B1 5/2003 Schwartz
6,589,940 B1 7/2003 Raz et al.
6,610,661 B1 8/2003 Carson et al.
6,613,751 B2 9/2003 Raz et al.
6,653,292 B1 11/2003 Krieg et al.
2001/0034330 A1 10/2001 Kensil
2001/0036462 A1 11/2001 Fong et al.
2001/0044416 A1 11/2001 McCluskie et al.
2001/0046967 A1 11/2001 Van Nest
2002/0006403 A1 1/2002 Yu et al.
2002/0028784 A1 3/2002 Van Nest
2002/0042383 A1 4/2002 Yew et al.
2002/0042387 A1 4/2002 Raz et al.
2002/0055477 A1 5/2002 Van Nest et al.
2002/0064515 A1 5/2002 Krieg et al.
2002/0065236 A1 5/2002 Yew et al.
2002/0086295 A1 7/2002 Raz et al.
2002/0086839 A1 7/2002 Raz et al.
2002/0090724 A1 7/2002 Taylor et al.
2002/0091095 A1 7/2002 Phillips et al.
2002/0091097 A1 7/2002 Bratzler et al.
2003/0060440 A1 3/2003 Klinman et al.
2003/0144229 A1 7/2003 Klinman et al.

FOREIGN PATENT DOCUMENTS

EP 1 198 249 4/2002
WO WO 92/18522 10/1992
WO WO 94/19945 9/1994
WO WO 97/28259 8/1997
WO WO 99/11275 3/1999
WO WO 00/06588 2/2000
WO WO 00/20039 4/2000
WO WO 00/21556 4/2000
WO WO 00/61151 10/2000

(Continued)

OTHER PUBLICATIONS

Jones et al. Synthetic oligodeoxynucleotides containing CpG motifs enhance immunogenicity of a peptide malaria vaccine in Aotus monkeys. Vaccine, 1999, vol. 17, 3065-3071.*

Verthelyi et al. CpG oligodeoxynucleotides as vaccine adjuvants in primates. The Journal of Immunology, Feb. 15, 2002, vol. 168, 1659-1663.*

Ivins et al. Recent advances in the development of an improved, human anthrax vaccine. Eur. J. Epidemiol., Mar. 1988, vol. 4, No. 1, p. 12-19.*

Su et al. Vaccination with novel immunostimulatory adjuvants against blood-stage malaria in mice. Infection and Immunity, Sep. 2003, vol. 71, No. 9, 5178-5187.*

(Continued)

*Primary Examiner*—Emily M. Le
(74) *Attorney, Agent, or Firm*—Klarquist Sparkman, LLP

(57) ABSTRACT

The present disclosure relates to a method of preventing or treating an infection caused by a bioterrorism agent, specifically to a method of increasing an immune response to a bioterrorism agent using an oligodeoxynucleotide including a CpG motif, and a method of enhancing the immunogenicity of a vaccine against a bioterrorism agent using an oligodeoxynucleotide including a CpG motif.

27 Claims, 9 Drawing Sheets

FOREIGN PATENT DOCUMENTS

| | | |
|---|---|---|
| WO | WO 00/62787 | 10/2000 |
| WO | WO 00/67023 | 11/2000 |
| WO | WO 01/00232 | 1/2001 |
| WO | WO 01/02007 | 1/2001 |
| WO | WO 01/12223 | 2/2001 |
| WO | WO 01/22990 | 4/2001 |
| WO | WO 01/51500 | 7/2001 |
| WO | WO 01/55341 | 8/2001 |
| WO | WO 01/68077 | 9/2001 |
| WO | WO 01/68103 | 9/2001 |
| WO | WO 01/68116 | 9/2001 |
| WO | WO 01/68117 | 9/2001 |
| WO | WO 03/040308 | 5/2003 |
| WO | WO 2004/005476 | 1/2004 |

OTHER PUBLICATIONS

Klinman et al. CpG oligonucletoides improve the protecitve immune response induced by the anthrax vaccinatio of rhesus macaques. Vaccine, 2004, vol. 22, 2881-2886.*

Little et al. Effect of aluminum hdryoxide adjvuant and formaldehyde in the formulation of rPA anthrax vaccine. Vaccine, 2007, vol. 25, 2771-2777.*

Threagill et al. Mitogenic synthetic polynucleotides supress the antibody resposne to a bacterial polysaccharide. Vaccine. 1998, vol. 16, No. 1, 76-82.*

Klinman, "CpG oligonucleotides accelerate and boost the immune response elicited by AVA, the licensed anthrax vaccine," *Expert Rev. Vaccines* 5(3):365-369, 2006.

Klinman et al., "Use of CpG oligodeoxynucleotides as immune adjuvants," *Immunological Reviews* 199:201-216, 2004.

Dalpke et al., "Immunopharmacology of CpG DNA," *Biol. Chem.*, 383:1491-1500, (Oct. 2002).

Klinman et al., "Immune Recognition of Foreign DNA: A Cure for Bioterrorism?," *Immunity*, 11:123-129 (Aug. 1999).

Krieg and Sim, Report No. A415554, "Enhancement of the Anthrax AVA Vaccine with CpG ODN's," *Medicine and Medical Research*, Abstract only, (Aug. 28, 2005).

Krieg and Sim, Report No. 44498-LS-DRP.1, "Enhancement of the Anthrax AVA Vaccine with CpG ODN's," *U.S. Army Research Office*, 8 pages, (2005).

Williamson et al., "Co-immunisation with plasmid DNA cocktail primes mice against anthrax plague," *Vaccine*, 20:2933-2941, (2002).

Anfossi, et al., "An oligomer complementary to c-myb-encoded mRNA inhibits proliferation of human myeloid leukemia cell lines". Proc. Natl. Acad. Sci. USA 86:3379-3383 (1989).

Bauer, et al., "Bacterial CpG-DNA Triggers Activation and Maturation of Human CD11c-, CD123+ Dendritic Cells". J. Immunol. 166:5000-5007 (2001).

Benimetskaya, et al., "Formation of a G-tetrad and higher order structures correlates with biological activity of the ReIA (NF-kBp65) 'antisense' oligodeoxynucleotide". Nucleic Acids Research 25(13):2648-2656 (1997).

Boggs, et al., "Characterization and modulation of immune stimulation by modified oligonucleotides". Antisense Nucl. Acid Drug Dev. 7(5):461-471 (1997).

Branda, et al., "Amplification of antibody production by phosphorothioate oligodeoxynucleotides". J. Lab Clin. Med. 128(3):329-338 (1996).

Chu, et al., "CpG oligodeoxynucleotides act as adjuvants that switch on T helper 1 (Th1) immunity". J. Exp. Med. 186(10):1623-1631 (1997).

Deml, et al., "Immunostimulatory CpG motifs trigger a T Helper-1 immune response to Human Immunodeficiency Virus Type-1 (HIV-1) gp160 envelope protein". Clin. Chem. Lab. Med. 37(3):199-204 (1999).

Gao, et al., "Phosphorothioate oligonucleotides are inhibitors of human DNA polymerases and Rnase H: Implications for antisense technology". Mol. Pharmacol. 41:223-229 (1992).

Gursel, et al., "Differential and Competitive Activation of Human Immune Cells by Distinct Classes of CpG Oligodeoxynucleotide". J. Leuko. Biol. 71:813-820 (2002).

Halpern, et al., "Bacterial DNA induces murine interferon-gamma production by stimulation of interleukin-12 and tumor necrosis factor-alpha". Cell Immunol. 167(1):72-78 (1996).

Ishibashi, et al., "Sp1 Decoy Transfected to Carcinoma Cells Suppresses the Expression of Vascular Endothelial Growth Factor, Transforming Growth Factor β, and Tissue Factor and Also Cell Growth and Invasion Activities". Cancer Research 60:6531-6536 (2000).

Iversen, et al., "Pharmacokinetics of an antisense phosphorothioate oigodeoxynucleotide against rev from human immunodeficiency virus type 1 in the adult male rat following single inections and continuous infusion". Antisense Res. Dev. 4:43-52 (1994).

Jilek, et al., "Antigen-Independent Suppression of the Allergic Immune Response to Bee Venom Phospholipase A2 by DNA Vaccination in CBA/J Mice". J. Immunol. 166:3612-3621 (2001).

Kadowaki, et al., "Distinct CpG DNA and Polyinosinic-Polycytidylic Acid Double Stranded RNA, Respectively, Stimulate CD11c- Type 2 Dendritic Cell Precursoes and CD11 c+ Dendritic cells to Produce Type I IFN". J. Immunol. 166:2291-2295 (2001).

Klinman, et al., "Activation of the innate immune system by CpG oligodeoxynucleotides: immunoprotective activity and safety". Springer Semin. Immunopathol. 22:173-183 (2000).

Krieg, et al., "CpG motifs in bacterial DNA and their immune effect". Annu. Rev. Immunol. 20:709-760 (2002).

Krieg, et al., "Brief Communication: Oligodeoxynucleotide Modifications Determine the Magnitude of B-Cell Stimulation by CpG Motifs". Antisense & Nucleic Acid Drug Development 6:133-139 (1996).

Krieg, et al., "Leukocyte stimulation by oligodeoxynucleotides". Applied Antisense Oligonucleotide Tech. (Book):431-448 (1998).

Krieg, et al., "CpG DNA: A pathogenic factor in systemic lupus erythematosus?". J. Clin. Immunol. 15(6):284-292 (1995).

Krieg, et al., "A role for endogenous retroviral sequences in the regulation of lymphocyte activation". J. Immunol. 143(8):2448-2451 (1989).

Krieg, et al., "CpG motifs in bacterial DNA trigger direct B-cell activation". Nature 374:546-549 (1995).

Krug, et al., "Identification of CpG Oligonucleotide Sequences with High Induction of IFN-α/β in Plasmacytoid Dendritic Cells". Eur. J. Immunol. 31:2154-2163 (2001).

Krug, et al., "Toll-like Receptor Expression Reveals CpG DNA as a Unigue Microbial Stimulus for Plasmacytoid Dendritic Cells Which Synergizes With CD40 Ligand to Induce High Amounts of IL-12". Eur. J. Immunol. 31:3026-3037 (2001).

Kuramoto, et al., "Oligonucleotide sequences required for natural killer cell activation". Jpn. J. Cancer Res. 83:1128-1131 (1992).

Lang, et al., "Guanosine-rich oligodeoxynucleotides induce proliferation of macrophage progenitors in cultures of murine bone marrow cells". Eur. J. Immunol. 29:3496-3506 (1999).

Lapatschek, et al., "Activation of Macrophages and B Lymphocytes by an Oligodeoxynucleotide Derived from an Acutely Pathogenic Simian Immunodeficiency Virus". Antisense Nucleic Acid Drug Dev. 8(5):357-370 (1998).

Maltese, et al., "Sequence context of antisense RelA/NF-kB phohphorothioates determines specificity". Nucleic Acids Research 23(7):1146-1151 (1995).

Manzel, et al., "Lack of Immune Stimulation by Immobilized CpG-oligonucletide". Antisense & Nucleic Acid Drug Development 9(5):459-464 (1999).

Matson, et al., "Nonspecific suppression of [3H]thymidine incorporation by control oligonucleotides". Antisense Res. Dev. 2(4):325-330 (1992).

McIntyre, et al., "A sense phosphorothioate oligonucleotide directed to the initiation codon of transcription factor NF-kappa B p65 causes sequence-specific immune stimulation". Antisense Res. Dev. 3(4):309-322 (1993).

Pisetsky, "Immunological consequences of nucleic acid therapy". Antisense Res. Dev. 5:219-225 (1995).

Prasad, et al., "Oligonucleotides Tethered to a Short Polyguanylic Acid Stretch are Targeted to Macrophages: Enhanced Antiviral Activity of a Vesicular Stomatitis Virus-Specific Antisense Oligonucleotide". Antimicrobial Agents and Chemotherapy 43(11):2689-2696 (Nov. 1999).

Raz, et al., "Intradermal gene immunization: the possible role of DNA uptake in the induction of cellular immunity to viruses". Proc. Natl. Acad. Sci. USA 91:9519-9523 (1994).

Roman, et al., "Immunostimulatory DNA sequences function as T helper-1-promoting aduvants". Nature Med. 3(8):849-854 (1997).

Schwartz, et al., "CpG motifs in bacterial DNA cause inflammation in the lower respiratory tract". J. Clin. Invest. 100(1):68-73 (1997).

Stacey, et al., "Immunostimulatory DNA as an adjuvant in vaccination against Leishmania major". Infect. Immun. 67:3719-3726 (1999).

Tokunaga, et al., "A synthetic single-stranded DNA, poly(dG, dC), induces interferon-$\alpha/\beta$ and -$\gamma$, augments natural killer activity and suppresses tumor growth". Jpn. J. Cancer Res. 79:682-686 (1988).

Tokunaga, et al., "Synthetic oligonucleotides with particular base sequences from the cDNA encoding proteins of Mycobacterium bovis BCG induce interferons and activate natural killer cells". Microbiol. Immunol. 36(1):55-66 (1992).

Verthelyi, et al., "Human Peripheral Blood Cells Differentially Recognize and Respond to Two Distinct CpG Motifs". J. Immunol. 166:2372-2377 (2001).

Verthelyi, et al., "CpG Oligodeoxynucleotides as Vaccine Adjuvants in Primates". J. Immunol. 168:1659-1663 (2002).

Weiner, et al., "Immunostimulatory oligodeoxynucleotides containing the CpG motif are effective as immune adjuvants in tumor antigen immunization". Proc. Natl. Acad. Sci. USA 94:10833-10837 (1997).

Yamamoto, et al., "Ability of oligonucleotides with certain palindromes to induce interferon production and augment natural killer cell activity is associated with their base length". Antisense Res. Dev. 4:119-123 (1994).

Yamamoto, "Unique palindromic sequences in synthetic oligonucleotides are required to induce inf and augment INF-mediated natural killer activity". J. Immunol. 148(12):4072-4076 (1992).

Yamamoto, et al., "Synthetic oligonucleotides with certain palindromes stimulate interferon production of human peripheral blood lymphocytes in vitro". Jpn. J. Cancer Res. 85:775-779 (1994).

Yamamoto, et al., "Mode of action of oligonucleotide fraction extracted from Mycobacterium bovis BeG". Kekkaku 69(9):29-32 (1994).

Yamamoto, et al., "Lipofection of synthetic oligodeoxyribonucleotide having a palindromic sequence AACGTT to murine splenocytes enhances interferon production and natural killer activity". Microbiol. Immunol. 38(10):831-836 (1994).

Yaswen, et al., "Effects of Sequence of Thioated Oligonucleotides on Cultured Human Mammary Epithelial Cells". Antisense Research and Development 3:67-77 (1993).

Yi, et al., "IFN-$\gamma$ promotes IL-6 and 1gM secretion in response to CpG motifs in bacterial DNA and oligonucleotides". J. Immunol. 156:558-564 (1996).

Zelphati, et al., "Inhibition of HIV-1 Replication in Cultured Cells with Antisense Oligonucleotides Encapsulated in Immunoliposomes". Antisense Res. Dev. 3:323 (1993).

Decision of Interference No. 105,171, *The Regents of California* verus *University of Iowa, Coley Pharmaceutical Group, Inc.* and The United States of America. Jul. 17, 2006.

Verthelyi et al., "Human Peripheral Blood Cells Differentially Recognize and Respond to Two Distinct CpG Motifs," *The Journal of Immunology*, 166:2372-2377, (2001).

* cited by examiner

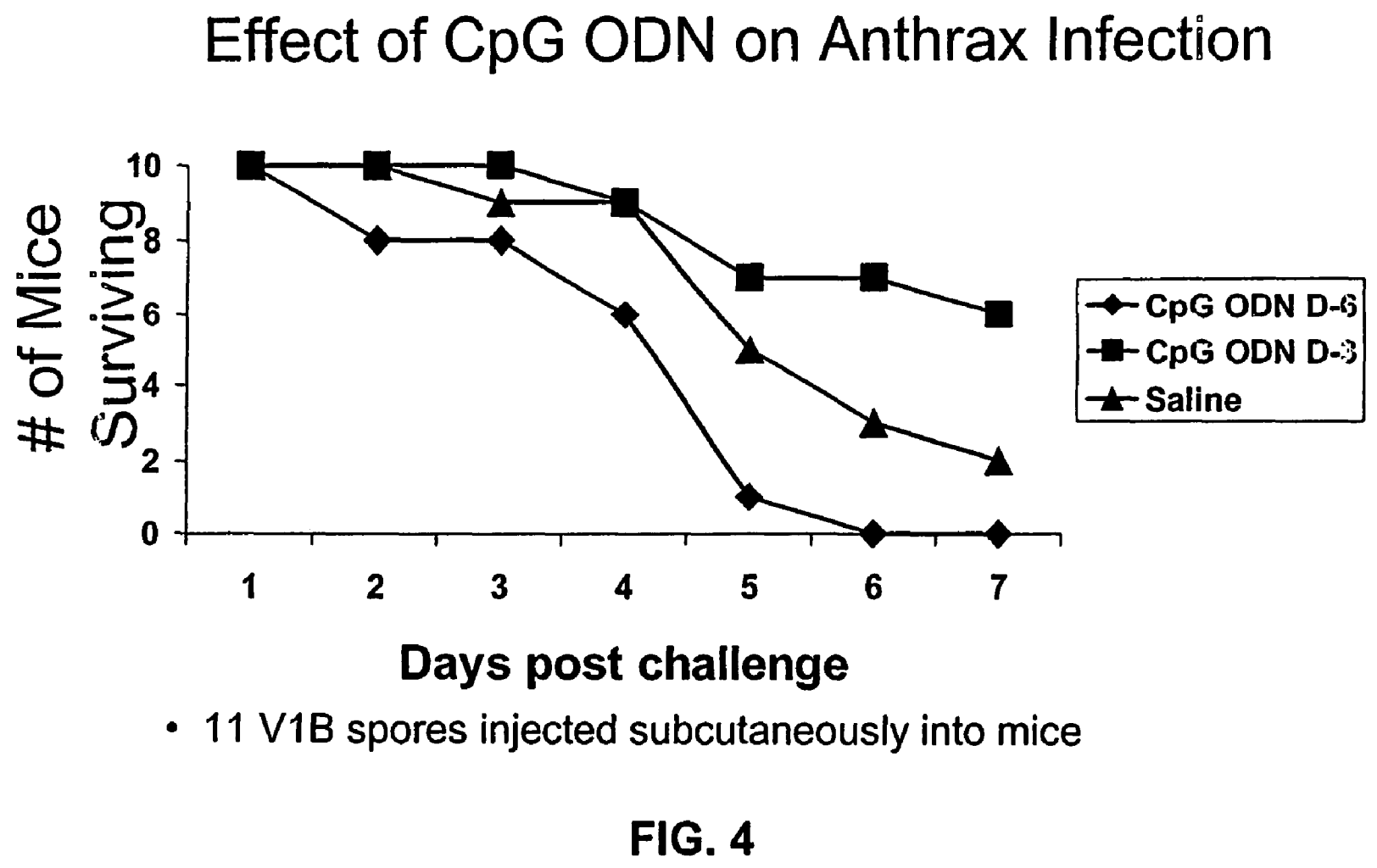

Effect of CpG ODN on Anthrax Infection

CpG ODN D-6
CpG ODN D-3
Saline # of Mice Surviving 10
8
6
4
2
0

1 2 3 4 5 6 7

Days post challenge

• 11 V1B spores injected subcutaneously into mice

FIG. 4

METHOD OF PREVENTING INFECTIONS FROM BIOTERRORISM AGENTS WITH IMMUNOSTIMULATORY CPG OLIGONUCLEOTIDES

PRIORITY CLAIM

This application is a §371 U.S. National Stage of International Application No. PCT/US2003/034523, filed Oct. 31, 2003, which was published in English under PCT Article 21(2), which in turn claims the benefit of U.S. Provisional Application No. 60/422,964, filed Nov. 1, 2002, which is incorporated herein by reference in its entirety.

FIELD

The present disclosure relates to a method of inhibiting or treating an infection caused by a bioterrorism agent, specifically to a method of increasing an immune response to a bioterrorism agent using an oligodeoxynucleotide including a CpG motif.

BACKGROUND

Bioterrorism agents are bacteria, viruses, and toxins that are dispersed deliberately in an environment to cause disease or death in humans or animals. Bioterrorism agents include, but are not limited to, *Bacillus anthracis* (anthrax), *Yersinia pestis* (plague), *Variola major* (smallpox), tick-borne encephalitis virus (TBEV) (tick-borne encephalitis), and Ebola virus (Ebola). Bioterrorism agents can also include biotoxins, which are toxins produced by certain biological organisms. Exemplary biotoxins are botulinum toxin, which is produced by the bacterium *Clostridium botulinum*, and ricin, which is isolated from castor oil seeds.

The immune system has evolved two general strategies for combating infections from bioterrorism agents such as anthrax. A rapid "innate" immune response is induced when Toll-like receptors (TLR) on host cells interact with highly conserved pathogen associated molecular patterns (PAMPs) expressed by infectious microorganisms (Marrack and Kappler, *Cell* 76:323, 1994; Medzhitov and Janeway, *Cur. Op. Immunol.* 9:4, 1997). The resultant production of polyreactive antibodies and immunostimulatory cytokines check the pathogen's early proliferation and spread (Marrack and Kappler, *Cell* 76:323, 1994; Medzhitov and Janeway, *Cur. Op. Immunol.* 9:4, 1997; Medzhitov and Janeway, *Cell* 91:295, 1998). A subsequent antigen-specific immune response is then generated against determinants unique to the pathogen that helps to eradicate the remaining organisms and provide long-lasting protective memory.

Vaccination can be used to protect against the effects of some bioterrorism agents. For example, in the case of anthrax, "protective antigen" (PA) is necessary for vaccine immunogenicity (Ivins et al., *Infect. Immun.* 60:662, 1992; Welkos and Friedlander, *Microb. Pathog.* 5:127, 1998). Antibodies against PA prevent anthrax toxin from binding to host cells, thus abrogating toxicity (Little and Ivins, *Microbes. Infect.* 1:131, 1999). Additionally, antibodies to PA can inhibit the germination of spores while improving their phagocytosis and killing by macrophages (Welkos et al., *Microbiology* 147:1677, 2001). Unfortunately, the currently licensed human anthrax vaccine (AVA) requires six vaccinations over eighteen months followed by yearly boosters to induce and maintain protective anti-PA titers (Pittman et al., *Vaccine* 20:1412, 2002; Pittman et al., *Vaccine* 20:972, 2001).

In some vaccinees, this regimen is associated with undesirable local reactogenicity (Pittman et al., *Vaccine* 20:972, 2001).

Thus, there exists a need for agents that prevent or treat infections caused by bioterrorism agents, or that increase the immunogenicity of a vaccine against a bioterrorism agent, in order to treat or prevent infections in individuals exposed to or at risk of exposure to bioterrorism agents.

SUMMARY

Described herein are methods of treating or preventing an infection in a subject who has been exposed to or is at risk for exposure to a bioterrorism agent. In some embodiments, the method is a method of increasing an immune response to a bioterrorism agent using an oligodeoxynucleotide including a CpG motif. Other methods are methods of increasing an immune response to a bioterrorism agent using an oligodeoxynucleotide including a CpG motif and an additional anti-infective agent. Still other methods include enhancing the immunogenicity of a vaccine against a bioterrorism agent using an oligodeoxynucleotide including a CpG motif.

In some embodiments, a therapeutically effective amount of an immunostimulatory D oligodeoxynucleotide or an immunostimulatory K oligodeoxynucleotide is administered to the subject, thereby treating or preventing the infection.

Also described herein are methods of treating or preventing an infection in a subject who has been exposed to or is at risk for exposure to *Bacillus anthracis*. In some embodiments, the method includes administering a therapeutically effective amount of an immunostimulatory D oligodeoxynucleotide or an immunostimulatory K oligodeoxynucleotide to a subject.

Other methods described herein are methods of treating or preventing an infection in a subject who has been exposed to or is at risk for exposure to a bioterrorism agent by administering a therapeutically effective amount of an immunostimulatory D oligodeoxynucleotide or an immunostimulatory K oligodeoxynucleotide to the subject in combination with an anti-infective agent, thereby treating or preventing the infection.

Further embodiments are methods of treating or preventing an infection in a subject who has been exposed to or is at risk for exposure to *Bacillus anthracis*. In some embodiments, the method includes administering a therapeutically effective amount of an immunostimulatory D oligodeoxynucleotide or an immunostimulatory K oligodeoxynucleotide in combination with an anti-infective agent to a subject.

Also described herein are methods of enhancing the immunogenicity of a vaccine against a bioterrorism agent in a subject. In some embodiments, a therapeutically effective amount of an immunostimulatory D oligodeoxynucleotide or an immunostimulatory K oligodeoxynucleotide is administered to a subject in combination with a vaccine against a bioterrorism agent, thereby enhancing the immunogenicity of the vaccine against a bioterrorism agent.

Still further embodiments are methods of enhancing the immunogenicity of an antigen from *Bacillus anthracis*, comprising administering to the subject a therapeutically effective amount of an immunostimulatory D oligodeoxynucleotide or an immunostimulatory K oligodeoxynucleotide in combination with an antigen from *Bacillus anthracis*, thereby enhancing the immunogenicity of the antigen.

The features and advantages will become more apparent from the following detailed description of several embodiments, which proceeds with reference to the accompanying figures.

BRIEF DESCRIPTION OF THE FIGURES

In FIG. 3*a*, mice were treated with 25-150 μg of CpG ODN on day 0, and then challenged with 300 LD50 of mouse-adapted Ebola Zaire. In FIG. 3*b*, mice were treated with 100 μg of CpG ODN on the day shown, and then challenged with 300 LD50 of mouse-adapted Ebola Zaire.

N=10 mice/group.

FIG. 4 is a graph showing that CpG ODNs increase survival times in mice exposed to anthrax spores. Mice were treated at the times shown with 100 μg of CpG ODN, and then challenged with 11 LD 50 anthrax spores. Survival is shown (N=10/group).

Figure 5:
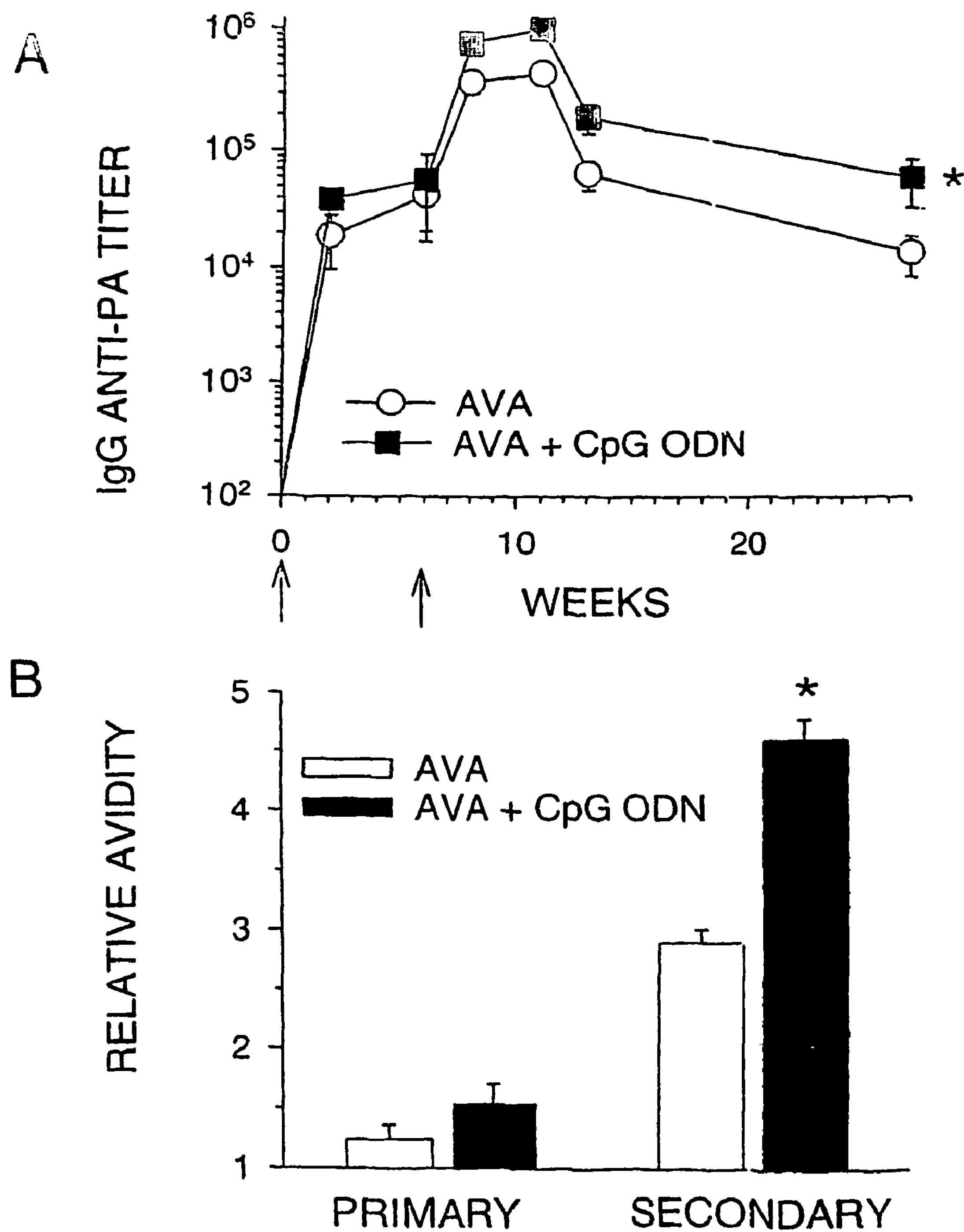

FIG. 5 is a graph that shows the effect of K ODN on the avidity of the anti-PA response. N=6 per group.

Figure 6:
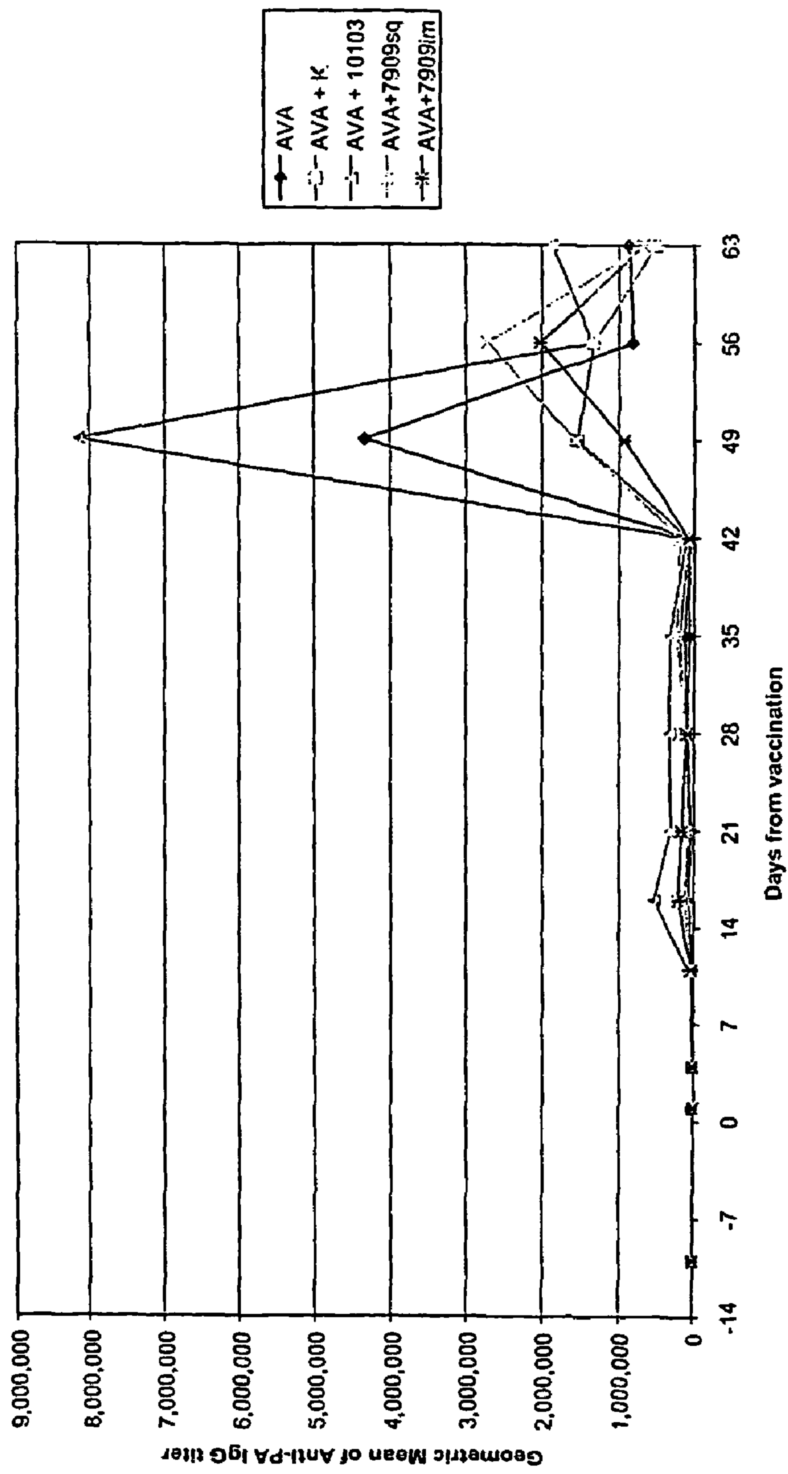

FIG. 6 is a line graph of the geometric mean anti-PA IgG titer following treatment with the anthrax vaccine AVA alone, AVA plus K ODN, AVA plus ODN 10103, and AVA plus ODN 7909.

Figure 7:
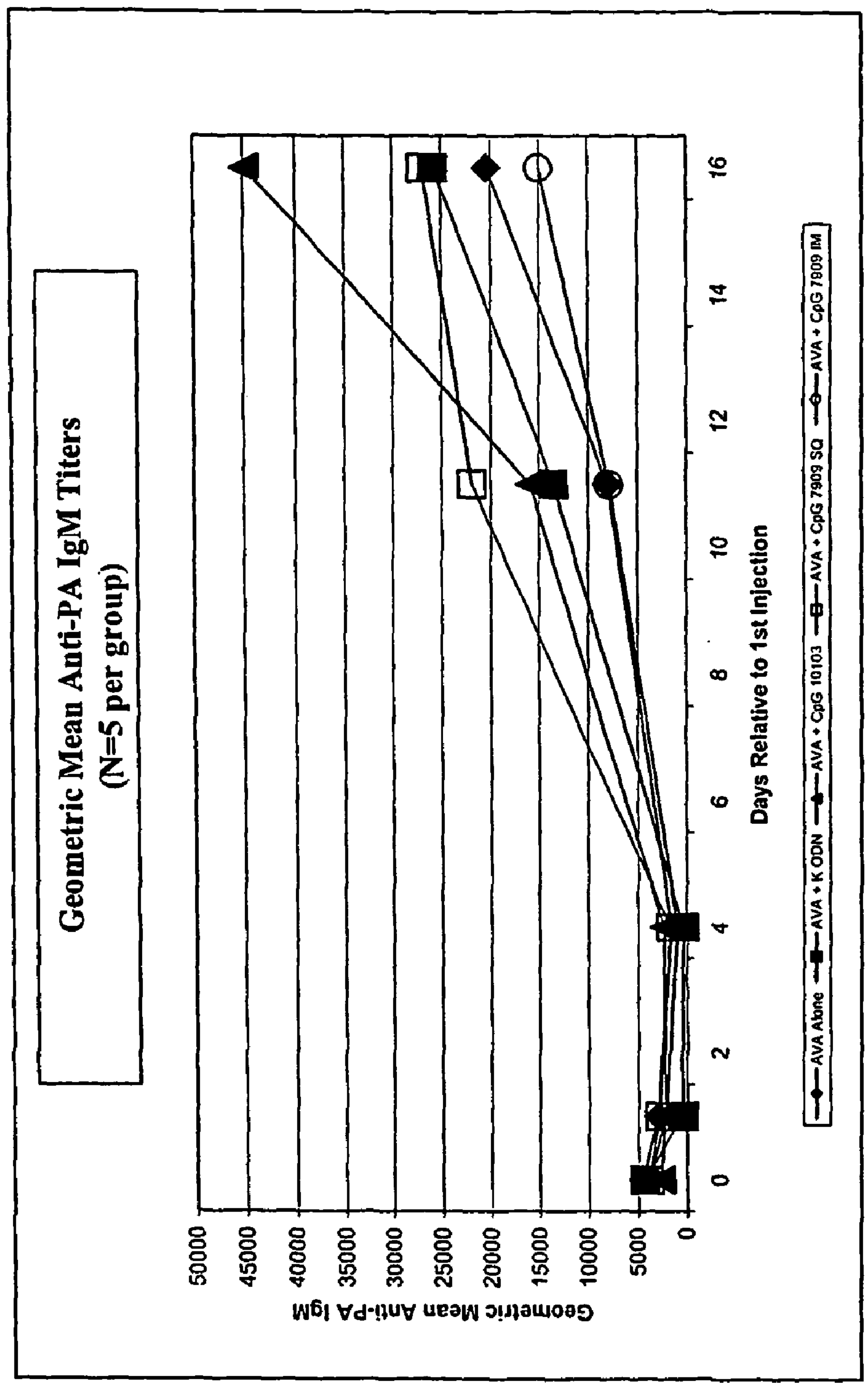

FIG. 7 is a graph of the geometric mean anti-PA IgM titers following treatment with the anthrax vaccine AVA alone, AVA plus K ODN, AVA plus ODN 10103, and AVA plus ODN 7909.

Figure 8:
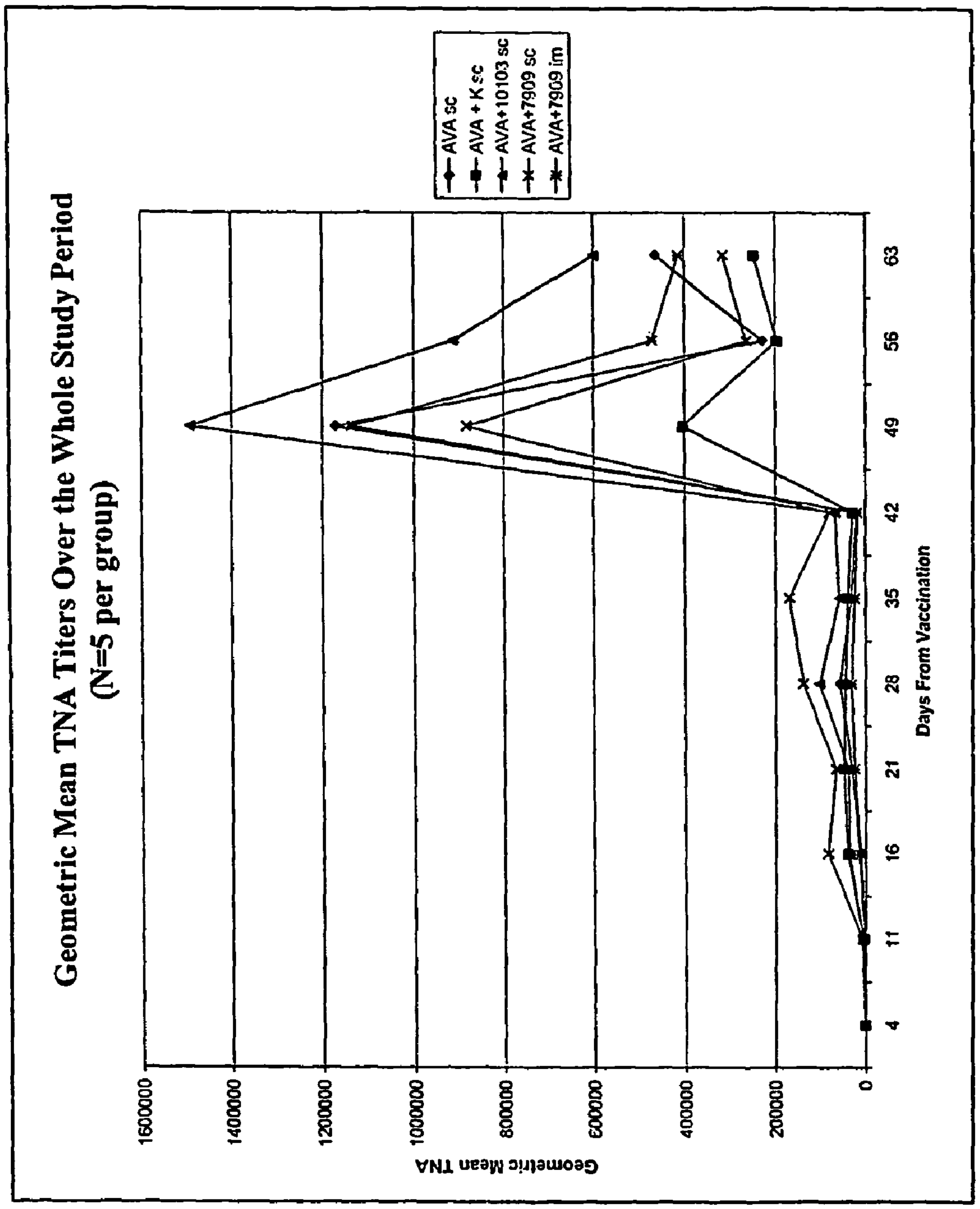

FIG. 8 is line graph of the geometric mean TNA titers over the entire study period following treatment with the anthrax vaccine AVA alone, AVA plus K ODN, AVA plus ODN 10103, and AVA plus ODN 7909.

Figure 9:
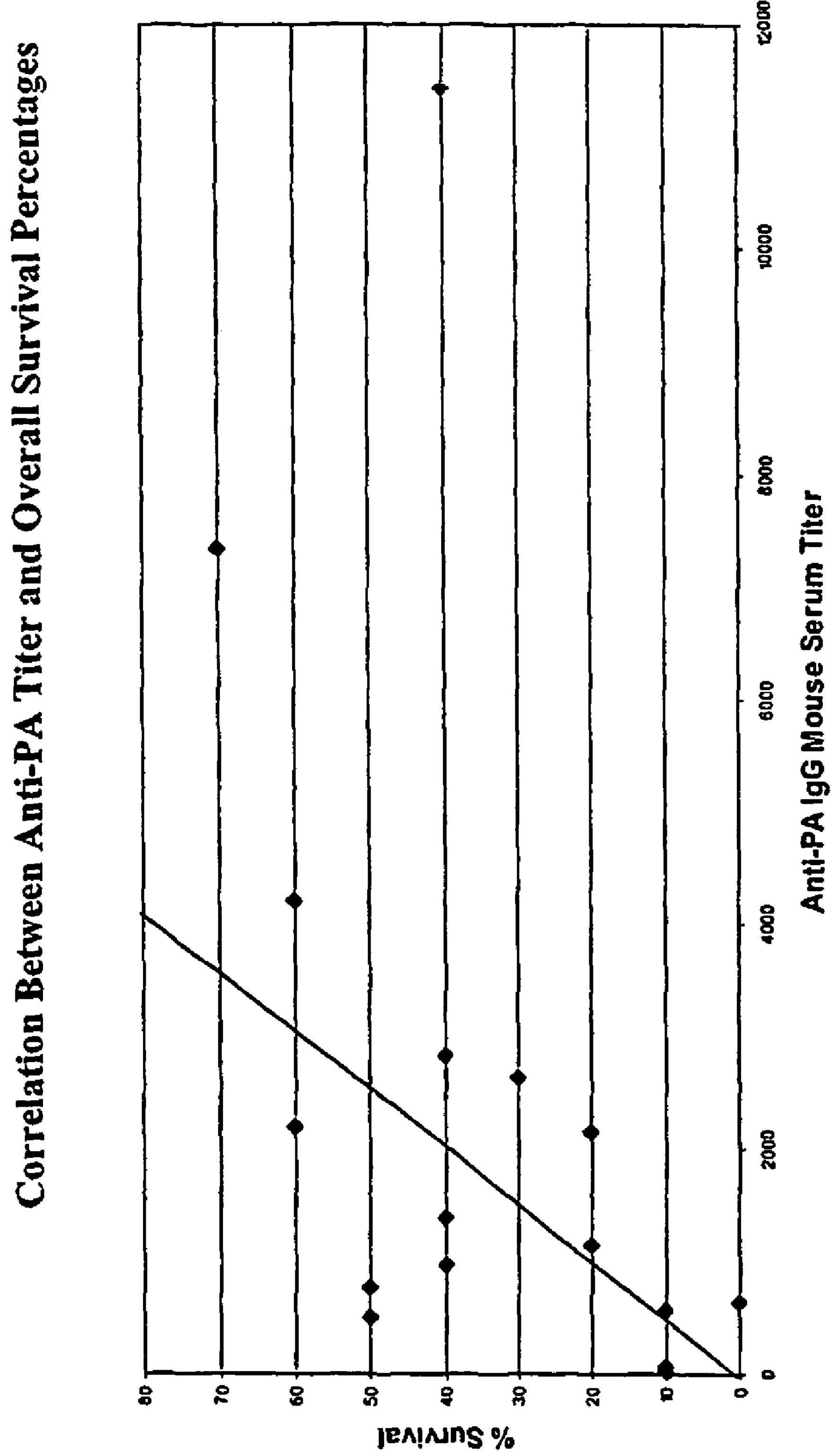

FIG. 9 is a graphical representation of the correlation between anti-PA titer and overall survival percentages.

SEQUENCE LISTING

The nucleic acid sequences listed in the accompanying sequence listing are shown using standard letter abbreviations for nucleotide bases, as defined in 37 C.F.R. 1.822. It will be clear to one of skill in the art that whereas the letter X is used in the specification to refer to any unspecified nucleotide, the letter N is used in the Sequence Listing to refer to any unspecified nucleotide. In the accompanying sequence listing:

SEQ ID NOs 1-16, 17, 18, and 21-25 are immunostimulatory CpG D oligonucleotide sequences.

SEQ ID NOs 19, 20, and 26-28 are control D oligonucleotide sequences.

SEQ ID NOs 29-43 are K oligonucleotide sequences.

DETAILED DESCRIPTION

I. Abbreviations

A: adenine
Ab: antibody
AVA: anthrax vaccine adsorbed
C: cytosine
CpG ODN: an oligodexoynucleotide (either a D or a K type) including a CpG motif
DC: dendritic cell
EU: Endotoxin units
FCS: fetal calf serum
G: guanine
h: hour
IFN-α: interferon alpha
i.m.: intramuscular
i.p.: intraperitoneal
IFN-γ: interferon gamma
μg: microgram
mRNA: messenger ribonucleic acid
NK: natural killer cells
ODN: oligodeoxynucleotide
PA: protective antigen
PAMPs: pathogen-associated molecular patterns
Pu: purine
Py: pyrimidine
rPA: recombinant PA antigen
SQ: subcutaneous
T: thymine
TLR: Toll-like receptor

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects, for example, humans, non-human primates, dogs, cats, horses, and cows.

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term "antigen" includes all related antigenic epitopes. In one embodiment, an antigen is a bioterrorism agent antigen. In some embodiments, an antigen is a component of a vaccine against a bioterrorism agent, which is an antigen associated with or expressed by any bacterium, virus, fungus, or biotoxin that can be dispersed to cause disease or death in animals or humans.

Anti-infectious agent: A substance (such as a chemical compound, protein, antisense oligonucleotide, or other molecule) of use in treating infection of a subject. Anti-infectious agents include, but are not limited to, anti-fungal compounds, anti-viral compounds, and antibiotics. Antibiotics include, but are not limited to, amoxicillin, clarithromycin, cefuroxime, cephalexin ciprofloxacin, doxycycline, metronidazole, terbinafine, levofloxacin, nitrofurantoin, tetracycline, and azithromycin. Anti-fungal compounds, include, but are not limited to, clotrimazole, butenafine, butoconazole, ciclopirox, clioquinol, clioquinol, clotrimazole, econazole, fluconazole, flucytosine, griseofulvin, haloprogin, itraconazole, ketoconazole, miconazole, naftifine, nystatin, oxiconazole, sulconazole, terbinafine, terconazole, fluconazole, and tolnaftate. Anti-viral compounds, include, but are not limited to, zidovudine, didanosine, zalcitabine, stavudine, lamivudine, abacavir, tenofovir, nevirapine, delavirdine, efavirenz, saquinavir, ritonavir, indinavir, nelfinavir, saquinavir, amprenavir, and lopinavir. Anti-infectious agents also include hyper-immune globulin. Hyper-immune globulin is gamma globulin isolated from a donor, or from a pool of donors, that has been immunized with a substance of interest. Specifically, hyper-immune globulin is antibody purified from a donor who was repeatedly vaccinated against a pathogen. In several embodiments, hyper-immune globulin is gamma globulin isolated from a donor, or from a pool of donors, repeatedly immunized with an antigen, a micro-organism (including a heat-killed micro-organism), or a virus. In one specific, non-limiting example, hyper-immune globulin against anthrax is produced using serum from a donor repeatedly immunized with the anthrax vaccine (AVA).

Antisense, Sense and Antigene: Double-stranded DNA (dsDNA) has two strands, a 5'→3' strand, referred to as the plus strand, and a 3'→5' strand (the reverse compliment), referred to as the minus strand. Because RNA polymerase adds nucleic acids in a 5'→3' direction, the minus strand of the DNA serves as the template for the RNA during transcription. Thus, the RNA formed will have a sequence complementary to the minus strand and identical to the plus strand (except that U is substituted for T).

Antisense molecules are molecules that are specifically hybridizable or specifically complementary to either RNA or the plus strand of DNA. Sense molecules are molecules that are specifically hybridizable or specifically complementary to the minus strand of DNA. Antigene molecules are either antisense or sense molecules directed to a dsDNA target. In one embodiment, an antisense molecule specifically hybridizes to a target mRNA and inhibits transcription of the target mRNA.

AVA: The only licensed human anthrax vaccine in the United States, AVA, is produced by BioPort Corporation in Lansing, Mich., and is prepared from a cell-free filtrate of *B. anthracis* culture that contains no dead or live bacteria. The strain used to prepare the vaccine is a toxigenic, nonencapsulated strain known as V770-NP1-R. The filtrate contains a mix of cellular products including PA (protective antigen) and is adsorbed to aluminum hydroxide (Amphogel, Wyeth Laboratories) as adjuvant. The amount of PA and other proteins per 0.5 mL dose is unknown, and all three toxin components, LF (lethal factor), EF (edema factor), and PA, are present in the product.

Generally, primary vaccination generally consists of three subcutaneous injections at 0, 2, and 4 weeks, and three booster vaccinations at 6, 12, and 18 months. To maintain immunity, the manufacturer recommends an annual booster injection. However, schedules with a reduced number of doses and with intramuscular (IM) administration have been proposed. Following a suspected exposure to *B. anthracis*, AVA may be given concurrently with antibiotic prophylaxis.

*Bacillus Anthracis*: The etiologic agent of anthrax, *Bacillus anthracis* is a large, gram-positive, nonmotile, spore-forming bacterial rod. The three virulence factors of *B. anthracis* are edema toxin, lethal toxin and a capsular antigen. Infection with *B. anthracis* is the cause of human anthrax disease. Human anthrax has three major clinical forms: cutaneous, inhalation, and gastrointestinal. Cutaneous anthrax is a result of introduction of the spore through the skin; inhalation anthrax, through the respiratory tract; and gastrointestinal anthrax, by ingestion. If untreated, anthrax in all forms can lead to septicemia and death. Early treatment of cutaneous anthrax is usually curative, and early treatment of all forms is important for recovery. Patients with gastrointestinal anthrax have reported case-fatality rates ranging from 25% to 75%. Case-fatality rates for inhalational anthrax are thought to approach 90 to 100%.

*Bacillus anthracis* secretes a toxin made up of three proteins: protective antigen (PA), oedema factor (OF) and lethal factor (LF) (Stanley et al., *J. Gen. Microbiol.* 26:49-66, 1961; Beall et al., *J. Bacteriol.* 83:1274-1280, 1962). PA binds to cell-surface receptors on the host's cell membranes. After being cleaved by a protease (Bradley et al., *Nature* 414:225, 2001), PA binds to the two toxic enzymes, OF and LA, and mediates their transportation into the cytosol where they exert their pathogenic effects. Thus, the smaller cleaved 63 kD PA remnant $PA_{63}$) oligomerizes features a newly exposed, second binding domain and binds to either EF, an 89 kD protein, to form edema toxin, or LF, a 90 kD protein, to form lethal toxin (LeTx) (Leppla et al., *Salisbury Med. Bull. Suppl.* 68:41-43, 1990), and the complex is internalized into the cell (Singh et al., *Infect. Immun.* 67:1853, 1999; Friedlander, *J. Biol. Chem.* 261:7123, 1986). From these endosomes, the $PA_{63}$ channel enables translocation of LF and EF to the cytosol by a pH- and voltage-dependent mechanism (Zhao et al., *J. Biol. Chem,* 270:18626, 1995).

Bioterrorism agents: Any of various bacteria, viruses, and toxins that can be dispersed deliberately to cause disease or death to humans or animals. Examples of bioterrorism agents include *Bacillus anthracis*, which causes anthrax, *Yersinia pestis*, which causes plague, and *Variola major*, which causes smallpox, tick-borne encephalitis virus (TBEV), which causes tick-borne encephalitis, and Ebola virus, which causes Ebola. Bioterrorism agents also include biotoxins, which are toxins produced by certain biological organisms. Exemplary biotoxins are botulinum toxin, produced by the bacterium *Clostridium botulinum*, and ricin isolated from castor oil seeds. Western counter-proliferation agencies currently recognize 23 types of bacteria, 43 types of viruses, and 14 types of biotoxins as potential bioterrorism agents.

Other examples of bioterrorism agents include, but are not limited to, *Escherichia coli, Haemophilus influenzae*, cobra venom, shellfish toxin, botulinum toxin, saxitoxin, ricin toxin, *Shigella flexneri, S. dysenteriae* (*Shigella bacillus*), *Salmonella, Staphylococcus* enterotoxin B, *Histoplasma capsulatum*, tricothecene mycotoxin, aflatoxin. Bioterrorism agents can also result in cryptococcosis, brucellosis (undulant fever), coccidioidomycosis (San Joaquin Valley or desert fever), psittacosis (parrot fever), bubonic plague, tularemia (rabbit fever), malaria, cholera, typhoid, hemorrhagic fever, tick-borne encephalitis, Venezuelan equine encephalitis, pneumonic plague, Rocky Mountain spotted fever, dengue fever, Rift Valley fever, diphtheria, melioidosis, glanders, tuberculosis, infectious hepatitis, encephalitides, blastomycosis, nocardiosis, yellow fever, typhus, and Q fever.

CpG or CpG motif: A nucleic acid having a cytosine followed by a guanine linked by a phosphate bond in which the pyrimidine ring of the cytosine is unmethylated. The term "methylated CpG" refers to the methylation of the cytosine on the pyrimidine ring, usually occurring at the 5-position of the pyrimidine ring. A CpG motif is a pattern of bases that include an unmethylated central CpG surrounded by at least one base flanking (on the 3' and the 5' side of) the central CpG. Without being bound by theory, the bases flanking the CpG confer part of the activity to the CpG oligodeoxynucleotide. A CpG oligonucleotide is an oligonucleotide that is at least about ten nucleotides in length and includes an unmethylated CpG. CpG oligonucleotides include both D and K oligodeoxynucleotides (see below). CpG oligodeoxynucleotides are single-stranded. The entire CpG oligodeoxynucleotide can be unmethylated or portions may be unmethylated. In one embodiment, at least the C of the 5' CG 3' is unmethylated.

Cytokine: Proteins made by cells that affect the behavior of other cells, such as lymphocytes. In one embodiment, a cytokine is a chemokine, a molecule that affects cellular trafficking. Specific non-limiting examples of cytokines are IFN-γ, IL-6, and IL-10.

D Type Oligodeoxynucleotide (D ODN): An oligodeoxynucleotide including an unmethylated CpG motif that has a sequence represented by the formula:

5'RY-CpG-RY3' wherein the central CpG motif is unmethylated, R is A or G (a purine), and Y is C or T (a pyrimidine). D-type oligodeoxynucleotides include an unmethylated CpG dinucleotide. Inversion, replacement or methylation of the CpG reduces or abrogates the activity of the D oligodeoxynucleotide.

In one embodiment, a D type ODN is at least about 16 nucleotides in length and includes a sequence represented by Formula III:

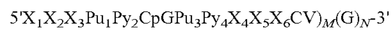

$$5'X_1X_2X_3Pu_1Py_2CpGPu_3Py_4X_4X_5X_6CV)_M(G)_N\text{-}3'$$

wherein the central CpG motif is unmethylated, Pu is a purine nucleotide, Py is a pyrimidine nucleotide, X and W are any nucleotide, M is any integer from 0 to 10, and N is any integer from 4 to 10. Generally D ODNs can stimulate a cellular response. For example, D ODNs stimulate natural killer cells and the maturation of dendritic cells.

Epitope: An antigenic determinant. These are particular chemical groups or peptide sequences on a molecule that are antigenic, i.e., that elicit a specific immune response. An antibody binds a particular antigenic epitope.

Functionally Equivalent: Sequence alterations, for example in an immunostimulatory ODN, that yield the same results as described herein. Such sequence alterations can include, but are not limited to, deletions, base modifications, mutations, labeling, and insertions.

Immune response: A response of a cell of the immune system, such as a B cell or a T cell, to a stimulus. In one embodiment, the response is specific for a particular antigen (an "antigen-specific response"). A "parameter of an immune response" is any particular measurable aspect of an immune response, including, but not limited to, cytokine secretion (IL-6, IL-10, IFN-γ, etc.), immunoglobulin production, dendritic cell maturation, and proliferation of a cell of the immune system. One of skill in the art can readily determine an increase in any one of these parameters, using known laboratory assays. In one specific non-limiting example, to assess cell proliferation, incorporation of $^3$H-thymidine can be assessed. A "substantial" increase in a parameter of the immune response is a significant increase in this parameter as compared to a control. Specific, non-limiting examples of a substantial increase are at least about a 50% increase, at least about a 75% increase, at least about a 90% increase, at least about a 100% increase, at least about a 200% increase, at least about a 300% increase, and at least about a 500% increase. One of skill in the art can readily identify a significant increase using known statistical methods. One specific, non-limiting example of a statistical test used to assess a substantial increase is the use of a Z test to compare the percent of samples that respond to a vaccine against a bioterrorism agent alone as compared to the percent of samples that respond using a vaccine against a bioterrorism agent administered in conjunction with an immunostimulatory ODN. A non-parametric ANOVA can be used to compare differences in the magnitude of the response induced by vaccine alone as compared to the percent of samples that respond using vaccine administered in conjunction with an immunostimulatory ODN. In this example, $p \leqq 0.05$ is significant, and indicates a substantial increase in the parameter of the immune response. One of skill in the art can readily identify other statistical assays of use.

An "immunoprotective response" is an immune response that results in a decrease of symptoms upon infection with a bioterrorism agent or results in a delay or prevention of a disease associated with infection. "Enhancing the immunogenicity of a vaccine" is an example of an increase in an immune response.

Inhibiting or treating a disease: "Inhibiting" a disease refers to reducing the full development of a disease, for example in a person who is known to have a predisposition to a disease such as a person who has been or is at risk for being exposed to a bioterrorism agent. Examples of persons at risk for being exposed to a bioterrorism agent include, but are not limited to, military personnel, mail handlers, medical personnel, and governmental officials, as well as those with weakened immune systems, for example, the elderly, people on immunosuppressive drugs, subjects with cancer, and subjects infected with HIV. "Treatment" refers to a therapeutic intervention that ameliorates a sign or symptom of a disease or pathological condition after it has begun to develop.

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

K Type Oligodeoxynucleotide (K ODN): An oligodeoxynucleotide including an unmethylated CpG motif that has a sequence represented by the formula:

$$5'N_1N_2N_3Q\text{-}CpG\text{-}WN_4N_5N_63'$$

wherein the central CpG motif is unmethylated, Q is T, G or A, W is A or T, and $N_1$, $N_2$, $N_3$, $N_4$, $N_5$, and $N_6$ are any nucleotides. In one embodiment, Q is a T. K type CpG ODNs have been previously described (see U.S. Pat. No. 6,194,388; U.S. Pat. No. 6,207,646; U.S. Pat. No. 6,214,806; U.S. Pat.

No. 6,218,371; U.S. Pat. No. 6,239,116, U.S. Pat. No. 6,339,068; U.S. Pat. No. 6,406,705 and U.S. Pat. No. 6,429,199, which are herein incorporated by reference). Generally K ODNs can stimulate a humoral response. For example, K ODNs stimulate the production of IgM.

Leukocyte: Cells in the blood, also termed "white cells," that are involved in defending the body against infective organisms and foreign substances. Leukocytes are produced in the bone marrow. There are 5 main types of white blood cell, subdivided between 2 main groups: polymorphomnuclear leukocytes (neutrophils, eosinophils, basophils) and mononuclear leukocytes (monocytes and lymphocytes). When an infection is present, the production of leukocytes increases.

Mammal: This term includes both human and non-human mammals. Similarly, the term "subject" includes both human and veterinary subjects.

Nucleic acid: A deoxyribonucleotide or ribonucleotide polymer in either single or double stranded form, and unless otherwise limited, encompasses known analogues of natural nucleotides that hybridize to nucleic acids in a manner similar to naturally occurring nucleotides.

Oligonucleotide or "oligo": Multiple nucleotides (i.e. molecules comprising a sugar (e.g. ribose or deoxyribose) linked to a phosphate group and to an exchangeable organic base, which is either a substituted pyrimidine (Py) (e.g. cytosine (C), thymine (T) or uracil (U)) or a substituted purine (Pu) (e.g. adenine (A) or guanine (G)). The term "oligonucleotide" as used herein refers to both oligoribonucleotides (ORNs) and oligodeoxyribonucleotides (ODNs). The term "oligonucleotide" also includes oligonucleosides (i.e. an oligonucleotide minus the phosphate) and any other organic base polymer. Oligonucleotides can be obtained from existing nucleic acid sources (e.g. genomic or cDNA), but are preferably synthetic (e.g. produced by oligonucleotide synthesis).

A "stabilized oligonucleotide" is an oligonucleotide that is relatively resistant to in vivo degradation (for example via an exo- or endo-nuclease). In one embodiment, a stabilized oligonucleotide has a modified phosphate backbone. One specific, non-limiting example of a stabilized oligonucleotide has a phosphorothioate modified phosphate backbone (wherein at least one of the phosphate oxygens is replaced by sulfur). Other stabilized oligonucleotides include: nonionic DNA analogs, such as alkyl- and aryl-phosphonates (in which the charged phosphonate oxygen is replaced by an alkyl or aryl group), phosphodiester and alkylphosphotriesters, in which the charged oxygen moiety is alkylated. Oligonucleotides which contain a diol, such as tetraethyleneglycol or hexaethyleneglycol, at either or both termini have also been shown to be substantially resistant to nuclease degradation.

An "immunostimulatory oligonucleotide," "immunostimulatory CpG containing oligodeoxynucleotide," "CpG ODN," refers to an oligodeoxynucleotide, which contains a cytosine, guanine dinucleotide sequence and stimulates (e.g. has a mitogenic effect) vertebrate immune cells. The cytosine, guanine is unmethylated. The term "immunostimulatory ODN" includes both D and K type ODNs.

An "oligonucleotide delivery complex" is an oligonucleotide associated with (e.g. ionically or covalently bound to; or encapsulated within) a targeting means (e.g. a molecule that results in a higher affinity binding to a target cell (e.g. B cell or natural killer (NK) cell) surface and/or increased cellular uptake by target cells). Examples of oligonucleotide delivery complexes include oligonucleotides associated with: a sterol (e.g. cholesterol), a lipid (e.g. cationic lipid, virosome or liposome), or a target cell specific binding agent (e.g. a ligand recognized by a target cell specific receptor). Preferred complexes must be sufficiently stable in vivo to prevent significant uncoupling prior to internalization by the target cell. However, the complex should be cleavable or otherwise accessible under appropriate conditions within the cell so that the oligonucleotide is functional. (Gursel, *J. Immunol.* 167: 3324, 2001)

Protective Antigen (PA): *Bacillus anthracis* secretes a toxin made up of three proteins: protective antigen (PA), edema factor (EF) and lethal factor (LF). PA binds to cell-surface receptors on the host's cell membranes. After being cleaved by a protease, PA binds to the two toxic enzymes, EF and LA, and mediates their transportation into the cytosol where they exert their pathogenic effects.

The only licensed human anthrax vaccine in the United States, AVA, contains a mix of cellular products including PA (protective antigen). The sequence of the protection antigen is known, as is set forth as GenBank Accession No. 13423, which is incorporated herein by reference. Vaccine preparations including PA are described, for example, in U.S. Pat. No. 5,591,631, which is incorporated herein by reference. Recombinant Protective Antigen (rPA) is an anthrax vaccine that is currently under development. rPA is a recombinant version of the PA vaccine.

Pharmaceutical agent or drug: A chemical compound or composition capable of inducing a desired therapeutic or prophylactic effect when properly administered to a subject. Pharmaceutical agents include, but are not limited to, anti-infective agents, such as antibiotics, anti-fungal compounds, anti-viral compounds, and hyper-immune globulin.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of the fusion proteins herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Self-complementary nucleic acid sequence: A nucleic acid sequence that can form Watson-Crick base pairs. The four bases characteristic of deoxyribonucleic unit of DNA are the purines (adenine and guanine) and the pyrimidines (cytosine and thymine). Adenine pairs with thymine via two hydrogen bonds, while guanine pairs with cytosine via three hydrogen bonds. If a nucleic acid sequence includes two or more bases in sequence that can form hydrogen bonds with two or more other bases in the same nucleic acid sequence, then the nucleic acid includes a self-complementary sequence.

Therapeutically effective dose: A dose sufficient to prevent advancement, or to cause regression of the disease, or which is capable of relieving symptoms caused by the disease, such as fever, respiratory symptoms, pain or swelling.

Vaccine: A preparation of antigen, DNA, protein subunit, peptide, attenuated microorganisms (including but not limited to bacteria and viruses), living microorganisms, or killed microorganisms, administered for the inhibition, prevention, amelioration or treatment of infectious disease. In some embodiments, the vaccine against a bioterrorism agent includes an antigen from a bioterrorism agent, for example AVA or PA.

Generally, the first step in making a vaccine is to isolate or create an organism, or part of one, that is unable to cause the disease, but that still retains the antigens responsible for inducing the host's immune response. This can be done in many ways. One way is to kill the organism using heat or formalin; vaccines produced in this way are called "inactivated" or "killed" vaccines. Examples of killed vaccines in common use today are the typhoid vaccine and the Salk poliomyelitis vaccine.

Another way to produce a vaccine is to use only the antigenic part of the disease-causing organism, for example the capsule, the flagella, or part of the protein cell wall; these types of vaccines are called "acellular vaccines." An example of an acellular vaccine is the *Haemophilus influenzae* B (HIB) vaccine. Acellular vaccines exhibit some similarities to killed vaccines: neither killed nor acellular vaccines generally induce the strongest immune responses and may therefore require a "booster" every few years to insure their continued effectiveness. In addition, neither killed nor acellular vaccines can cause disease and are therefore considered to be safe for use in immunocompromised patients.

A third way of making a vaccine is to "attenuate" or weaken a live microorganism by mutating the organism to alter its growth capabilities. In one embodiment, an attenuated vaccine is not replication competent or lacks essential proteins. Examples of attenuated vaccines are those that protect against measles, mumps, and rubella. Immunity is often life-long with attenuated vaccines and does not require booster shots.

Vaccines can also be produced from a toxin. In these cases, the toxin is often treated with aluminum or adsorbed onto aluminum salts to form a "toxoid." Examples of toxoids are the diphtheria and the tetanus vaccines. Vaccines made from toxoids often induce low-level immune responses and are therefore sometimes administered with an "adjuvant"—an agent which increases the immune response. For example, the diphtheria and tetanus vaccines are often combined with the pertussis vaccine and administered together as a DPT immunization. The pertussis acts as an adjuvant in this vaccine. When more than one vaccine is administered together it is called a "conjugated vaccine."

Another way of making a vaccine is to use an organism which is similar to the virulent organism but that does not cause serious disease, such as using the cowpox virus to protect against infection with smallpox virus, or BCG vaccine, an attenuated strain of *Mycobacterium bovis*, used to protect against *Mycobacterium tuberculosis.*

"Subunit vaccines" are vaccines which use a polypeptide from an infectious organism to stimulate a strong immune response. An "antigen vaccine" uses an immunogenic epitope of a polypeptide to induce a protective immune response. A "DNA vaccine" uses a nucleic acid encoding an antigen to induce a protective immune response.

A "vaccine against a bioterrorism agent" can be, but is not limited to, a heat or formalin-killed vaccine, attenuated vaccine, subunit vaccine, antigen vaccine, DNA vaccine, acellular vaccine, or toxoid vaccine directed against *Bacillus anthracis, Yersinia pestis, Variola major*, tick-borne encephalitis virus (TBEV), Ebola virus, *Escherichia coli, Haemophilus influenzae*, cobra venom, shellfish toxin, botulinum toxin, saxitoxin, ricin toxin, *Shigella flexneri, S. dysenteriae* (*Shigella bacillus*), *Salmonella, Staphylococcus* enterotoxin B, *Histoplasma capsulatum*, tricothecene mycotoxin, aflatoxin. A "vaccine against a bioterrorism agent" can also be used to induce a protective immune response against cryptococcosis, brucellosis (undulant fever), coccidioidomycosis (San Joaquin Valley or desert fever), psittacosis (parrot fever), bubonic plague, tularemia (rabbit fever), malaria, cholera, typhoid, hemorrhagic fever, tick-borne encephalitis, Venezuelan equine encephalitis, pneumonic plague, Rocky Mountain spotted fever, dengue fever, Rift Valley fever, diphtheria, melioidosis, glanders, tuberculosis, infectious hepatitis, encephalitides, blastomycosis, nocardiosis, yellow fever, typhus, and Q fever.

Virus: A microscopic infectious organism that reproduces inside living cells. A virus consists essentially of a core of a single nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Description of Several Embodiments

A. D and K-Type ODNs

The present disclosure relates to a class of DNA motifs that stimulates immune activation, for example the innate immune response or the adaptive immune response by B cells, monocytes, dendritic cells, and natural killer (NK) cells. K type CpG ODNs have been previously described (see U.S. Pat. No. 6,194,388; U.S. Pat. No. 6,207,646; U.S. Pat. No. 6,214,806; U.S. Pat. No. 6,218,371; U.S. Pat. No. 6,239,116, U.S. Pat. No. 6,339,068; U.S. Pat. No. 6,406,705 and U.S. Pat. No. 6,429,199, which are herein incorporated by reference). K ODNs that exhibit the greatest immunostimulatory activity share specific characteristics. These characteristics differ from those of the Formula II or D ODN (see below). In addition, K ODNs have specific effects on the cells of the immune system, which differ from the effects of D ODN. For example, K ODNs stimulate proliferation of B cells and stimulate the production of IL-6.

The K ODNs include at least about 10 nucleotides and include a sequence represented by Formula I:

$$5'N_1N_2N_3T\text{-}CpG\text{-}WN_4N_5N_63'$$

wherein the central CpG motif is unmethylated, W is A or T, and $N_1$, $N_2$, $N_3$, $N_4$, $N_5$, and $N_6$ are any nucleotides.

These Formula I or K ODNs stimulate B cell proliferation and the secretion of IgM and IL-6, processes involved in the body's humoral immunity, such as the production of antibodies against foreign antigens. In one embodiment, the K ODNs induce a humoral immune response.

Certain K oligonucleotides are of the formula:

$5'N_1N_2N_3T\text{-CpG-}WN_4N_5N_63'$ contain a phosphate backbone modification. In one specific, non-limiting example, the phosphate backbone modification is a phosphorothioate backbone modification (i.e., one of the non-bridging oxygens is replaced with sulfur, as set forth in International Patent Application WO 95/26204, herein incorporated by reference). In one embodiment, K ODNs halve a phosphorothioate backbone, and at least one unmethylated CpG dinucleotide. Eliminating the CpG dinucleotide motif from the K ODN significantly reduces immune activation. Incorporating multiple CpGs in a single K ODN increases immune stimulation. In some embodiments, the K ODNs are at least 12 bases long. In addition, K ODNs containing CpG motifs at the 5' end are the most stimulatory, although at least one base upstream of the CpG is required. More particularly, the most active K ODNs contain a thymidine immediately 5' from the CpG dinucleotide, and a TpT or a TpA in a position 3' from the CpG motif. Modifications which are greater than 2 base pairs from the CpG dinucleotide motif appear to have little effect on K ODN activity.

Examples of a K ODN include, but are not limited to:

```
TCCATGTCGCTCCTGATGCT        (SEQ ID NO: 29)
TCCATGTCGTTCCTGATGCT        (SEQ ID NO: 30)
TCGTCGTTTTGTCGTTTTGTCGT     (SEQ ID NO: 31)
TCGTCGTTGTCGTTGTCGTT        (SEQ ID NO: 32)
TCGTCGTTTTGTCGTTTGTCGTT     (SEQ ID NO: 33)
TCGTCGTTGTCGTTTTGTCGTT      (SEQ ID NO: 34)
GCGTGCGTTGTCGTTGTCGTT       (SEQ ID NO: 35)
TGTCGTTTGTCGTTTGTCGTT       (SEQ ID NO: 36)
TGTCGTTGTCGTTGTCGTT         (SEQ ID NO: 37)
TCGTCGTCGTCGTT              (SEQ ID NO: 38)
TCCTGTCGTTCCTTGTCGTT        (SEQ ID NO: 39)
TCCTGTCGTTTTTTGTCGTT        (SEQ ID NO: 40)
TCGTCGCTGTCTGCCCTTCTT       (SEQ ID NO: 41)
TCGTCGCTGTTGTCGTTTCTT       (SEQ ID NO: 42)
TCCATGACGTTCCTGACGTT        (SEQ ID NO: 43)
```

In particular, non-limiting examples, the K oligodeoxynucleotide includes a sequence selected from the group consisting of SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID) NO: 42, and SEQ ID NO: 43.

D ODNs differ both in structure and activity from K ODNs. The unique activities of D ODNs are disclosed below. For example, as disclosed herein, D oligodeoxynucleotides stimulate the release of cytokines from cells of the immune system. In specific, non-limiting examples, D oligonucleotides stimulate the release or production of IP-10 and IFN-$\alpha$ by monocytes and/or plasmacytoid dendritic cells and the release or production of IFN-$\gamma$ by NK cells. The stimulation of NK cells by D oligodeoxynucleotides can be either direct or indirect.

With regard to structure, a CpG motif in D oligonucleotides can be described by Formula II:

5'RY-CpG-RY3' wherein the central CpG motif is unmethylated, R is A or G (a purine), and Y is C or T (a pyrimidine). D oligonucleotides include an unmethylated CpG dinucleotide. Inversion, replacement or methylation of the CpG reduces or abrogates the activity of the D oligonucleotide.

Certain D ODNs are at least about 16 nucleotides in length and includes a sequence represented by Formula III:

$5'X_1X_2X_3Pu_1Py_2CpG\ Pu_3Py_4X_4X_5X_6(W)_M(G)_N\text{-}3'$ wherein the central CpG motif is unmethylated, Pu is a purine nucleotide, Py is a pyrimidine nucleotide, X and W are any nucleotide, M is any integer from 0 to 10, and N is any integer from 4 to 10.

The region $Pu_1$ $Py_2$ CpG $Pu_3$ $Py_4$ is termed the CpG motif. The region $X_1X_2X_3$ is termed the 5' flanking region, and the region $X_4X_5X_6$ is termed the 3' flanking region. If nucleotides are included 5' of $X_1X_2X_3$ in the D ODN, these nucleotides are termed the 5' far flanking region. Nucleotides 3' of $X_4X_5X_6$ in the D ODN are termed the 3' far flanking region.

In one specific, non-limiting example, $Py_2$ is a cytosine. In another specific, non-limiting example, $Pu_3$ is a guanidine. In yet another specific, non-limiting example, $Py_2$ is a thymidine and $Pu_3$ is an adenine. In a further specific, non-limiting example, $Pu_1$ is an adenine and $Py_2$ is a tyrosine. In another specific, non-limiting example, $Pu_3$ is an adenine and $Py_4$ is a tyrosine.

In one specific, not limiting example, N is from about 4 to about 8. In another specific, non-limiting example, N is about 6.

D CpG oligonucleotides can include modified nucleotides. Without being bound by theory, modified nucleotides can be included to increase the stability of a D oligonucleotide. Without being bound by theory, because phosphorothioate-modified nucleotides confer resistance to exonuclease digestion, the D ODN are "stabilized" by incorporating phosphorothioate-modified nucleotides. In one embodiment, the CpG dinucleotide motif and its immediate flanking regions include phosphodiester rather than phosphorothioate nucleotides. In one specific non-limiting example, the sequence $Pu_1$ $Py_2$ CpG $Pu_3$ $Py_4$ includes phosphodiester bases. In another specific, non-limiting example, all of the bases in the sequence $Pu_1$ $Py_2$ CpG $Pu_3$ $Py_4$ are phosphodiester bases. In yet another specific, non-limiting example, $X_1X_2X_3$ and $X_4X_5X_6(W)_M$ $(G)_N$ include phosphodiester bases. In yet another specific, non-limiting example, $X_1X_2X_3$ $Pu_1$ $Py_2$ CpG $Pu_3$ $Py_4$ $X_4X_5X_6$ $(W)_M$ $(G)_N$ include phosphodiester bases. In further non-limiting examples, the sequence $X_1X_2X_3$ includes at most one or at most two phosphothioate bases and/or the sequence $X_4X_5X_6$ includes at most one or at most two phosphotioate bases. In additional non-limiting examples, $X_4X_5X_6(W)_M$ $(G)_N$ includes at least 1, at least 2, at least 3, at least 4, or at least 5 phosphothioate bases. Thus, a D oligodeoxynucleotide can be a phosphorothioate/phosphodiester chimera.

As disclosed herein, any suitable modification can be used in the present disclosure to render the D oligodeoxynucleotide resistant to degradation in vivo (e.g., via an exo- or endo-nuclease). In one specific, non-limiting example, a modification that renders the oligodeoxynucleotide less susceptible to degradation is the inclusion of nontraditional bases such as inosine and quesine, as well as acetyl-, thio- and similarly modified forms of adenine, cytidine, guanine, thymine, and uridine. Other modified nucleotides include nonionic DNA analogs, such as alkyl or aryl phosphonates (i.e., the charged phosphonate oxygen is replaced with an alkyl or aryl group, as set forth in U.S. Pat. No. 4,469,863), phosphodiesters and alkylphosphotriesters (i.e., the charged oxygen moiety is alkylated, as set forth in U.S. Pat. No. 5,023,243 and European Patent No. 0 092 574). Oligonucleotides containing a diol, such as tetraethyleneglycol or hexaethyleneglycol, at either or both termini, have also been shown to be more resistant to degradation. The D oligodeoxynucleotides can also be modified to contain a secondary structure (e.g., stem loop structure). Without being bound by theory, it is believed that incorporation of a stem loop structure renders and oligodeoxynucleotide more effective.

In a further embodiment, $Pu_1$ $Py_2$ and $Pu_3$ $Py_4$ are self-complementary. In another embodiment, $X_1X_2X_3$ and $X_4X_5X_6$ are self complementary. In yet another embodiment $X_1X_2X_3$ $Pu_1$ $Py_2$ and $Pu_3$ $Py_4$ $X_4X_5X_6$ are self complementary.

Specific non-limiting examples of a D oligonucleotide wherein $Pu_1$ $Py_2$ and $Pu_3$ $Py_4$ are self-complementary include, but are not limited to, ATCGAT (SEQ ID NO: 9), ACCGGT (SEQ ID NO: 10), ATCGAC (SEQ ID NO: 11), ACCGAT (SEQ ID NO: 12), GTCGAC (SEQ ID NO: 13), or GCCGGC (SEQ ID NO: 14). Without being bound by theory, the self-complementary base sequences can help to form a stem-loop structure with the CpG dinucleotide at the apex to facilitate immunostimulatory functions. Thus, in one specific, non-limiting example, D oligonucleotides wherein $Pu_1$ $Py_2$ and $Pu_3$ $Py_4$ are self-complementary induce higher levels of IFN-γ production from a cell of the immune system (see below). The self-complementary need not be limited to $Pu_1$ $Py_2$ and $Pu_3$ $Py_4$. Thus, in another embodiment, additional bases on each side of the three bases on each side of the CpG-containing hexamer form a self-complementary sequence (see above).

One specific non-limiting example of a sequence wherein $Pu_1$ $Py_2$ and $Pu_3$ $Py_4$ are self-complementary but wherein the far-flank-ing sequences are not self-complementary is:

```
GGTGCATCGATACAGGGGGG.   (ODN D 113, SEQ ID NO: 15)
```

This oligodeoxynucleotide has a far flanking region that is not self-complementary and induces high levels of IFN-γ and IFN-α.

Another specific, non-limiting example of a D oligodeoxynucleotides is:

```
GGTGCGTCGATGCAGGGGGG.    (D28, SEQ ID NO: 16)
```

This oligodeoxynucleotide is of use for inducing production and/or release of cytokines from immune cells, although it lacks a self-complementary motif.

In one embodiment, the D oligodeoxynucleotides disclosed herein are at least about 16 nucleotides in length. In a second embodiment, a D oligodeoxynucleotide is at least about 18 nucleotides in length. In another embodiment, a D oligodeoxynucleotide is from about 16 nucleotides in length to about 100 nucleotides in length. In yet another embodiment, a D oligodexoynucleotide is from about 16 nucleotides in length to about 50 nucleotides in length. In a further embodiment, a D oligodeoxynucleotide is from about 18 nucleotides in length to about 30 nucleotides in length.

In another embodiment, the oligodeoxynucleotide is at least 18 nucleotides in length, and at least two G's are included at the 5' end of the molecule, such that the oligodeoxynucleotide includes a sequence represented by Formula IV:

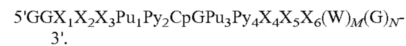

$$5'GGX_1X_2X_3Pu_1Py_2CpGPu_3Py_4X_4X_5X_6(W)_M(G)_N\text{-}3'.$$

The D oligodeoxynucleotide can include additional G's at the 5' end of the oligodeoxynucleotide. In one specific example, about 1 or about 2 G's are included at the 5' end of an olgiodeoxynucleotide including a sequence as set forth as Formula IV.

Examples of a D oligodeoxynucleotide include, but are not limited to:

```
5'XXTGCATCGATGCAGGGGGG3',     (SEQ ID NO: 1)
5'XXTGCACCGGTGCAGGGGGG3',     (SEQ ID NO: 2)
5'XXTGCGTCGACGCAGGGGGG3',     (SEQ ID NO: 3)
5'XXTGCGTCGATGCAGGGGGG3',     (SEQ ID NO: 4)
5'XXTGCGCCGGCGCAGGGGGG3',     (SEQ ID NO: 5)
5'XXTGCGCCGATGCAGGGGGG3',     (SEQ ID NO: 6)
5'XXTGCATCGACGCAGGGGGG3',     (SEQ ID NO: 7)
5'XXTGCGTCGGTGCAGGGGGG3',     (SEQ ID NO: 8)
```

wherein X is any base, or is no base at all. In one specific, non-limiting example, X is a G. In particular, non-limiting examples, the oligodeoxynucleotide includes a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 21, SEQ ID NO: 22, SEQ ID NO: 23, SEQ ID NO: 24, and SEQ ID NO: 25.

The D and K oligodeoxynucleotides disclosed herein can be synthesized de novo using any of a number of procedures well known in the art. For example, the oligodeoxynucleotides can be synthesized as set forth in U.S. Pat. No. 6,194,388, which is herein incorporated by reference in its entirety. A D oligodeoxynucleotide may be synthesized using, for example, by the B-cyanoethyl phosphoramidite method or nucleoside H-phosphonate method. These chemistries can be performed by a variety of automated oligonucleotide synthesizers available in the market. Alternatively, oligodeoxynucleotides can be prepared from existing nucleic acid sequences (e.g. genomic or cDNA) using known techniques, such as employing restriction enzymes, exonucleases or endonucleases, although this method is less efficient than direct synthesis.

B. Pharmaceutical Compositions

The immunostimulatory ODNs described herein may be formulated in a variety of ways depending on the location and type of disease to be treated or prevented. Pharmaceutical compositions are thus provided for both local (e.g. topical or inhalational) use and for systemic use. Therefore, the disclosure includes within its scope pharmaceutical compositions comprising at least one immunostimulatory ODN formulated for use in human or veterinary medicine. While the immunostimulatory ODNs will typically be used to treat human subjects, they may also be used to treat similar or identical diseases in other vertebrates, such other primates, dogs, cats, horses, and cows.

Pharmaceutical compositions that include at least one immunostimulatory K or D ODN as described herein as an active ingredient, or that include both an immunostimulatory ODN and an additional anti-infective agent as active ingredients, may be formulated with an appropriate solid or liquid carrier, depending upon the particular mode of administration chosen. Additional active ingredients include, for example, anti-infective agents, such as antibiotics, anti-fungal compounds, anti-viral compounds, and hyper-immune globulin. A suitable administration format may best be determined by a medical practitioner for each subject individually. Various pharmaceutically acceptable carriers and their formulation are described in standard formulation treatises, e.g., *Remington's Pharmaceutical Sciences* by E. W. Martin. See also Wang, Y. J. and Hanson, M. A., *Journal of Parenteral Science and Technology*, Technical Report No. 10, Supp. 42: 2S, 1988.

The dosage form of the pharmaceutical composition will be determined by the mode of administration chosen. For instance, in addition to injectable fluids, inhalational and oral formulations can be employed. Inhalational preparations can include aerosols, particulates, and the like. In general, the goal for particle size for inhalation is about 1 μm or less in order that the pharmaceutical reach the alveolar region of the lung for absorption. Oral formulations may be liquid (e.g., syrups, solutions, or suspensions), or solid (e.g., powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

In some embodiments, the bioavailability and duration of action of CpG ODN may improve their therapeutic efficacy. One potential method for protecting CpG ODN from degradation while increasing their uptake by cells of the immune system involves liposome encapsulation (MacDonald et al., *Biochim. Biophys. Acta* 1061:297, 1991; Takeshita et al., *Eur. J. Immunol.* 30:108, 2000). Sterically stabilized cationic liposomes (SSCL) compositions efficiently incorporate and deliver K type CpG ODNs to cells in vitro and in vivo. The SSCLs are liposomes that include a cationic lipid, a colipid, and a stabilizing additive, as described below.

Cationic lipids include, but are not limited to spermidine-cholesterol, spermine-cholesterol, is dimethylaminoethae-carbomol-chlesteroc (DC-CHOL), and dioctadecylamidoglycylspermine (DOGS). In one embodiment, the cationic lipid is dimethylaminoethane-carbomol-cholesterol (DC-CHOL). Colipids include, but are not limited to, neutral, zwitterionic, and anionic lipids. In one embodiment, the colipid is dioleoylphosphatidylethanolamine (DOPE). The colipid can be a moiety that allows the stabilizing additive (see below) to be incorporated into the complex. Without being bound by theory, derivatization of the lipid with an additive allows the moiety to anchor the stabilizing additive to the cationic lipid complex. The colipid can be conjugated to additives which prevent aggregation and precipitation of cationic lipid-nucleic acid complexes. Colipids which may be used to incorporate such additives to compositions disclosed herein include, but are not limited to, zwitterionic or other phospholipids. Preferably, the colipid is inert and biocompatible.

The ratio of cationic lipid to colipid (as a molar ratio) is from about 3:7 to about 7:3. In one embodiment, the ratio of cationic lipid to colipid (molar ratio) is about 4:6 to about 6:4. In a further embodiment, the lipid to colipid (molar ratio) is about 4:6. Thus, in one specific, non-limiting example DC-CHOL and DOPE are included in the sterically stabilized cationic liposome at a molar ratio of about 4:6.

Stabilizing agents are also included in the sterically stabilized cationic liposomes. Without being bound by theory, it is believed that the stabilizing agent maintains the integrity of the complex, maintains stability during sizing procedures, and increases shelf life. In one embodiment, the additives are bound to a moiety capable of being incorporated into or binding to the complex, for example, a colipid. Such additives generally are selected from among hydrophilic polymers, which include, but are not limited to, polyethylene glycol, polyvinylpyrrolidine, polymethyloxazoline, polyethyl-oxazoline, polyhydroxypropyl methacrylamide, polylactic acid, polyglycolic acid, and derivatized celluloses such as hydroxymethylcellulose or hydroxyethylcellulose (see published PCT Application No. WO 94/22429). Other stabilizing agents include, but are not limited to perfluorinated or partially fluorinated alkyl chains, fluorinated phospholipids, fatty acids and perfluoroalkylated phospholipids and polyglucoronic acids (Oku et al., *Critical Reviews in Therapeutic Drug Carrier System,* 11:231-270, 1994).

A variety of methods are available for preparing liposomes as described in, e.g., Szoka et al., *Ann. Rev. Biophys. Bioeng.* 9:467, 1980; U.S. Pat. No. 4,186,183; U.S. Pat. No. 4,217,344; U.S. Pat. No. 4,235,871; U.S. Pat. No. 4,261,975; U.S. Pat. No. 4,485,054; U.S. Pat. No. 4,501,728; U.S. Pat. No. 4,774,085; U.S. Pat. No. 4,837,028; U.S. Pat. No. 4,946,787; PCT Publication No. WO 91/17424; Szoka & Papahadjopoulos, *Proc. Natl. Acad. Sci. USA* 75:4194-4198, 1978; Deamer & Bangham, *Biochim. Biophys. Acta* 443:629-634, 1976; Fraley et al., *Proc. Natl. Acad. Sci. USA* 76:3348-3352, 1979; Hope et al., *Biochim. Biophys. Acta* 812:55-65, 1985; Mayer et al., *Biochim. Biophys. Acta* 858:161-168, 1986; Williams et al., *Proc. Natl. Acad. Sci. USA* 85:242-246, 1988, Liposomes, ch. 1 (Ostro, ed., 1983); and Hope et al., *Chem. Phys. Lip.* 40:89, 1986; U.S. Pat. No. 6,410,049. Suitable methods include, e.g., sonication, extrusion, high pressure/homogenization, microfluidization, detergent dialysis, calcium-induced fusion of small liposome vesicles, and ether-infusion methods, all well known in the art.

In one embodiment, a pharmacological composition is provided that includes a D or K oligonucleotide and a pharmacologically acceptable carrier. Pharmacologically acceptable carriers (e.g., physiologically or pharmaceutically acceptable carriers) are well known in the art. A suitable pharmacological composition can be formulated to facilitate the use of K or D type ODN in vivo. Such a composition can be suitable for delivery of the active ingredient to any suitable host, such as a patient for medical application, and can be manufactured in a manner that is itself known, e.g., by means of conventional mixing dissolving, granulating, dragee-making, levigating, emulsifying, encapsulating, entrapping, or lyophilizing processes.

The compositions or pharmaceutical compositions can be administered by any route, including parenteral administration, for example, intravenous, intraperitoneal, intramuscular, intraperitoneal, intrasternal, or intra-articular injection or infusion, or by sublingual, oral, topical, intra-nasal, or transmucosal administration, or by pulmonary inhalation. When immunostimulatory ODNs are provided as parenteral compositions, e.g. for injection or infusion, they are generally suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring, and sweetening agents as appropriate.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

Pharmaceutical compositions that comprise an immunostimulatory ODN as described herein as an active ingredient will normally be formulated with an appropriate solid or liquid carrier, depending upon the particular mode of administration chosen. The pharmaceutically acceptable carriers and excipients of use are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate. Actual methods of preparing such dosage forms are known, or will be apparent, to those skilled in the art.

For example, for parenteral administration, immunostimulatory ODNs can be formulated generally by mixing them at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. A pharmaceutically acceptable carrier is a non-toxic solid, semisolid or liquid filler, diluent, encapsulating material or formulation auxiliary of any type.

Generally, the formulations are prepared by contacting the immunostimulatory ODNs each uniformly and intimately with liquid carriers or finely divided solid carriers or both. Then, if necessary, the product is shaped into the desired formulation. Optionally, the carrier is a parenteral carrier, and in some embodiments it is a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The pharmaceutical compositions that comprise an immunostimulatory ODN, in some embodiments, will be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

The therapeutically effective amount of immunostimulatory ODN will be dependent on the ODN utilized, the subject being treated, the severity and type of the affliction, and the manner of administration. For example, a therapeutically effective amount of immunostimulatory ODN can vary from about 0.01 μg per kilogram (kg) body weight to about 1 g per kg body weight, such as about 1 μg to about 5 mg per kg body weight, or about 5 μg to about 1 mg per kg body weight. The exact dose is readily determined by one of skill in the art based on the potency of the specific compound (such as the immunostimulatory ODN utilized), the age, weight, sex and physiological condition of the subject.

C. Therapeutic Uses

Methods are disclosed herein for treating or preventing an infection in a subject who has been exposed to or is at risk for exposure to a bioterrorism agent. These methods include:

1. administering a therapeutically effective amount of the immunostimulatory ODN to a subject who has been exposed to or is at risk for exposure to a bioterrorism agent,
2. administering a therapeutically effective amount of the immunostimulatory ODN in combination with an anti-infective agent to a subject who has been exposed to or is at risk for exposure to a bioterrorism agent, thereby treating or preventing the infection in a subject, and
3. administering to the subject a therapeutically effective amount of an immunostimulatory D oligodeoxynucleotide or an immunostimulatory K oligodeoxynucleotide in combination with a vaccine against a bioterrorism agent.

Bioterrorism agents include, but are not limited to *Bacillus anthracis, Yersinia pestis, Variola major, Histoplasma capsulatum, Haemophilus influenzae*, Ebola virus, tick-borne encephalitis virus (TBEV), *Escherichia coli, Shigella flexneri, S. dysenteriae* (*Shigella bacillus*), *Salmonella, Staphylococcus* enterotoxin B, botulinum toxin, ricin toxin, cobra venom, shellfish toxin, botulinum toxin, saxitoxin, ricin toxin, tricothecene mycotoxin, or aflatoxin. Exposure to bioterrorism agents can result in infections, such as, but not limited to, anthrax, cryptococcosis, brucellosis, coccidioidomycosis, psittacosis, bubonic plague, tularemia, malaria, cholera, typhoid, hemorrhagic fever, tick-borne encephalitis, Venezuelan equine encephalitis, pneumonic plague, Rocky Mountain spotted fever, dengue fever, Rift Valley fever, diphtheria, melioidosis, glanders, tuberculosis, infectious hepatitis, encephalitides, blastomycosis, nocardiosis, yellow fever, typhus, or Q fever.

Some embodiments of the methods include administering a therapeutically effective amount of the immunostimulatory ODN to a subject who has been exposed to or is at risk for exposure to a bioterrorism agent, thereby treating or preventing the infection in a subject. Without being bound by theory, administration of the immunostimulatory ODN increases the general immune activation, leading to an increase in the immune response to the bioterrorism agent or vaccine. In this manner, a subject can be at reduced risk of infection or susceptible to fewer symptoms, and can obtain further treatment if necessary. In one embodiment, the immunostimulatory ODN can be administered locally, such as by inhalation. In another embodiment, the immunostimulatory ODN is administered systemically, such as by intravenous injection, intramuscular injection, or subcutaneous injection.

In some embodiments, the immunostimulatory ODN is administered to the subject prior to exposure to a bioterrorism agent, for example, two weeks, one week, one day, six hours, or one hour prior to exposure. The immunostimulatory ODN can also be administered to the subject after exposure to a bioterrorism agent, for example, two weeks, one week, one day, six hours, or one hour after exposure. In some embodiments, the immunostimulatory ODN is administered to a subject who is at risk for exposure to a bioterrorism agent, for example, a member of the military, a police officer, a mail handler, a government official, or any other individual who is at risk for exposure to a bioterrorism agent. For example, in one specific, non-limiting example, an immunostimulatory ODN is administered to a member of the military three days, six days, or two weeks before deployment. Suitable subjects also include those who are more prone to illness following bioterrorism agent exposure, such as subjects with weakened immune systems, for example, the elderly, people on immunosuppressive drugs, subjects with cancer, and subjects infected with HIV Combinations of these immunostimulatory ODNs are also of use. Thus, in one embodiment, more than one immunostimulatory D or K ODN, or both D and K ODNs, each with a different nucleic acid sequence, are administered to the subject. In several specific, non-limiting examples, at least two, at least three, or at least four immunostimulatory D ODNs are administered to the subject. In other specific, non-limiting examples, at least two, at least three, or at least four immunostimulatory K ODNs are administered to the subject. In still further specific, non-limiting examples, at least two, at least three, or at least four immunostimulatory D ODNs are administered to the subject in combination with at least two, at least three, or at least four immunostimulatory K ODNs.

An effective amount of an immunostimulatory ODN can be administered in a single dose, or in multiple doses, for example weekly, during a course of treatment. In one embodiment, a therapeutically effective amount of an immunostimulatory ODN is administered as a single pulse dose, as a bolus dose, or as pulse doses administered over time. Thus, in pulse doses, a bolus administration of an immunostimulatory ODN is provided, followed by a time period wherein no immunostimulatory ODN is administered to the subject, followed by a second bolus administration. In specific, non-limiting examples, pulse doses of an immunostimulatory ODN are administered during the course of a day, during the course of a week, or during the course of a month.

Thus, the immunostimulatory ODNs disclosed herein may be administered to a subject for the treatment of a bioterrorism agent-induced infection in that individual. ODN administration can be systemic or local. Local administration of the ODN is performed by methods well known to those skilled in the art. By way of example, one method of administration to the lungs of an individual is by inhalation through the use of a nebulizer or inhaler. For example, the ODN is formulated in an aerosol or particulate and drawn into the lungs using a standard nebulizer well known to those skilled in the art.

In other embodiments, the administration of the immunostimulatory ODN is systemic. Oral, intravenous, intra-arterial, subcutaneous, intra-peritoneal, intra-muscular, and even rectal administration is contemplated. Prevention of an infection includes both prevention of symptoms and delaying the onset of symptoms. In specific, non-limiting examples, administration of an immunostimulatory ODN delays symptoms of an infection until further treatment is sought.

The effectiveness of treatment with an immunostimulatory ODN can be measured by monitoring symptoms of infection, for example, fever. For example, a decrease in fever over time is an indicator of efficacy of ODN treatment.

In some embodiments, the method includes administering to the subject an anti-infective agent, such as an antibiotic, anti-viral compound, anti-fungal compound, or hyper-immune globulin, in conjunction with an immunostimulatory ODN. The administration of the additional anti-infective agent and the immunostimulatory ODN can be sequential or simultaneous.

Anti-infectious agents include, but are not limited to, anti-fungal compounds, anti-viral compounds, and antibiotics. Antibiotics include, but are not limited to, amoxicillin, clarithromycin, cefuroxime, cephalexin ciprofloxacin, doxycycline, metronidazole, terbinafine, levofloxacin, nitrofurantoin, tetracycline, and azithromycin. Anti-fungal compounds, include, but are not limited to, clotrimazole, butenafine, butoconazole, ciclopirox, clioquinol, clioquinol, clotrimazole, econazole, fluconazole, flucytosine, griseofalvin, haloprogin, itraconazole, ketoconazole, miconazole, naftifine, nystatin, oxiconazole, sulconazole, terbinafine, terconazole, tioconazole, and tolnaftate. Anti-viral compounds, include, but are not limited to, zidovudine, didanosine, zalcitabine, stavudine, lamivudine, abacavir, tenofovir, nevirapine, delavirdine, efavirenz, saquinavir, ritonavir, indinavir, nelfinavir, saquinavir, amprenavir, and lopinavir. Anti-infectious agents also include hyper-immune globulin.

Other methods described herein are methods of enhancing the immunogenicity of a vaccine against a bioterrorism agent in a subject. In some embodiments, the vaccine against a bioterrorism agent is an antigen. The method includes administering to the subject a therapeutically effective amount of an immunostimulatory D oligodeoxynucleotide or an immunostimulatory K oligodeoxynucleotide in combination with a vaccine against a bioterrorism agent, thereby enhancing the efficacy of the vaccine. The vaccine can be a preparation of antigen, DNA, protein subunit, peptide, attenuated microorganisms (including but not limited to bacteria and viruses), living microorganisms, or killed microorganisms, administered for the prevention, amelioration or treatment of a disease caused by a bioterrorism agent.

In some embodiments, the vaccine is a heat or formalin-killed vaccine. Examples of heat-killed vaccines in common use today are the typhoid vaccine and the Salk poliomyelitis vaccine.

In other embodiments, the vaccine is an acellular vaccine. Acellular vaccines are made using only the antigenic part of the disease-causing organism, for example the capsule, the flagella, or part of the protein cell wall. In still other embodiments, the vaccine is an attenuated vaccine. Attenuated vaccines are made by "attenuating" or weakening a live microorganism by aging it or altering its growth conditions. In still further embodiments, the vaccine is a toxoid.

In other embodiments, the vaccine is made from a related, less virulent pathogen. The related pathogen does not cause serious disease, but provides protection from the more virulent pathogen. For example, the relatively mild cowpox virus is used to protect against the similar, but often lethal, smallpox virus. In still further embodiments, the vaccine is a subunit vaccine or a DNA vaccine.

Thus, a CpG oligonucleotide can be used in conjunction with a wide variety of vaccines against a bioterrorism agent, including but not limited to, a heat or formalin-killed vaccine, attenuated vaccine, protein subunit vaccine, antigen vaccine, DNA vaccine, acellular vaccine, or toxoid vaccine directed against *Bacillus anthracis, Yersinia pestis, Variola major*, tick-borne encephalitis virus (TBEV), Ebola virus, *Escherichia coli, Haemophilus influenzae*, cobra venom, shellfish toxin, botulinum toxin, saxitoxin, ricin toxin, *Shigella flexneri, S. dysenteriae* (*Shigella bacillus*), *Salmonella, Staphylococcus* enterotoxin B, *Histoplasma capsulatum*, tricothecene mycotoxin, aflatoxin. The vaccine can also be directed against cryptococcosis, brucellosis (undulant fever), coccidioidomycosis (San Joaquin Valley or desert fever), psittacosis (parrot fever), bubonic plague, tularemia (rabbit fever), malaria, cholera, typhoid, hemorrhagic fever, tick-borne encephalitis, Venezuelan equine encephalitis, pneumonic plague, Rocky Mountain spotted fever, dengue fever, Rift Valley fever, diphtheria, melioidosis, glanders, tuberculosis, infectious hepatitis, encephalitides, blastomycosis, nocardiosis, yellow fever, typhus, and Q fever. In some embodiments, the vaccine is an antigen from *Bacillus anthracis*, Ebola virus, tick-borne encephalitis virus (TBEV), *Yersinia pestis, Variola major, Histoplasma capsulatum, Haemophilus influenzae, Escherichia coli, Shigella flexneri, S. dysenteriae* (*Shigella bacillus*), *Salmonella*, or *Staphylococcus*.

In particular examples of certain embodiments, the vaccine is an anthrax vaccine, such as, but not limited to AVA, or an anthrax antigen, such as, but not limited to Protective Antigen (PA) or recombinant Protective Antigen (rPA).

Primary vaccination with AVA generally consists of three subcutaneous injections at 0, 2, and 4 weeks, and three booster vaccinations at 6, 12, and 18 months. To maintain immunity, the manufacturer recommends an annual booster injection. Because of the complexity of a six-dose primary vaccination schedule and frequency of local injection-site reactions, schedules with a reduced number of doses would be desirable. Administration of AVA in conjunction with an immunostimulatory D or K ODN provides a better immune response to the vaccine than use of the vaccine alone, and can result in a decreased frequency of immunizations required to attain an immune protective response.

In particular, non-limiting examples, the vaccine is a DNA sequence encoding the non-toxic protective antigen (PA) from *B. anthracis* or an immunogenic fragment thereof. The sequence for PA has been determined and has been deposited in GenBank at Accession No. M22589. Other antigens of use include, but are not limited to, *B. anthracis* lethal factor (LF) or an immunogenic fragment thereof, disclosed in U.S. Publication No. U.S. 2002/0051791A1, hantavirus antigens, for example those disclosed in U.S. Pat. No. 5,614,193, smallpox antigens, for example those disclosed in U.S. Pat. No. 4,567,147, plague antigens, for example those disclosed in WO 98/24912 A2, Ebola virus antigens, for example those disclosed in WO 00/00617A2, tick-borne encephalitis antigens, for example those disclosed in U.S. Pat. No. 6,372,221 and EP 0691404 B1, *Histoplasma capsulatum* antigens, for example those disclosed in WO 99/55874A2 and U.S. Pat. No. 6,391,313, *Haemophilus influenzae* antigens, for example those disclosed in U.S. Pat. No. 6,342,232, EP 0432220 B1, and U.S. Pat. No. RE 37741, *E. coli* antigens, for example those disclosed in U.S. Pat. No. 5,370,872, U.S. Pat. No. 6,077,516, and U.S. Pat. No. 3,975,517, *Shigella* antigens, for example those disclosed in U.S. Pat. No. 5,077,044, U.S. Pat. No. 5,686,580, and U.S. Pat. No. 5,681,736, *Salmonella* antigens, for example those disclosed in WO 01/70247 A2, U.S. Publication No. 2001/0021386A1 and EP 1112747A1, and *Staphylococcus* antigens, for example those disclosed in EP 0694309A3 and U.S. Pat. No. 6,391,315.

The method includes administering a therapeutically effective amount of the immunostimulatory D and/or K ODN to a subject in conjunction with a vaccine against a bioterrorism agent, thereby enhancing the immunogenicity of the vaccine. In one embodiment, the immunostimulatory ODN can be administered locally, such as topically or by inhalation. In another embodiment, the immunostimulatory ODN is administered systemically, such as by intravenous injection, intramuscular injection, or subcutaneous injection.

Combinations of immunostimulatory ODNs are also of use in enhancing the immunogenicity of a vaccine against a bioterrorism agent. Thus, in one embodiment, more than one immunostimulatory ODN, each with a different nucleic acid sequence, are administered to the subject in combination with the vaccine. In several specific, non-limiting examples, at least two, at least three, or at least four immunostimulatory ODNs are administered to the subject in combination with the vaccine.

An effective amount of an immunostimulatory ODN can be administered in combination with a vaccine against a bioterrorism agent in a single dose, or in multiple doses. For example, in some embodiments, boosters of the vaccine and immunostimulatory ODN can be administered periodically after the initial administration, for example, at one month, two months, or three months after the initial administration. In specific, non-limiting examples, pulse doses of an immunostimulatory ODN, in combination with a vaccine against a bioterrorism agent, are administered at 2 weeks, 4 weeks, 6 months, 12 months, 18 months, or yearly after the initial bolus administration.

In other embodiments, a subject who likely has been exposed to a bioterrorism agent can receive a vaccine against a bioterrorism agent in conjunction with an immunostimulatory D or K ODN and an anti-infective agent. For example, during a course of treatment of a suspect who has been, or is likely to have been exposed to a bioterrorism agent, the vaccine and ODN can be administered daily, weekly, or every two weeks.

The immunostimulatory ODNs can be administered before vaccine administration, concurrently with vaccine administration or after vaccine administration. For example, the immunostimulatory ODN can be administered before the vaccine is administered, for instance, two weeks, one week, one day, or one hour before the vaccine is administered to the subject. Alternatively, the immunostimulatory ODN can be administered concurrently with vaccine administration, or, for instance, two weeks, one week, one day, or one hour after the vaccine is administered to the subject.

Thus, the immunostimulatory ODNs described herein can be administered to a subject in combination with a vaccine against a bioterrorism agent in order to enhance the immunogenicity of the vaccine. The effectiveness of the ODN administration can be measured by monitoring vaccine against a bioterrorism agent titer or avidity of antibody response, or cytotoxic T cell response, by methods known to one of skill in the art. For example, an increase in vaccine against a bioterrorism agent titer or avidity of antibody response over time is an indicator of efficacy of ODN treatment.

The disclosure is illustrated by the following non-limiting Examples.

EXAMPLES

Example 1

Materials and Methods

Reagents

Phosphorothioate ODN (Table 1) were synthesized or obtained from a commercial source. Specifically, CpG 7909 (SEQ ID NO: 200) and CpG 10103 are both K type ODN that were obtained from Coley Pharmaceuticals (Wellesley, Mass.). All synthesized ODN had less than <0.1 EU of endotoxin per mg of ODN as assessed by a Limulus amebocyte lysate assay (QCL-1000, BioWhittaker).

AVA was obtained from BioPort Corporation (East Lansing, Md.). Recombinant PA (rPA) was produced as previously described (Farchaus et al., *Appl. Environ. Microbiol.* 64:982, 1998). For vaccinations, 50 μg of rPA was dissolved in 0.5 ml of PBS plus 0.5 mg of aluminum. (Alhydrogel, SuperFos/BioSector, Denmark).

The *Bacillus anthracis* Ames and Vollum 1B strains were obtained from the culture collection of the United States Army Medical Research Institute of Infectious Diseases, Fort Detrick, Md. Spores were prepared and stored as previously described (Ivins et al., *Infect. Immun.* 58:303, 1990).

TABLE 1

Sequence and backbone of murine and human ODN

| Species | Designation | SEQ ID NO: | Sequence |
|---|---|---|---|
| Mouse | CpG ODN 1555 | SEQ ID NO: 17 | GCTAGACGTTAGCGT |
| Mouse | CpG ODN 1466 | SEQ ID NO: 18 | TCAACGTTGA |
| Mouse | Control ODN | SEQ ID NO: 19 | GCTAGAGCTTAGGCT |
| Mouse | Control ODN | SEQ ID NO: 20 | TCAAGCTTGA |
| Human | CpG ODN D19 | SEQ ID NO: 21 | *GG*TGCATCGATGCAGG*GGGG* |
| Human | CpG ODN D29 | SEQ ID NO: 22 | *GG*TGCACCGGTGCAGG*GGGG* |
| Human | CpG ODN D35 | SEQ ID NO: 21 | *GG*TGCATCGATGCAGG*GGGG* |
| Human | CpG ODN K3 | SEQ ID NO: 23 | ATCGACTCTCGAGCGTTCTC |
| Human | CpG ODN K123 | SEQ ID NO: 24 | TCGTTCGTTCTC |
| Human | CpG ODN K23 | SEQ ID NO: 25 | TCGAGCGTTCTC |
| Human | Control ODN | SEQ ID NO: 26 | GGTGCATTGATGCAGGGGGG |

TABLE 1-continued

Sequence and backbone of murine and human ODN

| Species | Designation | SEQ ID NO: | Sequence |
|---|---|---|---|
| Human | Control ODN | SEQ ID NO: 27 | TTGAGTGTTCTC |
| Human | Control ODN | SEQ ID NO: 28 | GGGCATGCATGGGGGG |

Bases shown in italics are phosphodiester while all others are phosphorothioate. CpG dinucleotides are underlined.

Animals

All animal studies were ACUC approved and were conducted in AAALAC accredited facilities. Animals were monitored daily by veterinarians. Specific pathogen-free BALB/c mice were obtained from the Jackson Laboratories (Bar Harbor, Me.) and housed in sterile micro-isolator cages in a barrier environment. Mice were injected i.p. at 6-8 weeks of age with 50 μg of CpG ODN and then challenged SQ with 11-70 LD50 *B. anthracis* Vollum 1B spores.

Hartley guinea pigs, 325-375 gm (Charles River) were immunized IM with 0.5 ml-doses of AVA plus 100-300 μg of CpG ODN, and boosted with the same material 4 weeks later. Animals were challenged IM at week 10 with 5,000 (50 LD50) Ames spores.

Healthy 3 year old female rhesus macaques were obtained from the FDA colony in South Carolina. Five to six animals/group were immunized subcutaneously at 0 and 6 weeks with the normal human dose of AVA (0.5 ml) or rPA (50 μg) plus 250 μg of "K" or "D" CpG ODN. Animals were "challenged" IM with the live veterinary vaccine strain of anthrax (Sterne) on week 27. Treatments were administered and peripheral blood samples obtained from ketamine anesthetized animals (10 mg/kg, Ketaject, Phoenix Pharmaceuticals, St. Joseph, Md.).

For several of the experiments, five groups of 5 male and female rhesus macaques/group were immunized subcutaneously (SQ) or intramuscularly (1) on study days 0 and 42 with 0.5 mL of AVA plus 0 or 250 μg of CpG ODN. All animals were monitored daily by veterinarians. Treatments were administered under appropriate anesthesia. A baseline blood sample was collected from each non-human primate (NHP) 10 days before the first injection (study day-10). Blood was collected from each NHP on days 1, 4, 11, 16, 21, 28, 35, 42, 49, 56, and 63 after the first injection.

Anti-PA ELISA and Avidity Assays

The titer of IgG against the anthrax PA was monitored by enzyme linked immunosorbent assay (ELISA). Anti-PA IgG is considered a marker of vaccine efficacy as anti-PA antibodies confer protection to host cells by blocking the binding of anthrax toxin (see Pittman et al., *Vaccine* 20:1412-1420, 2002). Anti-PA antibodies also inhibit spore germination and increase the uptake and elimination of spores by macrophages (Welkos et al., *Microbiology* 147:1677-1685, 2001). The titer of anti-PA IgM was also evaluated by ELISA to evaluate any differences in the immunogenicity of the vaccine and adjuvant combinations.

Microtiter plates (96-well Immulon 2; Dynex Technologies Inc., Chantilly, Va.) were coated with 1 μg/ml of rPA in PBS and then blocked with PBS-5% non-fat milk and dried overnight. Serum samples diluted in blocking buffer were incubated on rPA-coated microtiter plates for 2 hours. After coating, plates were blocked with 0.1% Tween 20 with 2% non-fat dry milk in PBS for one hour at room temperature.

Plates were then overlaid with serially diluted serum for 1 hour at 37° C. as described (Ivins et al., *Infect Immun* 60, 662-668, 1992). The plates were washed, and bound antibody detected using peroxidase-conjugated goat anti-monkey IgG or IgM (Kirkegaard & Perry, Gaithersburg, Md.) followed by ABTS substrate (Kirkegaard & Perry). Antibody titers were determined by comparison to a standard curve generated using high-titered anti-PA serum. All samples were analyzed in triplicate. All assays were performed the same day using the same reagents for all plates.

For avidity studies, the plates were washed, and were treated for 15 minutes with 200 μl of 6M urea. Bound antibodies were detected by adding peroxidase-labeled goat anti-monkey IgG (Kirkegaard & Perry Laboratories, Gaithersburg, Md.) followed by ABTS (Kirkegaard & Perry Laboratories). Titers were determined by comparison to a standard curve generated using high-titered anti-serum. All samples were analyzed in triplicate.

TNA Assay

The TNA assay evaluates the ability of the test serum to neutralize the cytotoxic effects of anthrax lethal toxin (a mixture of PA and anthrax lethal factor (LF)) in an in vitro assay. A murine target cell line susceptible to anthrax lethal toxin is incubated with mixtures of lethal toxin with control sera or lethal toxin with test sera. Percent cytotoxicity is determined by the addition of a colorimetric substrate, MTT, that in turn is hydrolyzed by the remaining viable cells into a purple formazan precipitate, which is solubilized and quantitated on a plate reader. The effective dose 50 ($ED_{50}$) is calculated as the reciprocal of the dilution of test serum at which 50% neutralization of the lethal toxin is achieved. The concentration of neutralizing antibody is calculated using the ratio of the $ED_{50}$ of the test serum compared to the $ED_{50}$ of a standard reference serum.

Mouse Seroprotection Assay

Serum samples collected for the immunogenicity assays described above were stored frozen at −80° C. until use. Equal volumes of serum from all animals in each treatment group from study day 11 and separately from study day 16 were pooled. 100 μl of this serum pool was injected IV into 6 week old, male A/JCr mice (10 recipients/group). Twenty-four hours later, blood was collected from the tail vein from a subset of these animals (4-total) to assess serum IgG anti-PA titers. All mice were then challenged i.p. with 30-60 $LD_{50}$ of Sterne strain anthrax spores diluted in 500 μl of PBS. Survival of these mice was monitored daily for 3 weeks, and the time to death recorded. No mortality was observed in any group after day 10. The experiment was conducted twice.

Statistical Analysis

Challenge experiments were performed using a minimum of 5-10 mice/group. Survival differences were evaluated using Student's t test, while differences in serum anti-PA Ab titers (or avidity) were evaluated by multiple regression ANOVA.

Example 2

Immunoprotective Activity of CpG ODN

The ability of CpG ODN to improve the survival of normal BALB/c mice challenged with *B. anthracis* Vollum 1B spores was demonstrated. The fraction of BALB/c mice surviving infection, and/or their mean time to death (MTD), was significantly improved by CpG ODN treatment 3-6 days prior to challenge (Table II). The earlier treatment was initiated, the greater the beneficial effect, consistent with the hypothesis that CpG motifs stimulate an immune cascade that matures over several days and then persists for several weeks (Elkins et al., *J. Immunol.* 162:2291, 1999; Klinman et al., *Immunity* 11:123, 1999). A modest prolongation in mean time to death (MTD) was observed in mice treated with CpG ODN one day prior to challenge, while treatment at the same time or after pathogen exposure had no effect on survival (Table II).

TABLE II

Effect of CpG ODN on the survival of mice challenged with anthrax

| | | Experiment 1 | | Experiment 2 | |
|---|---|---|---|---|---|
| Treatment | Day | % survival | MTD | % survival | MTD |
| CpG ODN | −6 | 50* | 120 | | |
| CpG ODN | −3 | 0 | 110 | 20 | 114 |
| CpG ODN | 0 | 0 | 98 | | |
| CpG ODN | 1 | 0 | 89 | | |
| No Rx | 0 | 98 | 0 | 96 | |

BALB/c mice (N = 10/group) were treated with 50-100 μg of CpG D ODN on the day shown, and infected with 70 (Exp 1) or 11 (Exp 2) *B. anthracis* 1B spores on Day 0. Survival and mean time to death (MTD in hours) is shown.
*Significantly improved survival compared to untreated mice, $p < .05$.

Thus, these CpG ODN can significantly reduce the mortality of mice infected with anthrax. Although 100% survival was not achieved, the mean time to death (MTD) was consistently prolonged, thus providing a "window of opportunity" to initiate life-saving antibiotic therapy. The activity of the ODN was unambiguously attributed to their CpG content, since control ODN in which the CpG dinucleotide was inverted to a GpC provided no protection.

Example 3

CpG ODN as Vaccine Adjuvants

Since exposure to anthrax is rarely predictable, the possibility that CpG ODN could be used to enhance the immunogenicity of protective vaccines was demonstrated. Due to evolutionary divergence in CpG recognition between species, CpG motifs that are highly active in rodents are poorly immunostimulatory in primates, and vice versa (Bauer et al., *Immunology* 97:699, 1999; Hartmann and Krieg, *J. Immunology* 164:944, 2000; Verthelyi et al., *J. Immunol.* 166:2372, 2001). Thus, primate models are optimal for examining the activity of CpG ODN being developed for human use. Immune cells from rhesus macaques respond to the same two classes of ODN that stimulate human cells (Streilein et al., *Immunol. Today* 18:443, 1997). "D" type ODN trigger primate cells to secrete IFN-α and IFNg and promote the functional maturation of APC, whereas "K" type ODN induce immune cells to proliferate and secrete IL-6 and/or IgM (Verthelyi et al., *J. Immunol.* 166:2372, 2001).

Figure 1:
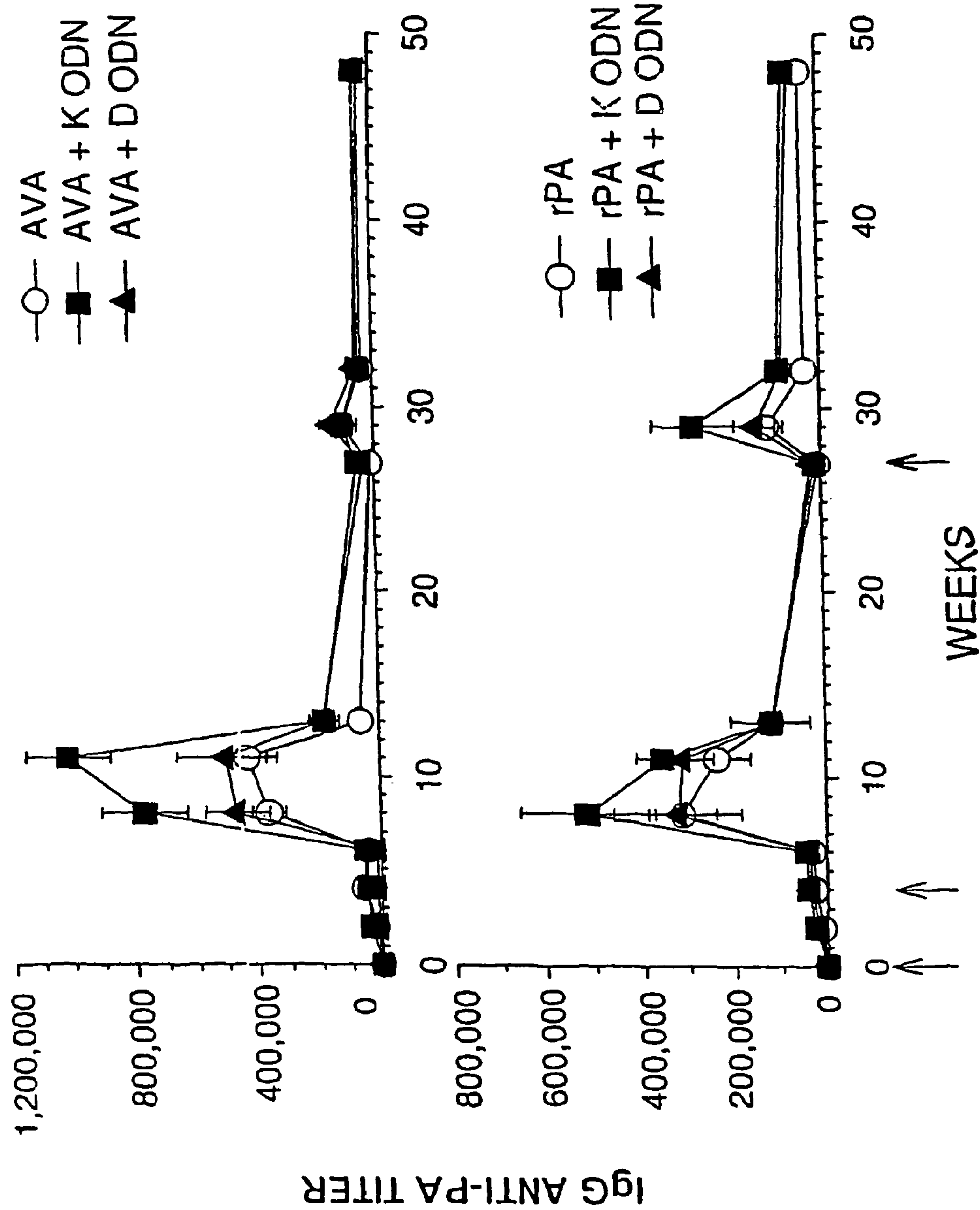
FIG. 1 is a graph showing that K ODN significantly increases the maximum, average, and long-term IgG anti-PA response in Rhesus macaques when co-administered with AVA or rPA. Rhesus macaques (5-6/group) were immunized SQ at 0 and 4 weeks with 0.5 ml of AVA or 50 μg of rPA in alum. In some cases, these vaccines were co-administered with 250 μg of an equimolar mixture of K3, K23 and K123 (K) or D19, D29 and D35 (D) ODN. Animals were "challenged" IM with the live attenuated veterinary vaccine strain of anthrax on week 27. Results show the geometric mean (+SEM) IgG anti-PA titer calculated by analyzing serum from each animal independently at the time points shown. The time-averaged magnitude of the response induced by K ODN plus AVA or rPA significantly exceeded that of either vaccine alone, $p<0.05$.

Mixtures of K and D ODN that strongly stimulate PBMC from both humans and macaques (Streilein et al., *Immunol. Today* 18:443, 1997) were co-administered as adjuvants with the licensed AVA vaccine and with the rPA vaccine currently undergoing clinical evaluation. As seen in FIG. 1, K ODN significantly increased the maximum, average, and long-term IgG anti-PA responses. Over the duration of study, K ODN increased the GMT of vaccinated macaques by 2.1+0.3 fold ($p<0.03$).

Figure 2:
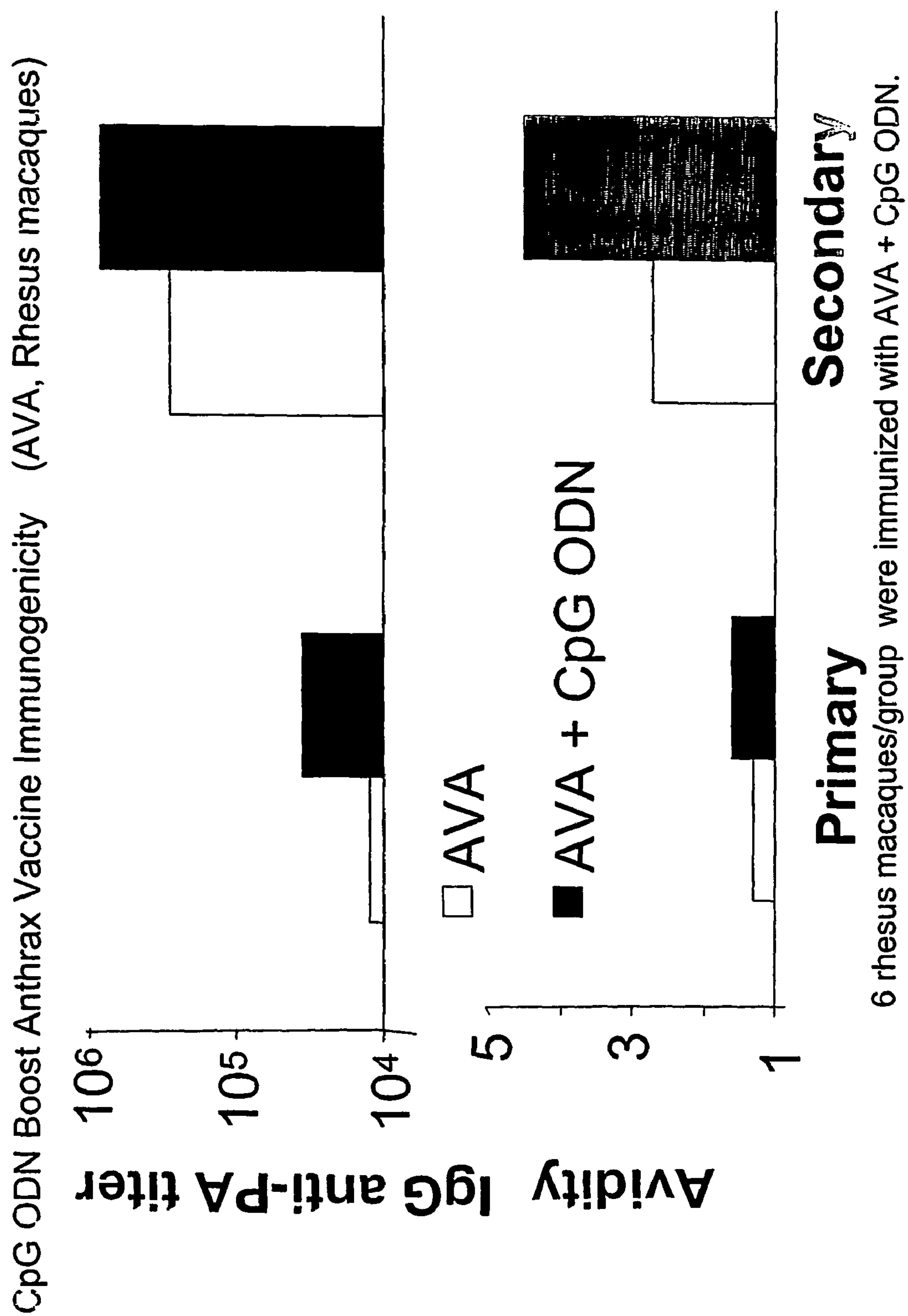
FIG. 2 is a graph showing that K ODN increase serum IgG anti-PA titers and avidity. Six rhesus macaques were immunized SQ at 0 and 4 weeks with 0.5 ml of AVA and then "challenged" IM with the live attenuated veterinary vaccine strain of anthrax on week 27. Serum IgG anti-PA titers and avidity (% of Ab remaining bound after elution with 6 M urea) are shown. Results reflect the geometric mean (+SEM) IgG anti-PA titer derived by analyzing serum from each animal independently at the time points shown.

The quality of a vaccine-adjuvant combination is reflected by both the avidity and titer of the resultant Ab response. The avidity of the IgG anti-PA Abs elicited by AVA or rPA vaccination was monitored by incubating bound serum Abs with 6 M urea. This treatment selectively elutes low avidity Abs (Eggers et al., *J. Med. Virol.* 60:324, 2000; Cozon et al., *Eur. J. Clin. Microbiol. Infect. Dis.* 17:32, 1998). As seen in FIG. 2, nearly 90% of the serum Abs generated by primary vaccination with AVA were eluted by urea treatment. By comparison, <50% of the serum anti-PA Abs present in animals boosted with AVA and then challenged with attenuated anthrax could be eluted, consistent with affinity maturation of the memory response.

There was little difference in the average avidity of the serum anti-PA response of macaques initially immunized with AVA or rPA plus CpG ODN. However, the use of K and D ODN as adjuvants generated Abs of significantly higher avidity post boost when compared to animals immunized and boosted with vaccine alone ($p<0.02$).

Figure 3:
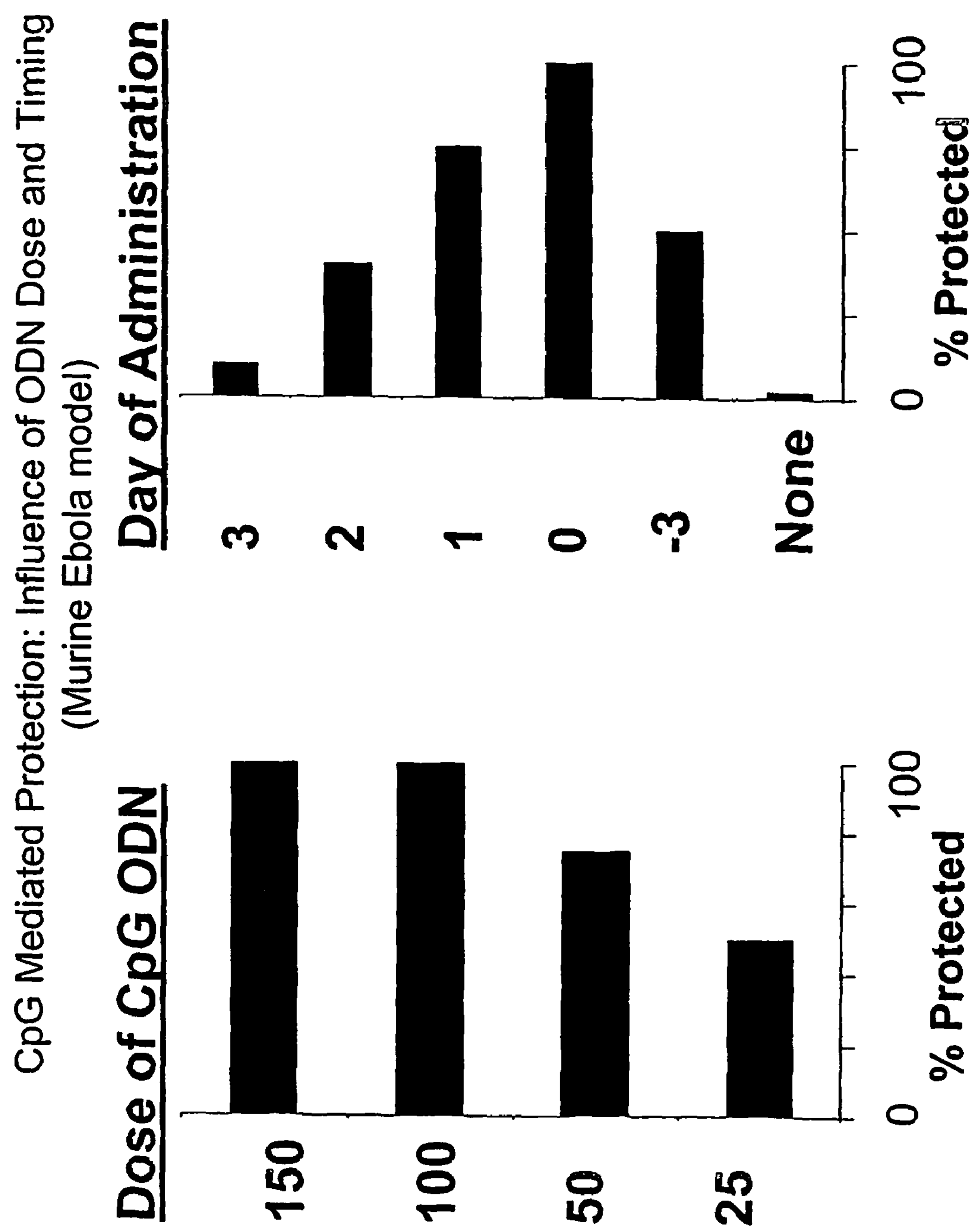
FIG. 3 is a graph showing that dose and timing of CpG administration influences CpG-mediated protection in mice exposed to Ebola virus.

Since CpG motifs that activate human immune cells tend to be weakly immunostimulatory in mice, their adjuvant effects are best assessed in non-human primates. Fortunately, rhesus macaques respond to the same CpG motifs that stimulate human PBMC (Verthelyi et al., *J. Immunol.* 168:1659, 2002). When co-administered with the AVA vaccine, K ODN (which support B cell activation) significantly increased both the titer and avidity of the IgG anti-PA antibody response (FIGS. 1 and 3). When "challenged" with a non-lethal strain of anthrax, macaques immunized with AVA or rPA plus K ODN mounted stronger and longer lasting immune responses (FIG. 1).

Additional studies were performed using two K type ODNs, ODN 7909 (SEQ ID NO: 200) and ODN 10103. For these studies, five groups of 5 male and female rhesus macaques/group were immunized subcutaneously (SQ) or intramuscularly (IM) on study days 0 and 42 with 0.5 mL of AVA plus 0 or 250 μg of CpG ODN. All animals were monitored daily by veterinarians. Treatments were administered under appropriate anesthesia. A baseline blood sample was collected from each non-human primate (NHP) 10 days before the first injection (study day—10). Blood was collected from each NHP on days 1, 4, 11, 16, 21, 28, 35, 42, 49, 56, and 63 after the first injection.

The geometric means of the anti-PA IgG titer of the five vaccination groups for each day were computed. Anti-PA IgG titers for each animal on each serum collection day are shown in Appendix III. The area under the curve (AUC), Tmax and Cmax, for 3 different intervals were also computed as follows:

1. The entire study period up through Day 63 after the first vaccination.
2. The study period up through Day 42, which includes only data prior to the second vaccination.
3. The study period up through Day 21, to more closely assess the early titer response.

AUC was calculated using the trapezoidal rule. Tmax is the time (days after first vaccination) that the animal had the maximum anti-PA IgG titer during the given time period, and Cmax is the anti-PA IgG on that day.

Table III shows the median and mean values for the AUC, Tmax, and Cmax for each of the 3 time periods defined (0-63 days, 042 days, 0-21 days). Numbers with an asterisk indicate that that group was significantly different at the 0.05 significance level than the AVA SQ group, based on the Wilcoxon Rank Sum test.

TABLE III

Median (Mean) Area Under the Curve (AUC), Time to Maximum Concentration (Tmax), and Maximum Concentration (Cmax) by Treatment Group

| | AVA SQ | AVA + K SQ | AVA + 10103 SQ | AVA + 7909 SQ | AVA + 7909 IM | p-value** |
|---|---|---|---|---|---|---|
| | | | Through Day 63 | | | |
| AUC | 27,247,740 | 30,215,702 | 122,771,755 | 43,564,150 | 25,522,306 | 0.32 |
| | (72,440,976) | (34,771,333) | (213,490,038) | (49,416,690) | (35,012,286) | |
| Tmax | 49 | 49 | 49 | *56 | *56 | 0.35 |
| | (49) | (51.8) | (53.2) | (53.2) | (53.2) | |
| Cmax | 2,350,000 | 2,080,000 | 10,867,300 | 2,205,000 | 1,600,000 | 0.25 |
| | (8,491,400) | (2,164,000) | (25,783,660) | (4,013,800) | (2,929,600) | |
| | | | Through Day 42 | | | |
| AUC | 2,163,950 | 4,419,240 | *11,657,355 | *5,479,006 | 5,969,975 | 0.036 |
| | (2,761,226) | (7,507,173) | (10,965,198) | (6,094,460) | (4,922,086) | |
| Tmax | 35 | 35 | 16 | 16 | 16 | 0.28 |
| | (27.4) | (27.4) | (18.4) | (23.6) | (17) | |
| Cmax | 125,000 | 246,000 | *548,000 | *284,500 | 384,250 | 0.048 |
| | (155,932) | (356,222) | (605,512) | (310,522) | (285,132) | |
| | | | Through Day 21 | | | |
| AUC | 492,292 | 1,108,240 | *4,283,805 | *2,052,506 | 2,985,975 | 0.035 |
| | (620,416) | (2,402,633) | (4,289,102) | (2,216,740) | (2,196,426) | |
| Tmax | 16 | 16 | 16 | 16 | 16 | 0.42 |
| | (16) | (15) | (17) | (17) | (17) | |
| Cmax | 67,600 | 164,300 | *539,300 | 284,500 | 384,250 | 0.034 |
| | (86,322) | (319,814) | (600,312) | (258,672) | (285,132) | |

*$p < 0.05$ in comparison to AVA SQ, using the Wilcoxon Rank Sum test

**p-value based on Kruskal-Wallis test comparing all 5 treatment groups

Statistical comparisons were made using nonparametric tests. For each outcome, the 5 treatment groups were compared overall, using the Kruskal-Wallis test. In addition, for each outcome, the Wilcoxon Rank Sum test was performed for the AVA Alone group versus each of the 4 other treatment groups separately. Outcomes that were significantly different from AVA Alone group by the Wilcoxon Rank Sum test at $p<0.05$ are indicated by an asterisk in the tables.

All analyses included all 25 NHPs in the experiment. No adjustments for the multiple significance tests were made. The significance tests are provided to guide interpretation of the data only. The fact that there are only 5 animals in each group means that differences that may be clinically important will not necessarily be statistically significant. On the other hand, because of the multiple significance tests performed, some of the differences noted may be due to chance alone.

The geometric means of the anti-PA IgG titers on each day are shown in Table IV, along with the p-values comparing all 5 treatment groups. Numbers with an asterisk indicate that that group was significantly different at the 0.05 significance level from the AVA Alone group on that day. Some significant increases in geometric mean titers were noted when comparing groups receiving AVA in combination with a CpG ODN on Days 11, 16, 21, 28, 35, 42, and 49 compared to AVA Alone. The geometric means of the anti-PA IgG for all groups and all time points are plotted in FIG. 6.

TABLE IV

| | Anti-PA IgG Geometric Means Titer | | | | | |
|---|---|---|---|---|---|---|
| Study Day | AVA SQ | AVA + K SQ | AVA + 10103 SQ | AVA + 7909 SQ | AVA + 7909 IM | p-value** |
| 10 days pre | 224 | 1,935 | 282 | 538 | 75 | 0.47 |
| 1 | 136 | 72 | 1,420 | 247 | 55 | 0.77 |
| 4 | 381 | 633 | 318 | 243 | 18 | 0.84 |
| 11 | 10,850 | 35,558 | *69,896 | *70,334 | 28,685 | 0.059 |
| 16 | 72,922 | 119,545 | *538,025 | 183,630 | 212,095 | 0.059 |
| 21 | 35,370 | 61,983 | *310,753 | *127,623 | *165,425 | 0.029 |
| 28 | 94,204 | 114,936 | *325,414 | 119,436 | 93,301 | 0.101 |
| 35 | 119,719 | 182,093 | *319,666 | 227,795 | 59,609 | 0.018 |
| 42 | 45,397 | 63,868 | 97,958 | *184,346 | 61,636 | 0.24 |
| 49 | 4,323,503 | 1,541,858 | 8,143,388 | 1,563,387 | *926,026 | 0.058 |
| 56 | 808,048 | 1,324,476 | 1,340,915 | 2,698,954 | 2,014,763 | 0.26 |
| 63 | 859,924 | 508,446 | 1,867,685 | 653,155 | 670,124 | 0.21 |

*p < 0.05 in comparison to AVA sc, using the Wilcoxon Rank Sum test
**p-value based on Kruskal-Wallis test comparing all 5 treatment groups The earliest time a meaningful antibody titer was detected in animals was 11 days after the initial injection. Four of 5 and 5 of 5 animals receiving AVA+CpG 10103 SQ and AVA+CpG 7909 IM, respectively, had peak IgG concentrations at day 16. Whereas, 3 of 5, in the group receiving AVA+CpG 7909 SQ, and 2 of 5 in the groups receiving AVA alone or AVA+K type ODN had peak IgG concentrations at day 16. The remaining animals in these groups had peak concentrations at week 5. There was variability in responses between animals consistent with other vaccine preparations. As there were significant differences at some time points in each group receiving AVA with a CpG ODN, it appears that CpG ODN are increasing anti-PA antibody titers earlier during the immunization process.

Anti-PA IgM titers were determined by ELISA at baseline and up to 16 days after the first injection. FIG. 7 shows the geometric mean anti-PA IgM titers in all 5 study groups. The geometric mean TNA titer on each day is shown in Table V, along with the p-values comparing all 5 treatment groups. Numbers with an asterisk indicate that that group was significantly different at the 0.05 significance level from the AVA Alone group on that day. Significant differences were noted on days 4, 11, 16, 35, 42, and 56 (see also FIG. 8).

TABLE V

| | Geometric Mean TNA Titer | | | | | |
|---|---|---|---|---|---|---|
| Day | AVA SQ | AVA + K SQ | AVA + 10103 SQ | AVA + 7909 SQ | AVA + 7909 IM | p-value** |
| 4 | 750 | 564 | 818 | *278 | 674 | 0.10 |
| 11 | 709 | 3,990 | *5,880 | *6,659 | 2,295 | 0.04 |
| 16 | 9,923 | *40,130 | *36,453 | *84,737 | 13,095 | 0.003 |
| 21 | 30,566 | 49,148 | 38,805 | 67,262 | 24,579 | 0.13 |
| 28 | 58,216 | 46,442 | 102,761 | 137,442 | 31,483 | 0.07 |
| 35 | 32,348 | 39,984 | 59,652 | *168,815 | 24,991 | 0.04 |
| 42 | 20,409 | 29,759 | *68,738 | *80,926 | 17,593 | 0.02 |
| 49 | 1,170,338 | 403,990 | 1,492,207 | 885,196 | 1,135,368 | 0.12 |
| 56 | 227,357 | 195,412 | *914,143 | 262,595 | *472,711 | 0.01 |
| 63 | 464,681 | 246,756 | 598,617 | 313,282 | 414,113 | 0.20 |

*p < 0.05 in comparison to AVA sc, using the Wilcoxon Rank Sum test
**p-value based on Kruskal-Wallis test comparing all 5 treatment groups The correlation of TNA titers with anti-PA IgG titers was examined. Specifically, using linear regression models, TNA titer was plotted versus anti-PA IgG titer and correlation coefficients and probabilities were calculated. Correlations were statistically significant ($P<0.05$) between the titers of the two analytes on days 11, 21, 28, 35, 42, and 63.

Example 4

Mouse Seroprotection Assay

Mice were passively immunized with pooled serum collected from NHPs on days 11 and 16 post their first immunization. The four vaccine groups for which serum was pooled included AVA alone, AVA+CpG10103 SQ, AVA+CpG7909

SQ, and AVA+CpG7909 IM. Serum from a control group of untreated NHPs and from a pool of pre-treatment serum was also tested. Two experiments were performed (10 mice/group). Twenty-four hours after injecting mice IV with 0.1 mL of a pooled antiserum, serum was collected from 4 mice in each group and anti-PA IgG titers determined.

Mice were followed for survival after an i.p. challenge with 30-60 $LD_{50}$ of Sterne strain anthrax spores. Statistical analysis on survival data was performed using the log-rank test within the PROC LIFETEST of SAS software for Windows, Version 8.2. Table VI summarizes the percentage survival of treatment and control groups of mice in both experiments.

TABLE VI

Percentage Survival of Mice Post Injection with Pooled NHP Serum and Challenge with Anthrax Spores (N = 10 mice per group)

| | Experiment 1 | | Experiment 2 | |
|---|---|---|---|---|
| | Percentage Survival | | | |
| Vaccination Group | Day 11 serum | Day 16 serum | Day 11 serum | Day 16 serum |
| AVA | 10 | 50 | 10 | 20 |
| AVA + 10103 SQ | 40 | 40 | 0 | 60 |
| AVA + 7909 SQ | 60 | 70 | 40 | 40 |
| AVA + 7909 IM | 50 | 30 | 10 | 20 |
| Control | 0 | | 0 | |
| Pre-Treatment Bleed | 10 | | 10 | |

For NHP Serum Collected on Day 11 (two experiments combined), the survival curves were significantly different by the log-rank test when all 6 groups were included (p=0.0002), but were not significantly different when the 2 control groups were excluded (p=0.12). The pairwise analyses comparing the AVA-CpG combinations to AVA alone gave one significant result, for AVA+CpG7909 SQ (p 0.02). For NHP Serum Collected on Day 16 (two experiments combined), the survival curves were significantly different by the log-rank test when all 6 groups were included ($p<0.0001$), but were not significantly different when the 2 control groups were excluded (p=0.12). The pairwise analyses comparing the AVA-CpG combinations to AVA alone did not give any significant results.

Overall survival percentages for each treatment group were plotted versus the arithmetic mean anti-PA IgG titer of mouse sera collected for each treatment group 24 hours after injection of NHP serum just before anthrax spore challenge (FIG. 9). Linear regression was used to fit a line to the data points to be used as a predictor of the serum titer needed to be circulating in mice at the time of challenge to achieve protection against an injection of 30 to 60 $LD_{50}$ of anthrax spores. The two data points with titers above 6,000 were excluded from the calculation of the regression line. Interpolating from the regression line, this data suggest that it takes a circulating anti-PA IgG titer of 2,500 to protect 50% of mice from a lethal challenge of 30 to 60 $LD_{50}$ of anthrax spores.

Thus, CpG ODN can be safely administered in amounts of 250 μg in combination with the approved human dose of AVA to rhesus macaques. The combination of CpG ODN with AVA increased the total anti-PA IgG concentration after a single priming immunization compared to the group receiving AVA alone. The peak response was also accelerated in time for more of the animals receiving AVA+CpG 10103 and CpG 7909 compared to AVA alone. Although antibody titers were statistically significantly increased at some time points in some of the groups immunized with AVA in combination with CpG ODN compared to AVA alone, the numbers of animals per group were relatively small, and therefore, the statistical significance of these results should be viewed with caution. However, the results overall are highly encouraging that this combination may potentiate the development of protective antibodies when B type CpG are combined with the licensed anthrax vaccine.

Example 5

Effect of CpG ODN on the Protective Efficacy of AVA

The critical measure of an antigen-adjuvant combination is its ability to induce protective immunity. Based on results indicating that the immune response of macaques to AVA was improved by the co-administration of CpG ODN, studies to demonstrate the protective efficacy of CpG ODN with AVA were undertaken. Due to restrictions associated with the use of macaques in trials involving lethal anthrax challenge, the widely accepted guinea pig model was employed. Normal guinea pigs succumb rapidly to challenge by 50 LD50 Ames strain anthrax spores (Table VII). Immunization and boosting with AVA alone improved survival, although most animals still died from infection (Table III). By comparison, nearly 75% of the animals immunized and boosted with CpG-adjuvanted vaccine survived (p=0.05). Co-administering CpG ODN with AVA also resulted in a modest increase in the MID of the challenged animals, although this effect did not reach statistical significance.

TABLE VII

Effect of CpG ODN plus AVA on the survival of guinea pigs challenged with anthrax

| | # Surviving/total | % Surviving | MTD (days) |
|---|---|---|---|
| Untreated | 1/28 | 3.6 | 2.1 |
| AVA | 15/32 | 46.9 | 6.1 |
| AVA + CpG ODN | 23/31* | 74.2 | 6.9 |

Guinea pigs were immunized on day 0 and boosted on week 4 with AVA plus 100-300 μg of an equimolar mixture of CpG D ODNs 1555, 1466 and K3 (all known to be active in this species). Six weeks later they were challenged IM with 50 LD50 Ames spores. Survival and mean time to death (MTD in days) is shown.
*Significantly improved survival compared to animals immunized with AVA alone, p = 0.05.

The fraction of guinea pigs surviving otherwise lethal anthrax challenge was significantly improved by co-administration of CpG ODN with AVA. Without being bound by theory, several characteristics of CpG ODN contribute to their utility as immunotherapeutic agents. First, a single dose can provide protection for several weeks, allowing ODN to be administered to "at risk" populations (e.g., medical and/or military personnel) in advance of potential pathogen exposure (Elkins et al., *J. Immunol.* 162:2291, 1999). Repeated doses can extend the duration of protection for many months (Klinman et al., *Infect. Immun.* 67:5658, 1999). Second, CpG ODN are effective against a wide range of pathogens, and thus may be of use before the causative agent has been identified. Third, CpG ODN improve the innate immune response of individuals whose adaptive immune response is impaired (such as newborns and the elderly), and thus can provide broad population-based protection against infection (Klinman et al., *Immunity* 11:123, 1999).

Furthermore, repeated doses of CpG ODN can be safely administered to rodents and primates without adverse consequences (Verthelyi et al., *J. Immunol.* 168:1659, 2002; Klinman et al., *Infect. Immun.* 67:565, 1999). In the present example, animals treated with CpG ODN (alone or in combination with anthrax vaccine) remained healthy and active prior to pathogen challenge.

Example 6

Dose and Timing of CpG Administration Influences CpG-Mediated Protection in Mice Exposed to Ebola Virus In order to demonstrate the effect of CpG dosage on protection from Ebola virus, mice were treated with 25-150 µg of CpG ODN on day 0, and then challenged with 300 LD50 of mouse-adapted Ebola Zaire. As shown in FIG. 3*a*, mice treated with 100-150 µg of CpG ODN attained maximal protection from the virus.

In order to determine the effect of timing of CpG administration on protection from Ebola, mice were treated with 100 µg of CpG ODN on the day shown, and then challenged with 300 LD50 of mouse-adapted Ebola Zaire. As shown in FIG. 3*b*, mice showed maximal protection from Ebola infection when CpG ODN were administered concurrently with Ebola exposure. However, partial protection was attained when CpG ODN were administered up to three days prior to exposure or up to three days after exposure.

Example 7

CpG ODNs Increase Survival Times in Mice Exposed to Anthrax Spores

In order to demonstrate that CpG ODNs increase survival times in mice exposed to anthrax spores, mice were treated at the times shown with 100 µg of CpG ODN, and then challenged with 11 LD 50 anthrax spores. As shown in FIG. 4, CpG administration increased survival times in mice exposed to anthrax spores.

Example 8

Adjuvant Effect of CpG ODN with AVA/rPA in Mice

This example demonstrates the adjuvant effect of CpG ODN with AVA/rPA in mice. Mice were immunized with 2.5 µg of rPA or 5 µg of AVA plus 50 µg of CpG ODN. The magnitude of the IgG anti-PA response and IFNγ response 10 days after the second immunization is shown below (N=4 mice/group).

TABLE VIII

Effect of CpG ODN on the immune response of mice to AVA and rPA

| Group | IgG anti-PA titer (×1000) | IFNγ production |
|---|---|---|
| Naive | 0 | 0 |
| AVA | 13 + 8 | 250 + 125 |
| AVA + CpG | 15 + 12 | 757~87 |
| rPA | 45 + 3 | 254 + 163 |
| rPA + CpG | 182 + 61 | 343 + 148 |
| CpG | 0 | 0 |

Example 9

Effect of CpG ODN Alone (No Antigen) to Prevent Infection by TBEV

This example demonstrates the efficacy of CpG ODN alone in preventing infection by tick-borne encephalitis virus. Mice were injection on the day shown with 100 µg of CpG ODN. They were challenged with TBEC, and survival monitored. N=10/group.

TABLE IX

Effect of CpG ODN on the immune response of mice to tick borne encephalitis virus

| Group | Percent surviving (day 12) |
|---|---|
| Control ODN | 0 |
| CpG ODN day 0 | 80 |
| CpG ODN day 2 | 30 |
| CpG ODN day 4 | 20 |

Example 10

Effect of K ODN on the Avidity of the Anti-PA Response

This example demonstrates the effect of K ODN on the avidity of the anti-PA response. Animals were treated with ODN as described in Elkins et al., *J. Immunol* 162:2291, 1999. FIG. 5 shows that K ODN increase the avidity of the anti-PA response.

Example 11

Effect of Poly (Lactide-Co-gGycolide) (PLG) Microparticle

Formulation of DNA onto cationic poly(lactide-coglycolide) (PLG) microparticles, has been developed as a means to better target DNA to antigen-presenting cells (APCs). PLG microparticles are an attractive approach for vaccine delivery, since the polymer is biodegradable and biocompatible and has been used to develop several drug delivery systems (Okada et al, *Adv. Drug Deliv. Rev.* 28:43-70, 1997). In addition, PLG microparticles have also been used for a number of years as delivery systems for entrapped vaccine antigens (Singh and O'Hanagan, *Nat. Biotechnol.* 17:1075-1081, 1999). More recently, PLG microparticles have been described as a delivery system for vaccines, such as entrapped DNA vaccines (Hedley et al., *Nat. Med.* 4:365-368, 1998; Jones et al., *Vaccine* 15:814-817, 1997; U.S. Pat. No. 6,309,569; U.S. Pat. No. 6,565,777; U.S. Pat. No. 6,548,302).

Encapsulating a bioactive agent in a polymer microparticle, such as a PLG microparticle generally includes (1) dissolving polymer in a solvent to form a polymer solution; (2) preparing an aqueous solution of the bioactive agent, such as the CpG ODN; (3) combining the polymer and bioactive agent solutions with agitation to form a water-in-oil emulsion; (4) adding the water-in-oil emulsion to a further aqueous phase containing a stabilizer or surfactant with agitation to form a (water-in-oil)-in-water emulsion; (5) adding the (water-in-oil)-in-water emulsion to excess of an aqueous phase to extract the solvent, thereby forming polymer microparticles of a size up to 10 microns in diameter. The microparticles contain the bioactive agent. Generally, the polymer includes or consists of PLG of molecular weight of 40 kD or lower (see U.S. Pat. No. 6,309,569). In one example, the molecular weight of the PLG is 30 kD or lower. In other examples, the microparticles include PLG of 3 kD, 6 kD, 9 kD, 22 kD and mixtures thereof. It has been proposed that the molecular weight range of suitable polymer is 1.5 kD-250 kD, and commercial preparations of 3, 6, 9, 12, 18, 22, 60, 65 & 90 kD PLG have been utilized (see U.S. Pat. No. 5,309,569). It is believed that the hydrolysis rate of the polymer is related to the molecular weight. Thus, lower molecular weight polymers degrade more rapidly.

The effectiveness of cationic microparticles with adsorbed DNA at inducing immune responses was investigated in mice. The PLG polymer (RG505) can be obtained from Boehringer Ingelheim.

Several exemplary protocol for the preparation of cationic microparticles using a modified solvent evaporation process follows.

1. Briefly, the microparticles were prepared by emulsifying 10 ml of a 5% (wt/vol) polymer solution in methylene chloride with 1 ml of phosphate-buffered saline (PBS) at high speed using an IKA homogenizer. The primary emulsion was then added to 50 ml of distilled water containing cetyltrimethylammonium bromide (CTAB) (0.5% wt/vol), resulting in the formation of a water-in-oil-in-water emulsion, which was stirred at 6,000 rpm for 12 hours at room temperature, allowing the methylene chloride to evaporate. The resulting microparticles were washed twice in distilled water by centrifugation at 10,000×g and freeze-dried. DNA was adsorbed onto the microparticles by incubating 100 mg of cationic microparticles in a I-mg/ml solution of DNA at 4° C. for 6 hours. The microparticles were then separated by centrifugation, the pellet was washed with TE (Tris-EDTA) buffer, and the microparticles were freeze-dried. Physical characteristics were monitored as previously described (see Singh et al., *Proc. Natl. Acad. Sci. USA* 97:811-816; O'Hagan et al., *J. Virol.* 75 (19):9037-9043, 2001).
2. Cationic microparticles were prepared by using a modified solvent evaporation process. Briefly, the microparticles were prepared by emulsifying 10 ml of a 5% (wt/vol) polymer solution in methylene chloride with 1 ml of PBS at high speed using an Ika homogenizer (Ika-Werk Instruments, Cincinnati, Ohio). The primary emulsion then was added to 50 ml of distilled water containing cetyltrimethylammonium bromide (CTAB) (0.5% wt/vol). This resulted in the formation of a water/oil/water emulsion that was stirred at 6,000 rpm for 12 hours at room temperature, allowing the methylene chloride to evaporate. The resulting microparticles were washed twice in distilled water by centrifugation at 10,000 g and freeze-dried. For preparing PLG-dimethyl dioctadecyl ammonium bromide (DDA) and PLG-1,2-dioleoyl-1,3-trimethylammoniopropane (DOTAP) microparticles, DDA or DOTAP was dissolved in the polymer solution along with PLG polymer, and the primary emulsion then was added to 0.5% polyvinyl alcohol solution to form the water/oil/water emulsion (see Singh et al., *Proc. Natl. Acad. Sci.* 97:811-816, 2000).

After preparation, washing, and collection, DNA was adsorbed onto the microparticles by incubating 100 mg of cationic microparticles in a 1 mg/ml solution of DNA at 4° C. for 6 hours. The microparticles then were separated by centrifugation, the pellet was washed with Tris-EDTA buffer, and the microparticles were freeze-dried (see Singh et al., *Proc. Natl. Acad. Sci.* 97:811-816, 2000).

For the studies described below, the CpG ODN was conjugated to the PLG, whereas the rPA was free (but was co-administered after mixing with the PLG-ODN).

Mice were immunized with either 2.5, 8 or 25 μl of AVA, AVA plus CpG ODN, AVA plus PLG-CpG, AVA plus GpC ODN (a control), AVA plus PLG-GpG ODN (and additional control), or AVA plus PLG (a further control). The IgM anti-PA titer, IgG anti-PA titer, IgG1 anti-PA titer, IgG2a anti-PA titer, and survival of the animals were monitored.

The results indicated that mice immunized with a single dose of AVA plus CpG or poly (lactide-co-glycolide) microparticle (PLG)-encapsulated CpG through cross-linking developed specific antibody responses as early as day 11 post-immunization. The antibody response elicited by the AVA-CpG-ODN immunogen was five to one hundred times greater than that of mice immunized with AVA alone or AVA plus control ODN or PLG-control ODN. Immunization of AVA plus CpG or PLG-CpG also elicited a stronger TH1 response with higher ratios of IgG2a/IgG1 than control groups. Whereas most of control mice died after a challenge with 300-9000 LD50 of Sterne strain spores (STI) of *Bacillus anthracis* at week 1 and 2 post-immunization, a 70-100% survival rate was observed in mice immunized with AVA plus CpG or PLG-CpG. These results suggested that using CpG or PLG-CpG as adjuvants not only improved the immunogenicity and protection of AVA against STI spore challenge, but also accelerated specific immune responses with great potential for counter-bioterrorism usage.

It will be apparent that the precise details of the methods or compositions described may be varied or modified without departing from the spirit of the described disclosure. We claim all such modifications and variations that fall within the scope and spirit of the claims below.

The invention claimed is:

1. A method of enhancing the immunogenicity of a vaccine against *Bacillus anthracis* in a subject, comprising administering to the subject a therapeutically effective amount of an oligodeoxynucleotide consisting of the nucleic acid sequence set forth as SEQ ID NO: 200 in combination with the vaccine against *Bacillus anthracis*, thereby enhancing the immunogenicity of the vaccine.

2. The method of claim 1, wherein the vaccine is an antigen vaccine, a DNA vaccine, a protein subunit vaccine, a peptide vaccine, an attenuated vaccine, or a heat-killed vaccine.

3. The method of claim 1, wherein the vaccine is an antigen from *Bacillus anthracis*.

4. The method of claim 3, wherein the antigen is recombinant Protective Antigen or Protective Antigen.

5. The method of claim 1, wherein the oligodeoxynucleotide is administered before the vaccine is administered to the subject.

6. The method of claim 5, wherein the oligodeoxynucleotide is administered from about two weeks to about one day before the vaccine is administered to the subject.

7. The method of claim 1, wherein the oligodeoxynucleotide is administered to the subject concurrently with the vaccine.

8. The method of claim 1, wherein the oligodeoxynucleotide is administered after the vaccine is administered to the subject.

9. The method of claim 8, wherein the oligodeoxynucleotide is administered from about two weeks to about one day after the vaccine is administered to the subject.

10. A method of enhancing the immunogenicity of Anthrax Vaccine Adsorbed (AVA) vaccine, comprising administering to a subject a therapeutically effective amount of an oligodeoxynucleotide comprising the nucleotide sequence set forth as SEQ ID NO: 200 and a therapeutically effective amount of Anthrax Vaccine Adsorbed (AVA) vaccine, thereby enhancing the immunogenicity of Anthrax Vaccine Adsorbed (AVA) vaccine.

11. A method of enhancing the immunogenicity of a vaccine comprising anthrax protective antigen, comprising administering to a subject a therapeutically effective amount of an oligodeoxynucleotide comprising the nucleotide sequence set forth as SEQ ID NO: 200 and a therapeutically effective amount of anthrax protective antigen, thereby enhancing the immunogenicity of the vaccine.

12. The method of claim 10, wherein enhancing the immunogenicity of AVA comprises increasing the IgG or IgM titer.

13. The method of claim 10, wherein enhancing the immunogenicity of AVA comprises increasing survival of the subject upon subsequent exposure to anthrax.

14. The method of claim 1, wherein the vaccine is Anthrax Vaccine Adsorbed (AVA).

15. The method of claim 11, wherein the subject is human.

16. The method of claim 14, comprising administering to the subject a therapeutically effective amount of the oligodeoxynucleotide and a therapeutically effective amount of anthrax protective antigen at an initial time point and at two and four weeks following the initial time point, thereby enhancing the immunogenicity of the vaccine.

17. The method of claim 1, wherein the subject is human.

18. The method of claim 1, comprising administering to the subject a therapeutically effective amount of the oligodeoxynucleotide and a therapeutically effective amount of anthrax protective antigen at an initial time point and at two and four weeks following the initial time point, thereby enhancing the immunogenicity of the vaccine.

19. A method of enhancing the immunogenicity of a vaccine against *Bacillus anthracis* in a subject, comprising administering to the subject a therapeutically effective amount of an oligodeoxynucleotide comprising the nucleic acid sequence set forth as SEQ ID NO: 200 in combination with the vaccine against *Bacillus anthracis*, thereby enhancing the immunogenicity of the vaccine.

20. The method of claim 19, wherein the vaccine is an antigen vaccine, a DNA vaccine, a protein subunit vaccine, a peptide vaccine, an attenuated vaccine, or a heat-killed vaccine.

21. The method of claim 19, wherein the vaccine is an antigen from *Bacillus anthracis*.

22. The method of claim 19, wherein the antigen is recombinant Protective Antigen or Protective Antigen.

23. The method of claim 19, wherein the oligodeoxynucleotide is administered before the vaccine is administered to the subject.

24. The method of claim 19, wherein the oligodeoxynucleotide is administered from about two weeks to about one day before the vaccine is administered to the subject.

25. The method of claim 19, wherein the oligodeoxynucleotide is administered to the subject concurrently with the vaccine.

26. The method of claim 19, wherein the oligodeoxynucleotide is administered after the vaccine is administered to the subject.

27. The method of claim 19, wherein the oligodeoxynucleotide is administered from about two weeks to about one day after the vaccine is administered to the subject.

* * * * *

SEQUENCE LISTING

```
<160> NUMBER OF SEQ ID NOS: 200

<210> SEQ ID NO 1
<211> LENGTH: 20
<212> TYPE: DNA
<213> ORGANISM: Artificial sequence
<220> FEATURE:
<223> OTHER INFORMATION: CpG D oligonucleotide
<220> FEATURE:
<221> NAME/KEY: misc_feature
<222> LOCATION: (1)..(2)
<223> OTHER INFORMATION: n is any base, or no base at all

<400> SEQUENCE: 1

nntgcatcga tgcagggggg                                                   20
```

<210> SEQ ID NO 2
<211> LENGTH: 20
<212> TYPE: DNA
<213> ORGANISM: Artificial sequence
<220> FEATURE:
<223> OTHER INFORMATION: CpG D oligonucleotide
<220> FEATURE:
<221> NAME/KEY: misc_feature
<222> LOCATION: (1)..(2)
<223> OTHER INFORMATION: n is any base, or no base at all

<400> SEQUENCE: 2
nntgcaccgg tgcagggggg 20

<210> SEQ ID NO 3
<211> LENGTH: 20
<212> TYPE: DNA
<213> ORGANISM: Artificial sequence
<220> FEATURE:
<223> OTHER INFORMATION: CpG D oligonucleotide
<220> FEATURE:
<221> NAME/KEY: misc_feature
<222> LOCATION: (1)..(2)
<223> OTHER INFORMATION: n is any base, or no base at all

<400> SEQUENCE: 3
nntgcgtcga cgcagggggg 20

<210> SEQ ID NO 4
<211> LENGTH: 20
<212> TYPE: DNA
<213> ORGANISM: Artificial sequence
<220> FEATURE:
<223> OTHER INFORMATION: CpG D oligonucleotide
<220> FEATURE:
<221> NAME/KEY: misc_feature
<222> LOCATION: (1)..(2)
<223> OTHER INFORMATION: n is any base, or no base at all

<400> SEQUENCE: 4
nntgcgtcga tgcagggggg 20

<210> SEQ ID NO 5
<211> LENGTH: 20
<212> TYPE: DNA
<213> ORGANISM: Artificial sequence
<220> FEATURE:
<223> OTHER INFORMATION: CpG D oligonucleotide
<220> FEATURE:
<221> NAME/KEY: misc_feature
<222> LOCATION: (1)..(2)
<223> OTHER INFORMATION: n is any base, or no base at all

<400> SEQUENCE: 5
nntgcgccgg cgcagggggg 20

<210> SEQ ID NO 6
<211> LENGTH: 20
<212> TYPE: DNA
<213> ORGANISM: Artificial sequence
<220> FEATURE:
<223> OTHER INFORMATION: CpG D oligonucleotide
<220> FEATURE:
<221> NAME/KEY: misc_feature
<222> LOCATION: (1)..(2)
<223> OTHER INFORMATION: n is any base, or no base at all

<400> SEQUENCE: 6

-continued

```
nntgcgccga tgcagggggg                                                  20


<210> SEQ ID NO 7
<211> LENGTH: 20
<212> TYPE: DNA
<213> ORGANISM: Artificial sequence
<220> FEATURE:
<223> OTHER INFORMATION: CpG D oligonucleotide
<220> FEATURE:
<221> NAME/KEY: misc_feature
<222> LOCATION: (1)..(2)
<223> OTHER INFORMATION: n is any base, or no base at all

<400> SEQUENCE: 7

nntgcatcga cgcagggggg                                                  20


<210> SEQ ID NO 8
<211> LENGTH: 20
<212> TYPE: DNA
<213> ORGANISM: Artificial sequence
<220> FEATURE:
<223> OTHER INFORMATION: CpG D oligonucleotide
<220> FEATURE:
<221> NAME/KEY: misc_feature
<222> LOCATION: (1)..(2)
<223> OTHER INFORMATION: n is any base, or no base at all

<400> SEQUENCE: 8

nntgcgtcgg tgcagggggg                                                  20


<210> SEQ ID NO 9
<211> LENGTH: 6
<212> TYPE: DNA
<213> ORGANISM: Artificial sequence
<220> FEATURE:
<223> OTHER INFORMATION: CpG D oligonucleotide

<400> SEQUENCE: 9

atcgat                                                                  6


<210> SEQ ID NO 10
<211> LENGTH: 6
<212> TYPE: DNA
<213> ORGANISM: Artificial sequence
<220> FEATURE:
<223> OTHER INFORMATION: CpG D oligonucleotide

<400> SEQUENCE: 10

accggt                                                                  6


<210> SEQ ID NO 11
<211> LENGTH: 6
<212> TYPE: DNA
<213> ORGANISM: Artificial sequence
<220> FEATURE:
<223> OTHER INFORMATION: CpG D oligonucleotide

<400> SEQUENCE: 11

atcgac                                                                  6


<210> SEQ ID NO 12
<211> LENGTH: 6
<212> TYPE: DNA
<213> ORGANISM: Artificial sequence
<220> FEATURE:
<223> OTHER INFORMATION: CpG D oligonucleotide

<400> SEQUENCE: 12
```

accgat 6

<210> SEQ ID NO 13
<211> LENGTH: 6
<212> TYPE: DNA
<213> ORGANISM: Artificial sequence
<220> FEATURE:
<223> OTHER INFORMATION: CpG D oligonucleotide

<400> SEQUENCE: 13 gtcgac 6

<210> SEQ ID NO 14
<211> LENGTH: 6
<212> TYPE: DNA
<213> ORGANISM: Artificial sequence
<220> FEATURE:
<223> OTHER INFORMATION: CpG D oligonucleotide

<400> SEQUENCE: 14 gccggc 6

<210> SEQ ID NO 15
<211> LENGTH: 20
<212> TYPE: DNA
<213> ORGANISM: Artificial sequence
<220> FEATURE:
<223> OTHER INFORMATION: CpG D oligonucleotide

<400> SEQUENCE: 15
ggtgcatcga tacagggggg 20

<210> SEQ ID NO 16
<211> LENGTH: 20
<212> TYPE: DNA
<213> ORGANISM: Artificial sequence
<220> FEATURE:
<223> OTHER INFORMATION: CpG D oligonucleotide

<400> SEQUENCE: 16
ggtgcgtcga tgcagggggg 20

<210> SEQ ID NO 17
<211> LENGTH: 15
<212> TYPE: DNA
<213> ORGANISM: Artificial sequence
<220> FEATURE:
<223> OTHER INFORMATION: CpG D oligonucleotide

<400> SEQUENCE: 17
gctagacgtt agcgt 15

<210> SEQ ID NO 18
<211> LENGTH: 10
<212> TYPE: DNA
<213> ORGANISM: Artificial sequence
<220> FEATURE:
<223> OTHER INFORMATION: CpG D oligonucleotide

<400> SEQUENCE: 18
tcaacgttga 10

<210> SEQ ID NO 19
<211> LENGTH: 15
<212> TYPE: DNA

-continued

```
<213> ORGANISM: Artificial sequence
<220> FEATURE:
<223> OTHER INFORMATION: Control D oligonucleotide

<400> SEQUENCE: 19

gctagagctt aggct                                                        15


<210> SEQ ID NO 20
<211> LENGTH: 10
<212> TYPE: DNA
<213> ORGANISM: Artificial sequence
<220> FEATURE:
<223> OTHER INFORMATION: Control D oligonucleotide

<400> SEQUENCE: 20

tcaagcttga                                                              10


<210> SEQ ID NO 21
<211> LENGTH: 20
<212> TYPE: DNA
<213> ORGANISM: Artificial sequence
<220> FEATURE:
<223> OTHER INFORMATION: CpG D oligonucleotide

<400> SEQUENCE: 21

ggtgcatcga tgcagggggg                                                   20


<210> SEQ ID NO 22
<211> LENGTH: 20
<212> TYPE: DNA
<213> ORGANISM: Artificial sequence
<220> FEATURE:
<223> OTHER INFORMATION: CpG D oligonucleotide

<400> SEQUENCE: 22

ggtgcaccgg tgcagggggg                                                   20


<210> SEQ ID NO 23
<211> LENGTH: 20
<212> TYPE: DNA
<213> ORGANISM: Artificial sequence
<220> FEATURE:
<223> OTHER INFORMATION: CpG D oligonucleotide

<400> SEQUENCE: 23

atcgactctc gagcgttctc                                                   20


<210> SEQ ID NO 24
<211> LENGTH: 12
<212> TYPE: DNA
<213> ORGANISM: Artificial sequence
<220> FEATURE:
<223> OTHER INFORMATION: CpG D oligonucleotide

<400> SEQUENCE: 24

tcgttcgttc tc                                                           12


<210> SEQ ID NO 25
<211> LENGTH: 12
<212> TYPE: DNA
<213> ORGANISM: Artificial sequence
<220> FEATURE:
<223> OTHER INFORMATION: CpG D oligonucleotide

<400> SEQUENCE: 25

tcgagcgttc tc                                                           12
```

-continued

<210> SEQ ID NO 26
<211> LENGTH: 20
<212> TYPE: DNA
<213> ORGANISM: Artificial sequence
<220> FEATURE:
<223> OTHER INFORMATION: Control D oligonucleotide

<400> SEQUENCE: 26
ggtgcattga tgcagggggg 20

<210> SEQ ID NO 27
<211> LENGTH: 12
<212> TYPE: DNA
<213> ORGANISM: Artificial sequence
<220> FEATURE:
<223> OTHER INFORMATION: Control D oligonucleotide

<400> SEQUENCE: 27
ttgagtgttc tc 12

<210> SEQ ID NO 28
<211> LENGTH: 16
<212> TYPE: DNA
<213> ORGANISM: Artificial sequence
<220> FEATURE:
<223> OTHER INFORMATION: Control D oligonucleotide

<400> SEQUENCE: 28
gggcatgcat gggggg 16

<210> SEQ ID NO 29
<211> LENGTH: 20
<212> TYPE: DNA
<213> ORGANISM: Artificial sequence
<220> FEATURE:
<223> OTHER INFORMATION: K oligonucleotide

<400> SEQUENCE: 29
tccatgtcgc tcctgatgct 20

<210> SEQ ID NO 30
<211> LENGTH: 20
<212> TYPE: DNA
<213> ORGANISM: Artificial sequence
<220> FEATURE:
<223> OTHER INFORMATION: K oligonucleotide

<400> SEQUENCE: 30
tccatgtcgt tcctgatgct 20

<210> SEQ ID NO 31
<211> LENGTH: 23
<212> TYPE: DNA
<213> ORGANISM: Artificial sequence
<220> FEATURE:
<223> OTHER INFORMATION: K oligonucleotide

<400> SEQUENCE: 31
tcgtcgtttt gtcgttttgt cgt 23

<210> SEQ ID NO 32
<211> LENGTH: 20
<212> TYPE: DNA
<213> ORGANISM: Artificial sequence
<220> FEATURE:

<223> OTHER INFORMATION: K oligonucleotide

<400> SEQUENCE: 32
tcgtcgttgt cgttgtcgtt 20

<210> SEQ ID NO 33
<211> LENGTH: 23
<212> TYPE: DNA
<213> ORGANISM: Artificial sequence
<220> FEATURE:
<223> OTHER INFORMATION: K oligonucleotide

<400> SEQUENCE: 33
tcgtcgtttt gtcgtttgtc gtt 23

<210> SEQ ID NO 34
<211> LENGTH: 22
<212> TYPE: DNA
<213> ORGANISM: Artificial sequence
<220> FEATURE:
<223> OTHER INFORMATION: K oligonucleotide

<400> SEQUENCE: 34
tcgtcgttgt cgttttgtcg tt 22

<210> SEQ ID NO 35
<211> LENGTH: 21
<212> TYPE: DNA
<213> ORGANISM: Artificial sequence
<220> FEATURE:
<223> OTHER INFORMATION: K oligonucleotide

<400> SEQUENCE: 35
gcgtgcgttg tcgttgtcgt t 21

<210> SEQ ID NO 36
<211> LENGTH: 21
<212> TYPE: DNA
<213> ORGANISM: Artificial sequence
<220> FEATURE:
<223> OTHER INFORMATION: K oligonucleotide

<400> SEQUENCE: 36
tgtcgtttgt cgtttgtcgt t 21

<210> SEQ ID NO 37
<211> LENGTH: 19
<212> TYPE: DNA
<213> ORGANISM: Artificial sequence
<220> FEATURE:
<223> OTHER INFORMATION: K oligonucleotide

<400> SEQUENCE: 37
tgtcgttgtc gttgtcgtt 19

<210> SEQ ID NO 38
<211> LENGTH: 14
<212> TYPE: DNA
<213> ORGANISM: Artificial sequence
<220> FEATURE:
<223> OTHER INFORMATION: K oligonucleotide

<400> SEQUENCE: 38
tcgtcgtcgt cgtt 14

```
<210> SEQ ID NO 39
<211> LENGTH: 20
<212> TYPE: DNA
<213> ORGANISM: Artificial sequence
<220> FEATURE:
<223> OTHER INFORMATION: K oligonucleotide

<400> SEQUENCE: 39

tcctgtcgtt ccttgtcgtt                                                  20


<210> SEQ ID NO 40
<211> LENGTH: 20
<212> TYPE: DNA
<213> ORGANISM: Artificial sequence
<220> FEATURE:
<223> OTHER INFORMATION: K oligonucleotide

<400> SEQUENCE: 40

tcctgtcgtt ttttgtcgtt                                                  20


<210> SEQ ID NO 41
<211> LENGTH: 21
<212> TYPE: DNA
<213> ORGANISM: Artificial sequence
<220> FEATURE:
<223> OTHER INFORMATION: K oligonucleotide

<400> SEQUENCE: 41

tcgtcgctgt ctgcccttct t                                                21


<210> SEQ ID NO 42
<211> LENGTH: 21
<212> TYPE: DNA
<213> ORGANISM: Artificial sequence
<220> FEATURE:
<223> OTHER INFORMATION: K oligonucleotide

<400> SEQUENCE: 42

tcgtcgctgt tgtcgtttct t                                                21


<210> SEQ ID NO 43
<211> LENGTH: 20
<212> TYPE: DNA
<213> ORGANISM: Artificial sequence
<220> FEATURE:
<223> OTHER INFORMATION: K oligonucleotide

<400> SEQUENCE: 43

tccatgacgt tcctgacgtt                                                  20


<210> SEQ ID NO 44
<211> LENGTH: 16
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 44

nnnrycgryn nngggg                                                      16
```

```
<210> SEQ ID NO 45
<211> LENGTH: 17
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t

<400> SEQUENCE: 45

nnnrycgryn nnngggg                                                    17


<210> SEQ ID NO 46
<211> LENGTH: 18
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(14)
<223> OTHER INFORMATION: n is a, c, g, or t

<400> SEQUENCE: 46

nnnrycgryn nnnngggg                                                   18


<210> SEQ ID NO 47
<211> LENGTH: 19
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(15)
<223> OTHER INFORMATION: n is a, c, g, or t

<400> SEQUENCE: 47

nnnrycgryn nnnnngggg                                                  19


<210> SEQ ID NO 48
<211> LENGTH: 20
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(16)
<223> OTHER INFORMATION: n is a, c, g, or t

<400> SEQUENCE: 48

nnnrycgryn nnnnnngggg                                                 20
```

<210> SEQ ID NO 49
<211> LENGTH: 21
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(17)
<223> OTHER INFORMATION: n is a, c, g, or t

<400> SEQUENCE: 49
nnnrycgryn nnnnnnnggg g 21

<210> SEQ ID NO 50
<211> LENGTH: 22
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(18)
<223> OTHER INFORMATION: n is a, c, g, or t

<400> SEQUENCE: 50
nnnrycgryn nnnnnnnngg gg 22

<210> SEQ ID NO 51
<211> LENGTH: 23
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(19)
<223> OTHER INFORMATION: n is a, c, g, or t

<400> SEQUENCE: 51
nnnrycgryn nnnnnnnnng ggg 23

<210> SEQ ID NO 52
<211> LENGTH: 24
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t

<400> SEQUENCE: 52
nnnrycgryn nnnnnnnnnn gggg 24

<210> SEQ ID NO 53
<211> LENGTH: 25
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(21)
<223> OTHER INFORMATION: n is a, c, g, or t

<400> SEQUENCE: 53
nnnrycgryn nnnnnnnnnn ngggg 25

<210> SEQ ID NO 54
<211> LENGTH: 26
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(22)
<223> OTHER INFORMATION: n is a, c, g, or t

<400> SEQUENCE: 54
nnnrycgryn nnnnnnnnnn nngggg 26

<210> SEQ ID NO 55
<211> LENGTH: 17
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 55
nnnrycgryn nngggg 17

<210> SEQ ID NO 56
<211> LENGTH: 18
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t

<400> SEQUENCE: 56
nnnrycgryn nnnggggg 18

<210> SEQ ID NO 57
<211> LENGTH: 19
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(14)
<223> OTHER INFORMATION: n is a, c, g, or t

<400> SEQUENCE: 57
nnnrycgryn nnnnggggg 19

<210> SEQ ID NO 58
<211> LENGTH: 20
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(15)
<223> OTHER INFORMATION: n is a, c, g, or t

<400> SEQUENCE: 58
nnnrycgryn nnnnnggggg 20

<210> SEQ ID NO 59
<211> LENGTH: 21
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(16)
<223> OTHER INFORMATION: n is a, c, g, or t

<400> SEQUENCE: 59
nnnrycgryn nnnnnngggg g 21

<210> SEQ ID NO 60
<211> LENGTH: 22
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(17)
<223> OTHER INFORMATION: n is a, c, g, or t

<400> SEQUENCE: 60
nnnrycgryn nnnnnnnggg gg 22

<210> SEQ ID NO 61
<211> LENGTH: 23
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(18)
<223> OTHER INFORMATION: n is a, c, g, or t

<400> SEQUENCE: 61
nnnrycgryn nnnnnnnngg ggg 23

<210> SEQ ID NO 62
<211> LENGTH: 24
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(19)
<223> OTHER INFORMATION: n is a, c, g, or t

<400> SEQUENCE: 62
nnnrycgryn nnnnnnnnng gggg 24

<210> SEQ ID NO 63
<211> LENGTH: 25
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t

<400> SEQUENCE: 63
nnnrycgryn nnnnnnnnnn ggggg 25

<210> SEQ ID NO 64
<211> LENGTH: 26
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(21)
<223> OTHER INFORMATION: n is a, c, g, or t

<400> SEQUENCE: 64
nnnrycgryn nnnnnnnnnn nggggg 26

<210> SEQ ID NO 65
<211> LENGTH: 27
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(22)
<223> OTHER INFORMATION: n is a, c, g, or t

<400> SEQUENCE: 65
nnnrycgryn nnnnnnnnnn nngggggg 27

<210> SEQ ID NO 66
<211> LENGTH: 18
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 66
nnnrycgryn nngggggg 18

<210> SEQ ID NO 67
<211> LENGTH: 19
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t

<400> SEQUENCE: 67
nnnrycgryn nnngggggg 19

<210> SEQ ID NO 68
<211> LENGTH: 20
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(14)

-continued

<223> OTHER INFORMATION: n is a, c, g, or t

<400> SEQUENCE: 68
nnnrycgryn nnnngggggg 20

<210> SEQ ID NO 69
<211> LENGTH: 21
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(15)
<223> OTHER INFORMATION: n is a, c, g, or t

<400> SEQUENCE: 69
nnnrycgryn nnnnnggggg g 21

<210> SEQ ID NO 70
<211> LENGTH: 22
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(16)
<223> OTHER INFORMATION: n is a, c, g, or t

<400> SEQUENCE: 70
nnnrycgryn nnnnnngggg gg 22

<210> SEQ ID NO 71
<211> LENGTH: 23
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(17)
<223> OTHER INFORMATION: n is a, c, g, or t

<400> SEQUENCE: 71
nnnrycgryn nnnnnnnggg ggg 23

<210> SEQ ID NO 72
<211> LENGTH: 24
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(18)
<223> OTHER INFORMATION: n is a, c, g, or t

<400> SEQUENCE: 72
nnnrycgryn nnnnnnnngg gggg 24

<210> SEQ ID NO 73
<211> LENGTH: 25
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(19)
<223> OTHER INFORMATION: n is a, c, g, or t

<400> SEQUENCE: 73
nnnrycgryn nnnnnnnnng ggggg 25

<210> SEQ ID NO 74
<211> LENGTH: 26
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t

<400> SEQUENCE: 74
nnnrycgryn nnnnnnnnnn gggggg 26

<210> SEQ ID NO 75
<211> LENGTH: 27
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(21)
<223> OTHER INFORMATION: n is a, c, g, or t

<400> SEQUENCE: 75
nnnrycgryn nnnnnnnnnn ngggggg 27

<210> SEQ ID NO 76
<211> LENGTH: 28
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:

<221> NAME/KEY: misc_feature
<222> LOCATION: (10)..(22)
<223> OTHER INFORMATION: n is a, c, g, or t

<400> SEQUENCE: 76
nnnrycgryn nnnnnnnnnn nngggggg 28

<210> SEQ ID NO 77
<211> LENGTH: 19
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 77
nnnrycgryn nngggggggg 19

<210> SEQ ID NO 78
<211> LENGTH: 20
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t

<400> SEQUENCE: 78
nnnrycgryn nnngggggggg 20

<210> SEQ ID NO 79
<211> LENGTH: 21
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(14)
<223> OTHER INFORMATION: n is a, c, g, or t

<400> SEQUENCE: 79
nnnrycgryn nnnngggggg g 21

<210> SEQ ID NO 80
<211> LENGTH: 22
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(15)
<223> OTHER INFORMATION: n is a, c, g, or t

<400> SEQUENCE: 80
nnnrycgryn nnnnnggggg gg 22

<210> SEQ ID NO 81
<211> LENGTH: 23
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(16)
<223> OTHER INFORMATION: n is a, c, g, or t

<400> SEQUENCE: 81
nnnrycgryn nnnnnngggg ggg 23

<210> SEQ ID NO 82
<211> LENGTH: 24
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(17)
<223> OTHER INFORMATION: n is a, c, g, or t

<400> SEQUENCE: 82
nnnrycgryn nnnnnnnggg gggg 24

<210> SEQ ID NO 83
<211> LENGTH: 25
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(18)
<223> OTHER INFORMATION: n is a, c, g, or t

<400> SEQUENCE: 83
nnnrycgryn nnnnnnnngg ggggg 25

<210> SEQ ID NO 84
<211> LENGTH: 26
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)

-continued

<223> OTHER INFORMATION: n is a, c, g, or t
<220> FEATURE:
<221> NAME/KEY: misc_feature
<222> LOCATION: (10)..(19)
<223> OTHER INFORMATION: n is a, c, g, or t

<400> SEQUENCE: 84
nnnrycgryn nnnnnnnnng gggggg 26

<210> SEQ ID NO 85
<211> LENGTH: 27
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t

<400> SEQUENCE: 85
nnnrycgryn nnnnnnnnnn ggggggg 27

<210> SEQ ID NO 86
<211> LENGTH: 28
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(21)
<223> OTHER INFORMATION: n is a, c, g, or t

<400> SEQUENCE: 86
nnnrycgryn nnnnnnnnnn ngggggggg 28

<210> SEQ ID NO 87
<211> LENGTH: 29
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(22)
<223> OTHER INFORMATION: n is a, c, g, or t

<400> SEQUENCE: 87
nnnrycgryn nnnnnnnnnn nngggggggg 29

<210> SEQ ID NO 88
<211> LENGTH: 20
<212> TYPE: DNA
<213> ORGANISM: Artificial sequence
<220> FEATURE:
<223> OTHER INFORMATION: synthetic
<220> FEATURE:
<221> NAME/KEY: misc_feature -continued
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 88
nnnrycgryn nngggggggg 20

<210> SEQ ID NO 89
<211> LENGTH: 21
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t

<400> SEQUENCE: 89
nnnrycgryn nnnggggggg g 21

<210> SEQ ID NO 90
<211> LENGTH: 22
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(14)
<223> OTHER INFORMATION: n is a, c, g, or t

<400> SEQUENCE: 90
nnnrycgryn nnnngggggg gg 22

<210> SEQ ID NO 91
<211> LENGTH: 23
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(15)
<223> OTHER INFORMATION: n is a, c, g, or t

<400> SEQUENCE: 91
nnnrycgryn nnnnnggggg ggg 23

<210> SEQ ID NO 92
<211> LENGTH: 24
<212> TYPE: DNA
<213> ORGANISM: Artificial sequence
<220> FEATURE:
<223> OTHER INFORMATION: synthetic
<220> FEATURE:

<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(16)
<223> OTHER INFORMATION: n is a, c, g, or t

<400> SEQUENCE: 92
nnnrycgryn nnnnnngggg gggg 24

<210> SEQ ID NO 93
<211> LENGTH: 25
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(17)
<223> OTHER INFORMATION: n is a, c, g, or t

<400> SEQUENCE: 93
nnnrycgryn nnnnnnnggg ggggg 25

<210> SEQ ID NO 94
<211> LENGTH: 26
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(18)
<223> OTHER INFORMATION: n is a, c, g, or t

<400> SEQUENCE: 94
nnnrycgryn nnnnnnnngg gggggg 26

<210> SEQ ID NO 95
<211> LENGTH: 27
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(19)
<223> OTHER INFORMATION: n is a, c, g, or t

<400> SEQUENCE: 95
nnnrycgryn nnnnnnnnng ggggggg 27

<210> SEQ ID NO 96
<211> LENGTH: 28
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t

<400> SEQUENCE: 96
nnnrycgryn nnnnnnnnnn gggggggg 28

<210> SEQ ID NO 97
<211> LENGTH: 29
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(21)
<223> OTHER INFORMATION: n is a, c, g, or t

<400> SEQUENCE: 97
nnnrycgryn nnnnnnnnnn ngggggggg 29

<210> SEQ ID NO 98
<211> LENGTH: 30
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(22)
<223> OTHER INFORMATION: n is a, c, g, or t

<400> SEQUENCE: 98
nnnrycgryn nnnnnnnnnn nngggggggg 30

<210> SEQ ID NO 99
<211> LENGTH: 21
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 99
nnnrycgryn nngggggggg g 21

<210> SEQ ID NO 100
<211> LENGTH: 22
<212> TYPE: DNA
<213> ORGANISM: Artificial sequence
<220> FEATURE:

-continued

<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t

<400> SEQUENCE: 100
nnnrycgryn nnngggggggg gg 22

<210> SEQ ID NO 101
<211> LENGTH: 23
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(14)
<223> OTHER INFORMATION: n is a, c, g, or t

<400> SEQUENCE: 101
nnnrycgryn nnnngggggg ggg 23

<210> SEQ ID NO 102
<211> LENGTH: 24
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(15)
<223> OTHER INFORMATION: n is a, c, g, or t

<400> SEQUENCE: 102
nnnrycgryn nnnnnggggg gggg 24

<210> SEQ ID NO 103
<211> LENGTH: 25
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(16)
<223> OTHER INFORMATION: n is a, c, g, or t

<400> SEQUENCE: 103
nnnrycgryn nnnnnngggg ggggg 25

<210> SEQ ID NO 104
<211> LENGTH: 26
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(17)
<223> OTHER INFORMATION: n is a, c, g, or t

<400> SEQUENCE: 104
nnnrycgryn nnnnnnnggg gggggg 26

<210> SEQ ID NO 105
<211> LENGTH: 27
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(18)
<223> OTHER INFORMATION: n is a, c, g, or t

<400> SEQUENCE: 105
nnnrycgryn nnnnnnnngg ggggggg 27

<210> SEQ ID NO 106
<211> LENGTH: 28
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(19)
<223> OTHER INFORMATION: n is a, c, g, or t

<400> SEQUENCE: 106
nnnrycgryn nnnnnnnnng gggggggg 28

<210> SEQ ID NO 107
<211> LENGTH: 29
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t

<400> SEQUENCE: 107
nnnrycgryn nnnnnnnnnn ggggggggg 29

<210> SEQ ID NO 108
<211> LENGTH: 30
<212> TYPE: DNA

<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(21)
<223> OTHER INFORMATION: n is a, c, g, or t

<400> SEQUENCE: 108
nnnrycgryn nnnnnnnnnn ngggggggg 30

<210> SEQ ID NO 109
<211> LENGTH: 31
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(22)
<223> OTHER INFORMATION: n is a, c, g, or t

<400> SEQUENCE: 109
nnnrycgryn nnnnnnnnnn nngggggggg g 31

<210> SEQ ID NO 110
<211> LENGTH: 22
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 110
nnnrycgryn nngggggggg gg 22

<210> SEQ ID NO 111
<211> LENGTH: 23
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(13)
<223> OTHER INFORMATION: n is a, c, g, or t

<400> SEQUENCE: 111
nnnrycgryn nnngggggggg ggg 23

<210> SEQ ID NO 112
<211> LENGTH: 24

<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(14)
<223> OTHER INFORMATION: n is a, c, g, or t

<400> SEQUENCE: 112
nnnrycgryn nnnnggggg gggg 24

<210> SEQ ID NO 113
<211> LENGTH: 25
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(15)
<223> OTHER INFORMATION: n is a, c, g, or t

<400> SEQUENCE: 113
nnnrycgryn nnnnngggg ggggg 25

<210> SEQ ID NO 114
<211> LENGTH: 26
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(16)
<223> OTHER INFORMATION: n is a, c, g, or t

<400> SEQUENCE: 114
nnnrycgryn nnnnnnggg gggggg 26

<210> SEQ ID NO 115
<211> LENGTH: 27
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(17)
<223> OTHER INFORMATION: n is a, c, g, or t

<400> SEQUENCE: 115
nnnrycgryn nnnnnnngg ggggggg 27

<210> SEQ ID NO 116

<211> LENGTH: 28
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(18)
<223> OTHER INFORMATION: n is a, c, g, or t

<400> SEQUENCE: 116
nnnrycgryn nnnnnnnngg gggggggg 28

<210> SEQ ID NO 117
<211> LENGTH: 29
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(19)
<223> OTHER INFORMATION: n is a, c, g, or t

<400> SEQUENCE: 117
nnnrycgryn nnnnnnnnng ggggggggg 29

<210> SEQ ID NO 118
<211> LENGTH: 30
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(20)
<223> OTHER INFORMATION: n is a, c, g, or t

<400> SEQUENCE: 118
nnnrycgryn nnnnnnnnnn gggggggggg 30

<210> SEQ ID NO 119
<211> LENGTH: 31
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(21)
<223> OTHER INFORMATION: n is a, c, g, or t

<400> SEQUENCE: 119
nnnrycgryn nnnnnnnnnn nggggggggg g 31

<210> SEQ ID NO 120
<211> LENGTH: 32
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (10)..(22)
<223> OTHER INFORMATION: n is a, c, g, or t

<400> SEQUENCE: 120
nnnrycgryn nnnnnnnnnn nngggggggg gg 32

<210> SEQ ID NO 121
<211> LENGTH: 10
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (8)..(10)
<223> OTHER INFORMATION: n is a, c, g, or t

<400> SEQUENCE: 121 nnndcgwnnn 10

<210> SEQ ID NO 122
<211> LENGTH: 10
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (8)..(10)
<223> OTHER INFORMATION: n is a, c, g, or t

<400> SEQUENCE: 122 nnntcgwnnn 10

<210> SEQ ID NO 123
<211> LENGTH: 18
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t

<400> SEQUENCE: 123
ggnnnrycgr ynnngggg 18

<210> SEQ ID NO 124
<211> LENGTH: 19
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(15)
<223> OTHER INFORMATION: n is a, c, g, or t

<400> SEQUENCE: 124
ggnnnrycgr ynnnngggg 19

<210> SEQ ID NO 125
<211> LENGTH: 20
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(16)
<223> OTHER INFORMATION: n is a, c, g, or t

<400> SEQUENCE: 125
ggnnnrycgr ynnnnngggg 20

<210> SEQ ID NO 126
<211> LENGTH: 21
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(17)
<223> OTHER INFORMATION: n is a, c, g, or t

<400> SEQUENCE: 126
ggnnnrycgr ynnnnnnggg g 21

<210> SEQ ID NO 127
<211> LENGTH: 22
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(18)
<223> OTHER INFORMATION: n is a, c, g, or t

<400> SEQUENCE: 127
ggnnnrycgr ynnnnnnngg gg 22

<210> SEQ ID NO 128
<211> LENGTH: 23
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(19)
<223> OTHER INFORMATION: n is a, c, g, or t

<400> SEQUENCE: 128
ggnnnrycgr ynnnnnnnng ggg 23

<210> SEQ ID NO 129
<211> LENGTH: 24
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(20)
<223> OTHER INFORMATION: n is a, c, g, or t

<400> SEQUENCE: 129
ggnnnrycgr ynnnnnnnnn gggg 24

<210> SEQ ID NO 130
<211> LENGTH: 25
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(21)
<223> OTHER INFORMATION: n is a, c, g, or t

<400> SEQUENCE: 130
ggnnnrycgr ynnnnnnnnn ngggg 25

<210> SEQ ID NO 131
<211> LENGTH: 26
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(22)
<223> OTHER INFORMATION: n is a, c, g, or t

<400> SEQUENCE: 131

-continued ggnnnrycgr ynnnnnnnnn nngggg 26

<210> SEQ ID NO 132
<211> LENGTH: 27
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(23)
<223> OTHER INFORMATION: n is a, c, g, or t

<400> SEQUENCE: 132
ggnnnrycgr ynnnnnnnnn nnngggg 27

<210> SEQ ID NO 133
<211> LENGTH: 28
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(24)
<223> OTHER INFORMATION: n is a, c, g, or t

<400> SEQUENCE: 133
ggnnnrycgr ynnnnnnnnn nnnngggg 28

<210> SEQ ID NO 134
<211> LENGTH: 19
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t

<400> SEQUENCE: 134
ggnnnrycgr ynnngggg 19

<210> SEQ ID NO 135
<211> LENGTH: 20
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(15)
<223> OTHER INFORMATION: n is a, c, g, or t

<400> SEQUENCE: 135

```
ggnnnrycgr ynnnnggggg                                                 20


<210> SEQ ID NO 136
<211> LENGTH: 21
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(16)
<223> OTHER INFORMATION: n is a, c, g, or t

<400> SEQUENCE: 136

ggnnnrycgr ynnnnngggg g                                               21


<210> SEQ ID NO 137
<211> LENGTH: 22
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(17)
<223> OTHER INFORMATION: n is a, c, g, or t

<400> SEQUENCE: 137

ggnnnrycgr ynnnnnnggg gg                                              22


<210> SEQ ID NO 138
<211> LENGTH: 23
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(18)
<223> OTHER INFORMATION: n is a, c, g, or t

<400> SEQUENCE: 138

ggnnnrycgr ynnnnnnngg ggg                                             23


<210> SEQ ID NO 139
<211> LENGTH: 24
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(19)
<223> OTHER INFORMATION: n is a, c, g, or t
```

<400> SEQUENCE: 139
ggnnnrycgr ynnnnnnnng gggg 24

<210> SEQ ID NO 140
<211> LENGTH: 25
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(20)
<223> OTHER INFORMATION: n is a, c, g, or t

<400> SEQUENCE: 140
ggnnnrycgr ynnnnnnnnn ggggg 25

<210> SEQ ID NO 141
<211> LENGTH: 26
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(21)
<223> OTHER INFORMATION: n is a, c, g, or t

<400> SEQUENCE: 141
ggnnnrycgr ynnnnnnnnn nggggg 26

<210> SEQ ID NO 142
<211> LENGTH: 27
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(22)
<223> OTHER INFORMATION: n is a, c, g, or t

<400> SEQUENCE: 142
ggnnnrycgr ynnnnnnnnn nnggggg 27

<210> SEQ ID NO 143
<211> LENGTH: 28
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(23)
<223> OTHER INFORMATION: n is a, c, g, or t

<400> SEQUENCE: 143
ggnnnrycgr ynnnnnnnnn nnnggggg 28

<210> SEQ ID NO 144
<211> LENGTH: 29
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(24)
<223> OTHER INFORMATION: n is a, c, g, or t

<400> SEQUENCE: 144
ggnnnrycgr ynnnnnnnnn nnnnggggg 29

<210> SEQ ID NO 145
<211> LENGTH: 20
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t

<400> SEQUENCE: 145
ggnnnrycgr ynnngggggg 20

<210> SEQ ID NO 146
<211> LENGTH: 21
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(15)
<223> OTHER INFORMATION: n is a, c, g, or t

<400> SEQUENCE: 146
ggnnnrycgr ynnnnggggg g 21

<210> SEQ ID NO 147
<211> LENGTH: 22
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(16)

-continued

<223> OTHER INFORMATION: n is a, c, g, or t

<400> SEQUENCE: 147
ggnnnrycgr ynnnnngggg gg 22

<210> SEQ ID NO 148
<211> LENGTH: 23
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(17)
<223> OTHER INFORMATION: n is a, c, g, or t

<400> SEQUENCE: 148
ggnnnrycgr ynnnnnnggg ggg 23

<210> SEQ ID NO 149
<211> LENGTH: 24
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(18)
<223> OTHER INFORMATION: n is a, c, g, or t

<400> SEQUENCE: 149
ggnnnrycgr ynnnnnnngg gggg 24

<210> SEQ ID NO 150
<211> LENGTH: 25
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(19)
<223> OTHER INFORMATION: n is a, c, g, or t

<400> SEQUENCE: 150
ggnnnrycgr ynnnnnnnng ggggg 25

<210> SEQ ID NO 151
<211> LENGTH: 26
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(20)
<223> OTHER INFORMATION: n is a, c, g, or t

<400> SEQUENCE: 151
ggnnnrycgr ynnnnnnnnn gggggg 26

<210> SEQ ID NO 152
<211> LENGTH: 27
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(21)
<223> OTHER INFORMATION: n is a, c, g, or t

<400> SEQUENCE: 152
ggnnnrycgr ynnnnnnnnn ngggggg 27

<210> SEQ ID NO 153
<211> LENGTH: 28
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(22)
<223> OTHER INFORMATION: n is a, c, g, or t

<400> SEQUENCE: 153
ggnnnrycgr ynnnnnnnnn nngggggg 28

<210> SEQ ID NO 154
<211> LENGTH: 29
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(23)
<223> OTHER INFORMATION: n is a, c, g, or t

<400> SEQUENCE: 154
ggnnnrycgr ynnnnnnnnn nnngggggg 29

<210> SEQ ID NO 155
<211> LENGTH: 30
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:

<221> NAME/KEY: misc_feature
<222> LOCATION: (12)..(24)
<223> OTHER INFORMATION: n is a, c, g, or t

<400> SEQUENCE: 155
ggnnnrycgr ynnnnnnnnn nnnngggggg 30

<210> SEQ ID NO 156
<211> LENGTH: 21
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t

<400> SEQUENCE: 156
ggnnnrycgr ynnngggggg g 21

<210> SEQ ID NO 157
<211> LENGTH: 22
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(15)
<223> OTHER INFORMATION: n is a, c, g, or t

<400> SEQUENCE: 157
ggnnnrycgr ynnnnggggg gg 22

<210> SEQ ID NO 158
<211> LENGTH: 23
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(16)
<223> OTHER INFORMATION: n is a, c, g, or t

<400> SEQUENCE: 158
ggnnnrycgr ynnnnngggg ggg 23

<210> SEQ ID NO 159
<211> LENGTH: 24
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t

```
<220> FEATURE:
<221> NAME/KEY: misc_feature
<222> LOCATION: (12)..(17)
<223> OTHER INFORMATION: n is a, c, g, or t

<400> SEQUENCE: 159

ggnnnrycgr ynnnnnnggg gggg                                              24


<210> SEQ ID NO 160
<211> LENGTH: 25
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(18)
<223> OTHER INFORMATION: n is a, c, g, or t

<400> SEQUENCE: 160

ggnnnrycgr ynnnnnnngg ggggg                                             25


<210> SEQ ID NO 161
<211> LENGTH: 26
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(19)
<223> OTHER INFORMATION: n is a, c, g, or t

<400> SEQUENCE: 161

ggnnnrycgr ynnnnnnnng gggggg                                            26


<210> SEQ ID NO 162
<211> LENGTH: 27
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(20)
<223> OTHER INFORMATION: n is a, c, g, or t

<400> SEQUENCE: 162

ggnnnrycgr ynnnnnnnnn ggggggg                                           27


<210> SEQ ID NO 163
<211> LENGTH: 28
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
```

<223> OTHER INFORMATION: n is a, c, g, or t
<220> FEATURE:
<221> NAME/KEY: misc_feature
<222> LOCATION: (12)..(21)
<223> OTHER INFORMATION: n is a, c, g, or t

<400> SEQUENCE: 163
ggnnnrycgr ynnnnnnnnn ngggggg 28

<210> SEQ ID NO 164
<211> LENGTH: 29
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(22)
<223> OTHER INFORMATION: n is a, c, g, or t

<400> SEQUENCE: 164
ggnnnrycgr ynnnnnnnnn nngggggg 29

<210> SEQ ID NO 165
<211> LENGTH: 30
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(23)
<223> OTHER INFORMATION: n is a, c, g, or t

<400> SEQUENCE: 165
ggnnnrycgr ynnnnnnnnn nnngggggg 30

<210> SEQ ID NO 166
<211> LENGTH: 31
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(24)
<223> OTHER INFORMATION: n is a, c, g, or t

<400> SEQUENCE: 166
ggnnnrycgr ynnnnnnnnn nnnngggggg g 31

<210> SEQ ID NO 167
<211> LENGTH: 22
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t

<400> SEQUENCE: 167
ggnnnrycgr ynnngggggg gg 22

<210> SEQ ID NO 168
<211> LENGTH: 23
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(15)
<223> OTHER INFORMATION: n is a, c, g, or t

<400> SEQUENCE: 168
ggnnnrycgr ynnnnggggg ggg 23

<210> SEQ ID NO 169
<211> LENGTH: 24
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(16)
<223> OTHER INFORMATION: n is a, c, g, or t

<400> SEQUENCE: 169
ggnnnrycgr ynnnnngggg gggg 24

<210> SEQ ID NO 170
<211> LENGTH: 25
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(17)
<223> OTHER INFORMATION: n is a, c, g, or t

<400> SEQUENCE: 170
ggnnnrycgr ynnnnnnggg ggggg 25

<210> SEQ ID NO 171
<211> LENGTH: 26
<212> TYPE: DNA
<213> ORGANISM: Artificial sequence
<220> FEATURE:
<223> OTHER INFORMATION: synthetic
<220> FEATURE:

-continued

<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(18)
<223> OTHER INFORMATION: n is a, c, g, or t

<400> SEQUENCE: 171
ggnnnrycgr ynnnnnnngg gggggg 26

<210> SEQ ID NO 172
<211> LENGTH: 27
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(19)
<223> OTHER INFORMATION: n is a, c, g, or t

<400> SEQUENCE: 172
ggnnnrycgr ynnnnnnnng ggggggg 27

<210> SEQ ID NO 173
<211> LENGTH: 28
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(20)
<223> OTHER INFORMATION: n is a, c, g, or t

<400> SEQUENCE: 173
ggnnnrycgr ynnnnnnnnn gggggggg 28

<210> SEQ ID NO 174
<211> LENGTH: 29
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(21)
<223> OTHER INFORMATION: n is a, c, g, or t

<400> SEQUENCE: 174
ggnnnrycgr ynnnnnnnnn ngggggggg 29

<210> SEQ ID NO 175
<211> LENGTH: 30
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(22)
<223> OTHER INFORMATION: n is a, c, g, or t

<400> SEQUENCE: 175
ggnnnrycgr ynnnnnnnnn nngggggggg 30

<210> SEQ ID NO 176
<211> LENGTH: 31
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(23)
<223> OTHER INFORMATION: n is a, c, g, or t

<400> SEQUENCE: 176
ggnnnrycgr ynnnnnnnnn nnnggggggg g 31

<210> SEQ ID NO 177
<211> LENGTH: 32
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(24)
<223> OTHER INFORMATION: n is a, c, g, or t

<400> SEQUENCE: 177
ggnnnrycgr ynnnnnnnnn nnnngggggg gg 32

<210> SEQ ID NO 178
<211> LENGTH: 23
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t

<400> SEQUENCE: 178
ggnnnrycgr ynnngggggg ggg 23

<210> SEQ ID NO 179
<211> LENGTH: 24
<212> TYPE: DNA
<213> ORGANISM: Artificial sequence
<220> FEATURE:

<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(15)
<223> OTHER INFORMATION: n is a, c, g, or t

<400> SEQUENCE: 179
ggnnnrycgr ynnnnggggg gggg 24

<210> SEQ ID NO 180
<211> LENGTH: 25
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(16)
<223> OTHER INFORMATION: n is a, c, g, or t

<400> SEQUENCE: 180
ggnnnrycgr ynnnnngggg ggggg 25

<210> SEQ ID NO 181
<211> LENGTH: 26
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(17)
<223> OTHER INFORMATION: n is a, c, g, or t

<400> SEQUENCE: 181
ggnnnrycgr ynnnnnnggg gggggg 26

<210> SEQ ID NO 182
<211> LENGTH: 27
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(18)
<223> OTHER INFORMATION: n is a, c, g, or t

<400> SEQUENCE: 182
ggnnnrycgr ynnnnnnngg ggggggg 27

<210> SEQ ID NO 183
<211> LENGTH: 28
<212> TYPE: DNA
<213> ORGANISM: Artificial sequence -continued
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(19)
<223> OTHER INFORMATION: n is a, c, g, or t

<400> SEQUENCE: 183
ggnnnrycgr ynnnnnnnng ggggggg 28

<210> SEQ ID NO 184
<211> LENGTH: 29
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(20)
<223> OTHER INFORMATION: n is a, c, g, or t

<400> SEQUENCE: 184
ggnnnrycgr ynnnnnnnnn gggggggg 29

<210> SEQ ID NO 185
<211> LENGTH: 30
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(21)
<223> OTHER INFORMATION: n is a, c, g, or t

<400> SEQUENCE: 185
ggnnnrycgr ynnnnnnnnn ngggggggg 30

<210> SEQ ID NO 186
<211> LENGTH: 31
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(22)
<223> OTHER INFORMATION: n is a, c, g, or t

<400> SEQUENCE: 186
ggnnnrycgr ynnnnnnnnn nngggggggg g 31

<210> SEQ ID NO 187
<211> LENGTH: 32
<212> TYPE: DNA

<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(23)
<223> OTHER INFORMATION: n is a, c, g, or t

<400> SEQUENCE: 187
ggnnnrycgr ynnnnnnnnn nnnggggggg gg 32

<210> SEQ ID NO 188
<211> LENGTH: 33
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(24)
<223> OTHER INFORMATION: n is a, c, g, or t

<400> SEQUENCE: 188
ggnnnrycgr ynnnnnnnnn nnnngggggg ggg 33

<210> SEQ ID NO 189
<211> LENGTH: 24
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(14)
<223> OTHER INFORMATION: n is a, c, g, or t

<400> SEQUENCE: 189
ggnnnrycgr ynnngggggg gggg 24

<210> SEQ ID NO 190
<211> LENGTH: 25
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(15)
<223> OTHER INFORMATION: n is a, c, g, or t

<400> SEQUENCE: 190
ggnnnrycgr ynnnnggggg ggggg 25

<210> SEQ ID NO 191
<211> LENGTH: 26

<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(16)
<223> OTHER INFORMATION: n is a, c, g, or t

<400> SEQUENCE: 191
ggnnnrycgr ynnnnngggg gggggg 26

<210> SEQ ID NO 192
<211> LENGTH: 27
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(17)
<223> OTHER INFORMATION: n is a, c, g, or t

<400> SEQUENCE: 192
ggnnnrycgr ynnnnnnggg ggggggg 27

<210> SEQ ID NO 193
<211> LENGTH: 28
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(18)
<223> OTHER INFORMATION: n is a, c, g, or t

<400> SEQUENCE: 193
ggnnnrycgr ynnnnnnngg gggggggg 28

<210> SEQ ID NO 194
<211> LENGTH: 29
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(19)
<223> OTHER INFORMATION: n is a, c, g, or t

<400> SEQUENCE: 194
ggnnnrycgr ynnnnnnnng ggggggggg 29

<210> SEQ ID NO 195

-continued

<211> LENGTH: 30
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(20)
<223> OTHER INFORMATION: n is a, c, g, or t

<400> SEQUENCE: 195
ggnnnrycgr ynnnnnnnnn gggggggggg 30

<210> SEQ ID NO 196
<211> LENGTH: 31
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(21)
<223> OTHER INFORMATION: n is a, c, g, or t

<400> SEQUENCE: 196
ggnnnrycgr ynnnnnnnnn nggggggggg g 31

<210> SEQ ID NO 197
<211> LENGTH: 32
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(22)
<223> OTHER INFORMATION: n is a, c, g, or t

<400> SEQUENCE: 197
ggnnnrycgr ynnnnnnnnn nngggggggg gg 32

<210> SEQ ID NO 198
<211> LENGTH: 33
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(23)
<223> OTHER INFORMATION: n is a, c, g, or t

<400> SEQUENCE: 198
ggnnnrycgr ynnnnnnnnn nnnggggggg ggg 33

-continued

```
<210> SEQ ID NO 199
<211> LENGTH: 34
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (12)..(24)
<223> OTHER INFORMATION: n is a, c, g, or t

<400> SEQUENCE: 199

ggnnnrycgr ynnnnnnnnn nnnnggggggg gggg                      34


<210> SEQ ID NO 200
<211> LENGTH: 24
<212> TYPE: DNA
<213> ORGANISM: Artificial sequence
<220> FEATURE:
<223> OTHER INFORMATION: synthetic

<400> SEQUENCE: 200

tcgtcgtttt gtcgttttgt cgtt                                  24
```